US011541000B2

(12) United States Patent
Shanler et al.

(10) Patent No.: US 11,541,000 B2
(45) Date of Patent: Jan. 3, 2023

(54) PHARMACEUTICAL CREAM COMPOSITIONS OF OXYMETAZOLINE AND METHODS OF USE

(71) Applicant: EPI Health, LLC, Charleston, SC (US)

(72) Inventors: Stuart D. Shanler, Malvern, PA (US); Christopher Powala, Radnor, PA (US)

(73) Assignee: EPI HEALTH, LLC, Charleston, SC (US)

( * ) Notice: Subject to any disclaimer, the term of this patent is extended or adjusted under 35 U.S.C. 154(b) by 0 days.

(21) Appl. No.: 16/673,549

(22) Filed: Nov. 4, 2019

(65) Prior Publication Data

US 2020/0276108 A1 Sep. 3, 2020

Related U.S. Application Data

(63) Continuation of application No. 16/267,590, filed on Feb. 5, 2019, now abandoned, which is a continuation of application No. 14/144,106, filed on Dec. 30, 2013, now abandoned, which is a continuation of application No. 13/396,165, filed on Feb. 14, 2012, now abandoned.

(60) Provisional application No. 61/443,210, filed on Feb. 15, 2011.

(51) Int. Cl.
| | | |
|---|---|---|
| *A61K 31/575* | (2006.01) | |
| *A61K 47/02* | (2006.01) | |
| *A61K 31/192* | (2006.01) | |
| *A61K 47/26* | (2006.01) | |
| *A61K 9/00* | (2006.01) | |
| *A61K 9/06* | (2006.01) | |
| *A61K 31/4164* | (2006.01) | |
| *A61K 47/14* | (2017.01) | |
| *A61K 45/06* | (2006.01) | |

(52) U.S. Cl.
CPC ............. *A61K 9/0014* (2013.01); *A61K 9/06* (2013.01); *A61K 31/4164* (2013.01); *A61K 45/06* (2013.01); *A61K 47/14* (2013.01)

(58) Field of Classification Search
None
See application file for complete search history.

(56) References Cited

U.S. PATENT DOCUMENTS

| | | | |
|---|---|---|---|
| 3,147,275 | A | 9/1964 | Fruhstorfer et al. |
| 6,433,024 | B1 | 8/2002 | Popp et al. |
| 6,960,615 | B2 | 11/2005 | Glassman et al. |
| 7,439,241 | B2 | 10/2008 | DeJovin et al. |
| 7,812,049 | B2 | 10/2010 | Shanler et al. |
| 7,838,563 | B2 | 11/2010 | DeJovin et al. |
| 8,114,898 | B2 | 2/2012 | Shanler et al. |
| 8,420,688 | B2 | 4/2013 | Shanler et al. |
| 2003/0108496 | A1 | 6/2003 | Yu et al. |
| 2004/0024588 | A1 | 2/2004 | Watson et al. |
| 2005/0165079 | A1 | 7/2005 | Shanler et al. |
| 2007/0048224 | A1 | 3/2007 | Waugh et al. |
| 2008/0193551 | A1 | 8/2008 | De Waard et al. |
| 2009/0061020 | A1 | 3/2009 | Theobald et al. |
| 2009/0130027 | A1 | 5/2009 | Shanler et al. |
| 2011/0224216 | A1 | 9/2011 | Andres et al. |
| 2012/0082625 | A1 | 4/2012 | Graeber et al. |
| 2012/0149748 | A1 | 6/2012 | Shanler et al. |
| 2012/0208858 | A1 | 8/2012 | Shanler et al. |
| 2013/0079379 | A1 | 3/2013 | Shanler et al. |

FOREIGN PATENT DOCUMENTS

| | | |
|---|---|---|
| WO | WO-20040105703 A3 | 3/2005 |
| WO | WO-20050115395 A2 | 12/2005 |
| WO | WO-20060105450 A2 | 10/2006 |
| WO | WO-20070000192 A1 | 1/2007 |
| WO | WO-20120075319 A3 | 3/2012 |
| WO | WO-20120047645 A2 | 4/2012 |
| WO | WO-20120112566 A1 | 8/2012 |

OTHER PUBLICATIONS

"Difference Between Acne and Rosacea", Rosacea World, p. 1; http://www.rosaceaworld.com/difference-between-acne-and-rosacea.
"Frequently Asked Questions" Mar. 27, 2013, Rosacea.org, pp. 5-6; http://www.rosacea.org/patients/faq.php.
"How is Rosacea Different to Acne Vulgaris?" Mar. 27, 2018, 1 page; http://stason.org/TULARC/health/rosaceadisorder/1-2-How-is-?Rosacea-differnt-to-Acne-vulgaris.
What is Rosacea? 2012, National Rosacea Society.
Afrin Original—Oxymetazoline Hydrochloride Spray Product Label, Bayer Healthcare LLC, Feb. 2017.
Anderson et al. The Practice of Medicinal Chemistry, 1996, 3rd Edition, cover and table of contents only, 32 pages.
Baldwin "Clinically Diagnosing Acne Vulgaris vs. Rosacea: What's the Difference?" Mar. 27, 2013, http://www.medscape.org/viewarticle/588257, p. 1.
Bechtel et al. "Rosacea: Choosing Among the Topical and Systemic Therapeutic Options" Dec. 2011, Practical Dermatology 45-48.
Berge et al. "Pharmaceutical Salts" Jan. 1977, J. Pharma. Sci. 66(1):1-18.
Blount et al. "Rosacea: A Common, Yet Commonly Overlooked, Condition" Aug. 1, 2002, American Family Physician, 66(3):435-440.
Breneman et al. "Double-blind, randomized, vehicle-controlled clinical trial of once-daily benzoyl peroxide/clindamycin topical gel in the treatment of patients with moderate to severe rosacea" 2004, Int. J. Dermatol. 43(5):381-387.

(Continued)

*Primary Examiner* — Layla Soroush
(74) *Attorney, Agent, or Firm* — Blank Rome LLP

(57) ABSTRACT

The present invention is directed to: a) a method of treating telangiectasia; b) a method of treating inflammatory lesions; and c) a method of treating two or more symptoms of *rosacea* selected from erythema, telangiectasia, or inflammatory lesions comprising topical administration of a pharmaceutical composition comprising oxymetazoline and a pharmaceutically acceptable excipient.

2 Claims, 5 Drawing Sheets

(56) References Cited

OTHER PUBLICATIONS

Brown et al. "Acne Vulargis, Folliculitis, and Acne Rosacea" 5 pages; http://www.docstoc.com/docs/48078014/acnevulgaris-follliculitis-and-acne-rosacea.

Ceilley "Advances in the Topical Treatment of Acne and Rosacea" Sep. 1, 2004, J. Drugs in Dermatology, 20 pages; http://custom.buyitsellit.com/25365/journal_of_drugs_in_dermatology_2004.pdf.

DelRosso "Advances in understanding and managing rosacea: part 1, connecting the dots between pathophysiological mechanisms and common clinical features of rasacea with emphasis on vascular changes and facial erythema" Mar. 2012, J. Clin. Aesth. Derm. 5(3):16-25.

DelRosso "Advances in Understanding and Managing Rosacea: part 2, The Central Role, Evaluation and Medical Management of Diffuse and Persistent Facial Erythema of Rosacea" Mar. 2012, J. Clin. Aesth. Derm. 5(3):26-35.

Drummond et al. "Blushing in Rosacea Sufferers" Feb. 2012, J. Phychosomatic Res. 72(2):153-158.

Elewski et al. "Rosacea—global diversity and optimized outcome: proposed international consensus from the Rosacec International Expert Group" Feb. 2011 , J. European Acad. Derm. And Venereal. 25(2) :188-200.

European Search Report and Written Opinion for EP 19170085 dated Sep. 17, 2019.

FDA Guidance for Industry, Bioanalytical Method Validation, May 2001, U.S. Dept. Health and Human Services Food and Drug Administration, Center for Drug Evaluation and Research (CDER), Center for Veterinary Medicine (CVM).

Ghosh et al. "Transdermal and Topical Drug Delivery Systems," Chapter 14 1997 Interpharm Press.

Gould Salt Selection for Basic Drugs, 1986, Intl. J. Pharmac. 33:201-217.

Guarrera et al. "Flushing in Rosacea: A Possible Mechanism" 1982, Archives Dermatol Res. 272:311-316.

Guimaraes et al. "Vascular Adrenoceptors: An Update" Jun. 2001 , Pharmacol Rev. 53(2):319-356.

International Search Report and Written Opinion for PCT/US2012/025068 dated Apr. 3, 2012.

International Search Report for PCT/US2004/016799 dated Nov. 17, 2004.

International Search Report for PCT/US2005/018288 dated Dec. 7, 2005.

International Search Report for PCT/US2011/062936 dated Jun. 1, 2012.

Jarajapu et al. "Functional Characterization of alpha1-Adrenoceptor Subtypes in Human Subcutaneous Resistance Arteries" Nov. 2001 , J Pharmacol Exp Ther 299(2):729-734.

McClellan et al. "Topical Metronidazole: A Review of its Use in Rosacea" May-Jun. 2000, Am. J. Clin. Dermatol. 1 (3):191-199.

Norwood et al. "Treating Rosacea" 2007, U.S. Pharm. 32(9):45-54.

Piascik et al. "alpha1-Adrenergic Receptors: New Insights and Directions" Aug. 2001, J Pharmacol Exp Ther. 298 (2):403-410.

Rebora "The Management of Rosacea" 2002, American Journal of Clinical Dermatology 3:489-496.

Ruffolo et al. "Receptor Interactions of Imidazolines, IX. Cirazoline is an Alpha-1 Adrenergic Agonist and an Alpha-2 Adrenergic Antagonist" Jul. 1982, J. Pharmacol. Exp. Ther. 222(1):29-36.

Scholz "Imidazole Derivatives With Sympathomimetic Activity" Feb. 1, 1945, Ind. Eng. Chem. 37(2):120-125.

Shanler et al. "Successful Treatment of the Erythema and Flushing of Rosacea Using a Topically Applied Selective Alpha1 Adrenergic Receptor Agonist, Oxymetazoline" 2007 Arch Dermatol. 143(11): 1369-1371.

Stahl et al. "Handbook of Pharmaceutical Salts: Properties, Selection and Use" 2002, Int'l. Union of Pure and Applied Chemistry, pp. 324-325.

Su et al. "Blushing Propensity and Psychological Distress in People with Rosacea" 2012, Clin. Physcology and Psychotherapy 19:488-495.

Tan et al. "Rosacea and Migraine" Jan. 3, 1976, British Medical Journal 1 (6000):21.

Yamasaki "The Molecular Pathology of Rosacea" 2009, J. Dermatolog. Sci. 55:77-81.

Shanler et al. Successful Treatment of the Erythema and Flushing of Rosacea Using a Topically Applied Selective 1-Adrenergic Receptor Agonist, Oxymetazoline. Arch Dermatol. 2007; 143(11):1369-1371.

"Selective treatment of the erythema and flushing of rosacea using a topically applied selective alpha1 adrenergic receptor agonist, oxymetazoline" Feb. 1, 2008, J. Amer. Academy Dermatol. 58(2):AB9 (meeting abstract).

Pages 1,2, and 24-28 of Answer, Affirmative Defenses, and Counterclaims of Defendant Perrigo UK Finco Limited Partnership dated Apr. 27, 2021 in *EPI Health v. Perrigo UK Finco Limited Partnership*, Civil Action No. 21-cv-00498 (D. Del.).

PHARMACEUTICAL CREAM COMPOSITIONS OF OXYMETAZOLINE AND METHODS OF USE

CROSS-REFERENCE TO RELATED APPLICATIONS

This application is a continuation of U.S. patent application Ser. No. 16/267,590, filed Feb. 5, 2009, which is a continuation of U.S. patent application Ser. No. 14/144,106, filed Dec. 30, 2013, now abandoned, which is a continuation of U.S. application Ser. No. 13/396,165, filed Feb. 14, 2012, now abandoned, which claims the benefit of a U.S. Provisional Application Ser. No. 61/443,210, filed Feb. 15, 2011, each of which is incorporated by reference herein in its entirety.

BRIEF SUMMARY OF THE INVENTION

Embodiments may include a cream formulation of oxymetazoline. Embodiments may be directed to a cosmetically acceptable formulation comprising oxymetazoline and a pharmaceutically acceptable excipient, wherein the formulation is a cream. Embodiments may be directed to a formulation comprising oxymetazoline and a pharmaceutically acceptable excipient, wherein the formulation is a cream. Embodiments may be directed to a cream formulation comprising oxymetazoline in a therapeutically effective amount and a pharmaceutically acceptable excipient.

Embodiments may be directed to a method of treating telangiectasia comprising topical administration of a pharmaceutical composition comprising oxymetazoline and a pharmaceutically acceptable excipient. In some embodiments, a method of treating telangiectasia may comprise topically administering a pharmaceutical composition comprising a therapeutically effective amount of oxymetazoline and a pharmaceutically acceptable excipient. In some embodiments, a method of treating telangiectasia may comprise topically administering a pharmaceutical composition comprising a therapeutically effective amount of oxymetazoline and a pharmaceutically acceptable excipient in combination with an additional therapy directed toward the treatment of telangiectasias in order to provide additional additive or synergistic effect on the telangiectasias. In some embodiments, a method of treating telangiectasia may comprise topically administering a pharmaceutical composition comprising a therapeutically effective amount of oxymetazoline and a pharmaceutically acceptable excipient in combination with an additional therapy directed toward the treatment of the erythema, papules, pustules, phymas, epidermal barrier dysfunction, or other manifestation of *rosacea* in order to provide treatment of the telangiectasias.

Embodiments may be directed to a method of treating inflammatory lesions comprising topical administration of a pharmaceutical composition comprising oxymetazoline and a pharmaceutically acceptable excipient. In some embodiments, a method of treating inflammatory lesions may comprise topically administering a pharmaceutical composition comprising a therapeutically effective amount of oxymetazoline and a pharmaceutically acceptable excipient. In some embodiments, a method of treating inflammatory lesions may comprise topically administering a pharmaceutical composition comprising a therapeutically effective amount of oxymetazoline and a pharmaceutically acceptable excipient in combination with an additional therapy directed toward the treatment of inflammatory lesions in order to provide additional additive or synergistic effect on the inflammatory lesions. In some embodiments, a method of treating inflammatory lesions may comprise topically administering a pharmaceutical composition comprising a therapeutically effective amount of oxymetazoline and a pharmaceutically acceptable excipient in combination with an additional therapy directed toward the treatment of noninflammatory manifestations of *rosacea* such as telangiectasias, erythema, epidermal barrier dysfunction, or other manifestation of *rosacea* in order to provide treatment of both inflammatory and noninflammatory manifestations.

Embodiments may be directed to a method of treating two or more symptoms of *rosacea* selected from erythema, telangiectasia, or inflammatory lesions comprising topical administration of a pharmaceutical composition comprising oxymetazoline and a pharmaceutically acceptable excipient. In some embodiments, a method of treating two or more symptoms of *rosacea* selected from erythema, telangiectasia, or inflammatory lesions may comprise topically administering a pharmaceutical composition comprising a therapeutically effective amount of oxymetazoline and a pharmaceutically acceptable excipient.

Embodiments may be directed to a method of treating erythema, telangiectasia, and inflammatory lesions associated with *rosacea* comprising topical administration of a pharmaceutical composition comprising oxymetazoline and a pharmaceutically acceptable excipient. In some embodiments, a method of treating erythema, telangiectasia, and inflammatory lesions associated with *rosacea* may comprise topically administering a pharmaceutical composition comprising a therapeutically effective amount of oxymetazoline and a pharmaceutically acceptable excipient.

In some embodiments, the therapeutic effect of cream formulations described herein may be maintained for at least about 30 days, for at least 25 days, for at least 20 days, for at least 15 days, for at least 10 days after stopping the administration of the cream formulation. In some embodiments, the therapeutic effect may be maintained for at least about 7 days, for at least about 5 days, or for at least about 4 days after stopping the administration of the cream formulation.

Embodiments may be directed to a cream formulation comprising oxymetazoline in an amount of from about 0.0075% to about 5% by weight and pharmaceutically acceptable excipients. In some embodiments, the cream formulation may comprise oxymetazoline in an amount from about 0.01% to about 2% by weight. Embodiments may include one or more emulsifiers in a total amount of from about 1% to about 30% by weight of the pharmaceutical composition; and/or one or more emollients in a total amount of from about 1% to about 50% by weight of the pharmaceutical composition. In some embodiments, the formulation may further comprise additional additives selected from the group consisting of preservatives, emulsifiers, emulsion stabilizers, pH adjusters, chelating agents, viscosity modifiers, anti-oxidants, surfactants, emollients, opacifying agents, skin conditioners, buffers, and combinations thereof. In some embodiments, the formulation may further comprise a topically active pharmaceutical or cosmetic agent.

In certain embodiments, a cream comprising oxymetazoline, a vasoconstrictor and pharmaceutically acceptable excipients is provided. In certain embodiments, a cream comprising oxymetazoline, an alpha-adrenergic agonist and pharmaceutically acceptable excipients is provided. In certain embodiments, a cream comprising oxymetazoline, an imidazoline alpha-adrenergic agonist and pharmaceutically acceptable excipients is provided. In certain embodiments, a cream comprising oxymetazoline, a non-imidazoline alpha-adrenergic agonist and pharmaceutically acceptable excipients is provided. In certain embodiments, a cream comprising oxymetazoline, an alpha-1 adrenergic agonist and pharmaceutically acceptable excipients is provided. In certain embodiments, a cream comprising oxymetazoline, an alpha-2 adrenergic agonist and pharmaceutically acceptable excipients is provided. In certain embodiments, a cream comprising oxymetazoline, a selective alpha-adrenergic agonist and pharmaceutically acceptable excipients is provided. In certain embodiments, a cream comprising oxymetazoline, a non-selective alpha-adrenergic agonist and pharmaceutically acceptable excipients is provided. In certain embodiments, a cream comprising oxymetazoline, a selective alpha-1 adrenergic agonist and pharmaceutically acceptable excipients is provided. In certain embodiments, a cream comprising oxymetazoline, a selective alpha-2 adrenergic agonist and pharmaceutically acceptable excipients is provided. In certain embodiments, a cream comprising oxymetazoline, a non-selective alpha-1 adrenergic agonist and pharmaceutically acceptable excipients is provided. In certain embodiments, a cream comprising oxymetazoline, a non-selective alpha-2 adrenergic agonist and pharmaceutically acceptable excipients is provided.

In some embodiments, a method of treating a skin condition, including, but not limited to, *rosacea*, including, for example, erythematotelangiectatic *rosacea*, papulopustular *rosacea*, phymatous *rosacea*, ocular *rosacea* or combinations thereof; and symptoms associated with *rosacea*, including, for example, papules, pustules, phymas (skin thickening), telangiectasias or erythema associated with *rosacea*, other skin erythemas, telangiectasias, purpura or the like, and other manifestations associated therewith; other inflammatory conditions of the skin including, but not limited to, keratosis pilaris, lupus miliaris dissemniatus faciei, eczema, dermatitis, such as contact dermatitis, atopic dermatitis, seborrheic dermatitis, nummular dermatitis, generalized exfoliative dermatitis, statis dermatitis, neurodermatitis, *lichen simplex* chronicus, xerosis and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis *barbae*; disorders of sweat glands, such as *miliaria*, including, but not limited to, *miliaria crystallina, miliaria rubra, miliaria profunda, miliaria pustulosa*; sunburn, chronic actinic damage, *poikiloderma*, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma *annulare*; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses or inflammation due to any cause or combinations thereof comprising administering a cream formulation of embodiments described herein is provided.

DESCRIPTION OF DRAWINGS

For a fuller understanding of the nature and advantages of embodiments described herein, reference should be made to the following detailed description taken in connection with the accompanying drawings, in which.

DETAILED DESCRIPTION

Figure 1:
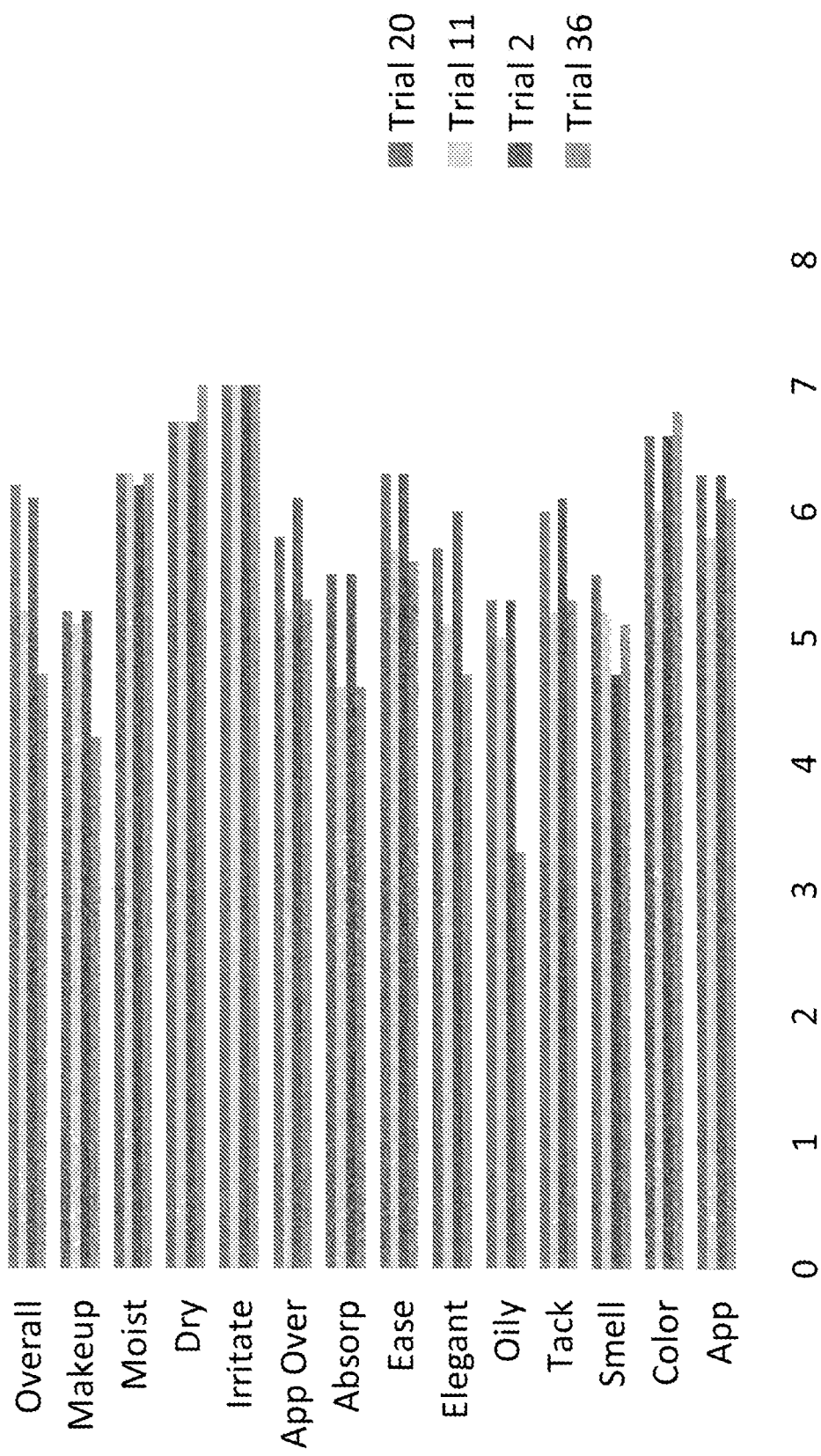
FIG. 1 is a bar graph showing the mean cosmetic acceptability scores including appearance and sensorial evaluation scores by category for creams of Trial 36, Trial 2, Trial 11 and Trial 20.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "preservative" is a reference to one or more preservatives and equivalents thereof known to those skilled in the art, and so forth.

As used herein, the term "about" means plus or minus 10% of the numerical value of the number with which it is being used. Therefore, about 50% means in the range of 45%-55%.

"Administering", when used in conjunction with a therapeutic, means to administer a therapeutic directly into or onto a target tissue or to administer a therapeutic to a subject, whereby the therapeutic positively impacts the tissue to which it is targeted. Thus, as used herein, the term "administering", when used in conjunction with a therapeutic, can include, but is not limited to, providing a therapeutic to a subject systemically by, for example, intravenous injection, whereby the therapeutic reaches the target tissue. Administering a composition or therapeutic may be accomplished by, for example, injection, oral administration, topical administration, or by these methods in combination with other known techniques. Such combination techniques may include heating, radiation, ultrasound and the use of delivery agents. Preferably, administering is a self-administration, wherein the therapeutic or composition is administered by the subject themselves. Alternatively, administering may be administration to the subject by a health care provider.

"Providing", when used in conjunction with a therapeutic, means to administer a therapeutic directly into or onto a target tissue, or to administer a therapeutic to a subject whereby the therapeutic positively impacts the tissue to which it is targeted.

The term "animal" as used herein includes, but is not limited to, humans and non-human vertebrates such as wild, domestic and farm animals.

The term "patient" or "subject" as used herein is an animal, particularly a human, suffering from an unwanted disease or condition that may be treated by the therapeutic and/or compositions described herein.

The term "improves" is used to convey that the present invention changes either the characteristics and/or the physical attributes of the tissue to which it is being provided, applied or administered. The term "improves" may also be used in conjunction with a diseased state such that when a diseased state is "improved" the symptoms or physical characteristics associated with the diseased state are diminished, reduced or eliminated.

The term "inhibiting" generally refers to prevention of the onset of the symptoms, alleviating the symptoms, or eliminating the disease, condition or disorder.

"Optional" or "optionally" means that the subsequently described event or circumstance may or may not occur, and that the description includes instances where the event occurs and instances where it does not.

As used herein, "room temperature" means an indoor temperature of from about 20° C. to about 25° C. (68 to 77° F.).

Throughout the specification of the application, various terms are used such as "primary," "secondary," "first," "second," and the like. These terms are words of convenience in order to distinguish between different elements, and such terms are not intended to be limiting as to how the different elements may be utilized.

By "pharmaceutically acceptable," "physiologically tolerable," and grammatical variations thereof, as they refer to compositions, carriers, diluents, and reagents or other ingredients of the formulation, can be used interchangeably and represent that the materials are capable of being administered without the production of undesirable physiological effects such as rash, burning, irritation or other deleterious effects to such a degree as to be intolerable to the recipient thereof.

As used herein, the term "cosmetically acceptable" and grammatical variations thereof, as they refer to compositions, carriers, diluents, and reagents or other ingredients of the formulation, represent that the materials used and final composition are not irritating or otherwise harmful to the patient in general and to the skin, in particular, and preferably are pleasant and well tolerated with respect to general appearance, pH, color, smell and texture (feel), that they are not, for example, unacceptably sticky (tacky), oily or drying, and that they do spread easily, absorb into the skin at an acceptable rate of absorption, and are generally moisturizing.

"Pharmaceutically acceptable salts" include both acid and base addition salts. "Pharmaceutically acceptable acid addition salt" refers to those salts that retain biological effectiveness and properties of the free bases and that include inorganic acids such as, for example, hydrochloric acid, hydrobromic acid, sulfuric acid, nitric acid, carbonic acid, phosphoric acid, and the like. Organic acids may be selected from aliphatic, cycloaliphatic, aromatic, araliphatic, heterocyclic, carboxylic, and sulfonic classes of organic acids, such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid, and the like.

As used herein, the term "therapeutic" means an agent utilized to treat, combat, ameliorate, prevent or improve an unwanted condition or disease of a subject. In part, embodiments of the present invention are directed to the treatment of various skin diseases, conditions or disorders or symptoms thereof, including, but not limited to, *rosacea* and symptoms associated with *rosacea*, including, for example, papules, pustules, phymas (skin thickening), telangiectasias or erythema associated with *rosacea*, other skin erythemas, telangiectasias, purpura or the like, and other manifestations associated therewith; other inflammatory conditions of the skin including, but not limited to, keratosis pilaris, lupus miliaris dissemniatus faciei, eczema, dermatitis, such as contact dermatitis, atopic dermatitis, seborrheic dermatitis, nummular dermatitis, generalized exfoliative dermatitis, statis dermatitis, neurodermatitis, *lichen simplex* chronicus, xerosis and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis *barbae*; disorders of sweat glands, such as *miliaria*, including, but not limited to, *miliaria crystallina, miliaria rubra, miliaria profunda, miliaria pustulosa*; sunburn, chronic actinic damage, *poikiloderma*, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma *annulare*; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses or inflammation due to any cause or combinations thereof.

The terms "therapeutically effective" or "effective", as used herein, may be used interchangeably and refer to an amount of a therapeutic composition of embodiments of the present invention (e.g., a composition comprising oxymetazoline). For example, a therapeutically effective amount of a composition is an amount of the composition, and particularly the active ingredient, such as oxymetazoline, that generally achieves the desired effect.

A "therapeutically effective amount" or "effective amount" of a composition is an amount necessary or sufficient to achieve the desired result. The activity contemplated by the embodiments herein includes medically therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. However, the effective amount administered can be determined by the practitioner or manufacturer or patient in light of the relevant circumstances including the condition to be treated, the choice of compound to be administered, and the chosen route of administration, and therefore, the above dosage ranges are not intended to limit the scope of the invention in any way. A therapeutically effective amount of the compound of embodiments herein is typically an amount such that when it is administered in a physiologically tolerable excipient composition, it is sufficient to achieve an effective systemic concentration or local concentration in or on the tissue to achieve the desired therapeutic or clinical outcome.

The terms "treat," "treated," or "treating" as used herein refers to therapeutic treatment and/or prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects.

As used herein, the term "consists of" or "consisting of" means that the formulation includes only the elements, steps, or ingredients specifically recited in the particular claimed embodiment or claim.

As used herein, the term "consisting essentially of" or "consists essentially of" means that the only active pharmaceutical ingredient in the formulation or method that treats the specified condition (e.g. erythema or redness associated with the particular disease to be treated) is the specifically recited therapeutic in the particular embodiment or claim.

Generally speaking, the term "tissue" refers to any aggregation of similarly specialized cells which are united in the performance of a particular function.

Rosacea is a chronic disease most commonly characterized by facial erythema (redness). There are at least four identified *rosacea* subtypes and patients may have more than one subtype present. The four most well recognized subtypes are erythematotelangiectatic *rosacea* (ETR); papulopustular *rosacea*; phymatous *rosacea*; and ocular *rosacea*. Other less common forms exist and the signs and symptoms of each subtype are not unique to that subtype and may overlap or coexist with any of the manifestations of any other subtype. ETR may be characterized by transient and/or permanent erythema with a tendency to flush and blush easily and telangiectasias, which in its milder form may resemble or present as erythema (redness) and in its more pronounced state may manifest as discrete visible blood vessels on the surface of the skin. Papulopustular *rosacea* may be characterized by transient and/or permanent erythema with papules (red bumps) and pustules (pus filled bumps). Without wishing to be bound by theory, though the papules and other inflammatory lesions (e.g. pustules) of papulopustular *rosacea* may be mistaken for acne, it is believed that the papules and pustules of *rosacea* are different from the papules and pustules of acne and arise from different underlying pathophysiologic processes. Phymatous *rosacea* may be characterized by thickening skin, irregular surface nodularities, enlargement of facial areas (e.g. nose and cheeks), erythema and telangiectasias. Ocular *rosacea* may be characterized by red, dry and irritated eyes and eyelids. In each subtype, erythema and telangiectasias of varying degree may be a feature.

Rosacea patients may need topical or oral (systemic) medication to alleviate their distress; however, a patient's skin may be so sensitive that many products are irritating and, in fact, may exacerbate the symptoms of *rosacea* and may cause more redness and discomfort than patients can tolerate. Thus, *rosacea* can be very difficult to effectively treat and thus may not only be physically distressing but also psychologically distressing. Accordingly, there is a need for a cosmetically and pharmaceutically acceptable therapeutic which addresses the myriad manifestations of *rosacea* including, but not limited to, the erythema or redness associated with *rosacea* and the telangiectasias associated with *rosacea*. Additionally, there is a need for a cosmetically and pharmaceutically acceptable therapeutic which addresses the inflammatory lesions and manifestations associated with *rosacea* including the papules, pustules and phymas (skin thickening).

As used herein, the term "erythema" refers to any redness of the skin due to hyperemia, congestion of the vasculature or dilation of the vasculature of the skin and its surrounding structures. Erythema may occur in many conditions of the skin including, but not limited to, *rosacea* and symptoms associated with *rosacea*, including, for example, papules, pustules, phymas (skin thickening), telangiectasias or erythema associated with *rosacea*, other skin erythemas, telangiectasias, purpura or the like, and other manifestations associated therewith; other inflammatory conditions of the skin including, but not limited to, keratosis pilaris, lupus miliaris dissemniatus faciei, eczema, dermatitis, such as contact dermatitis, atopic dermatitis, seborrheic dermatitis, nummular dermatitis, generalized exfoliative dermatitis, statis dermatitis, neurodermatitis, *lichen simplex* chronicus, xerosis and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis *barbae*; disorders of sweat glands, such as *miliaria*, including, but not limited to, *miliaria crystallina, miliaria rubra, miliaria profunda, miliaria pustulosa*; sunburn, chronic actinic damage, *poikiloderma*, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma *annulare*; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses; inflammation due to any cause or a combination thereof.

Keratosis pilaris (KP) is a very common genetic follicular condition that is manifested by the appearance of rough bumps on the skin and may be accompanied by erythema. Lupus *miliaris disseminatus* faciei (LMDF) is an uncommon, chronic dermatosis characterized by red-to-yellow or yellow-brown papules of the central face, particularly on and around the eyelids, that may be accompanied by erythema.

As used herein, the term "purpura" refers to any accumulation of blood in the skin due to vascular extravasation, irrespective of size or cause. As used herein, "purpura" refers to medical conditions commonly referred to as "petechiae" (pinpoint spots), "ecchymoses" (larger macular (flat) patches) and "purpura" (larger spots).

Purpura, in general, is hemorrhage of blood out of the vascular spaces and into the skin or surrounding tissues of the skin or mucous membranes. This hemorrhage results in a collection of blood in the dermis and/or subdermal tissues of the skin that is visible initially as a dark purple/red discoloration that changes color as it breaks down and is resorbed.

In particular, purpura can be characterized as flat (macular or non-palpable) or raised (palpable or papular). The definition of macular purpuric subtypes include: petechiae-defined as small purpura (less than 4-5 millimeters (mm) in diameter, purpura-defined as greater than 4-5 mm and less than 1 cm (centimeter) in diameter, and ecchymoses-defined as greater than 1 cm in diameter. The size divisions are not absolute but are useful rules of thumb and there is often a range in size of clinical purpuras in any one specific condition.

A bruise, also called a contusion or ecchymosis, is an injury to biological tissue in which blood vessels such as the capillaries are damaged, allowing blood to seep into the surrounding tissue(s). Bruising is usually caused by a blunt impact and its likelihood and its severity increases as one ages due to thinning and loss of elasticity of the skin.

There exists a need in the art for a topical pharmaceutical composition comprising oxymetazoline which is physically stable (i.e. without phase separation) and chemically stable with the active pharmaceutical agent and which optimizes the delivery of the oxymetazoline to the skin in such a manner as to effectively treat the pathologic condition. Therefore, embodiments herein are directed to pharmaceutical compositions formulated for topical administration of oxymetazoline. In certain embodiments, the pharmaceutical compositions may be creams, and such creams may have any number and quantity of additional components. Embodiments of the invention are directed at a cream formulation comprising oxymetazoline from about 0.0075% to about 5% and pharmaceutically acceptable excipients. Embodiments of the invention are directed at a cream formulation consisting essentially of oxymetazoline from about 0.0075% to about 5% and pharmaceutically acceptable excipients. Embodiments of the invention are directed at a cream formulation consisting of oxymetazoline from about 0.0075% to about 5% and pharmaceutically acceptable excipients. Such formulations may be used to treat *rosacea* and symptoms associated with *rosacea*, including, for example, papules, pustules, phymas (skin thickening), telangiectasias or erythema associated with *rosacea*, other skin erythemas, telangiectasias, purpura or the like, and other manifestations associated therewith; other inflammatory conditions of the skin including, but not limited to, keratosis pilaris, lupus *miliaris* dissemniatus faciei, eczema, dermatitis, such as contact dermatitis, atopic dermatitis, seborrheic dermatitis, nummular dermatitis, generalized exfoliative dermatitis, statis dermatitis, neurodermatitis, *lichen simplex* chronicus, *xerosis* and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis *barbae*; disorders of sweat glands, such as *miliaria*, including, but not limited to, *crystallina, miliaria rubra, miliaria profunda, miliaria pustulosa*; sunburn, chronic actinic damage, *poikiloderma*, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma *annulare*; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses, inflammation due to any cause or the like. Such formulations may be used to treat or prevent symptoms such as, but not limited to, papules, pustules, other inflammatory lesions, phymas (skin thickening), telangiectasias or erythema associated with *rosacea* and other inflammatory conditions of the skin including, but not limited to, keratosis pilaris, lupus *miliaris* dissemniatus faciei, eczema, dermatitis, such as contact dermatitis, atopic dermatitis, seborrheic dermatitis, nummular dermatitis, generalized exfoliative dermatitis, statis dermatitis, neurodermatitis, *lichen simplex* chronicus, *xerosis* and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis *barbae*; disorders of sweat glands, such as *miliaria*, including, but not limited to, *miliaria crystallina, miliaria* rubra, *miliaria* profunda, *miliaria pustulosa*; sunburn, chronic actinic damage, *poikiloderma*, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma *annulare*; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses or inflammation due to any cause and other skin conditions characterized by increased erythema of the skin. Such formulations may also be used to treat or prevent purpura, which is a hemorrhage of blood out of the vascular spaces and into the skin or surrounding tissues of the skin or mucous membranes. In further embodiments, the formulation is cosmetically acceptable.

In certain embodiments, as used herein, the term "telangiectasia" refers to a dilation of blood vessels, such as capillaries, arterioles and venules. In some embodiments, the dilated blood vessels may be clinically indistinguishable. A "clinically indistinguishable blood vessel" refers to a dilated blood vessel visually indiscernable to an observer without the aid of magnifying equipment (other than spectacles normally used by the observer). In some embodiments, the dilated blood vessels may be distinguishable. A "distinguishable blood vessel" refers to a dilated blood vessel visually discernable to an observer without the aid of magnifying equipment (other than spectacles normally used by the observer). In some embodiments, the telangiectasia may be permanent. A permanent telangiectasia may be one that is long-lasting, e.g. where the blood vessels remain dilated. In some embodiments, the telangiectasia may be transient. A transient telangiectasia may be one that lasts only for a short time or is impermanent. In certain embodiments, telangiectasias may be dilated blood vessels with a diameter of more than or equal to about 0.5 mm. In certain embodiments, telangiectasias may be dilated blood vessels with a diameter of about 0.5 mm to about 1 mm. In certain embodiments, telangiectasias may be dilated blood vessels with a diameter of less than about 0.5 mm. In certain embodiments, telangiectasias may be dilated blood vessels with a diameter of less than about 0.4 mm. In certain embodiments, telangiectasias may be dilated blood vessels with a diameter of less than about 0.3 mm. In certain embodiments, telangiectasias may be dilated blood vessels with a diameter of less than about 0.2 mm. In certain embodiments, telangiectasias may be dilated blood vessels with a diameter of less than about 0.1 mm. Telangiectasias can be associated with numerous conditions, syndromes, diseases and disorders. In some aspects, a telangiectasia can be associated with *rosacea*, while in certain alternative aspects, a telangiectasia can be a telangiectasia not associated with *rosacea*. In some embodiments, telangiectasia may include any telangiectasia. In some embodiments, a method of treating telangiectasia may comprise topical administration of a pharmaceutical composition comprising oxymetazoline and a pharmaceutically acceptable excipient. In some embodiments, a method of treating telangiectasia may comprise topically administering a pharmaceutical composition comprising a therapeutically effective amount of oxymetazoline and a pharmaceutically acceptable excipient. In some embodiments, a method of treating telangiectasia may comprise administering any formulation of embodiments herein. In some embodiments, the formulation for treating telangiectasia may comprise Trial 38 as the base formulation with oxymetazoline in a concentration of from about 0.0075% to about 5% by weight of the cream, including, for example, 0.01%, 0.06%, 0.10%, 0.15%, 0.5% or 5%, and pharmaceutically acceptable excipients. In some embodiments, the formulation for treating telangiectasia may consist of Trial 38 as the base formulation with oxymetazoline in a concentration of from about 0.0075% to about 5% by weight of the cream, including, for example, 0.01%, 0.06%, 0.10%, 0.15%, 0.5% or 5%, and pharmaceutically acceptable excipients. In some embodiments, the formulation for treating telangiectasia may consist essentially of Trial 38 as the base formulation with oxymetazoline in a concentration of from about 0.0075% to about 5% by weight of the cream, including, for example, 0.01%, 0.06%, 0.10%, 0.15%, 0.5% or 5%, and pharmaceutically acceptable excipients.

In some embodiments, a method of treating inflammatory lesions may comprise topical administration of a pharmaceutical composition comprising oxymetazoline and a pharmaceutically acceptable excipient. As used herein, "inflammatory lesions" may include papules, pustules, cysts or a combination thereof. In some embodiments, papules may be raised inflammatory lesions of less than about 0.5 cm in diameter with no purulent material. In some embodiments, pustules may be raised inflammatory lesions of less than about 0.5 cm in diameter with visible purulent material. In some embodiments, cysts may be any circumscribed, inflammatory mass greater than or equal to about 0.5 cm in diameter. In some embodiments, a method of treating inflammatory lesions may comprise topically administering a pharmaceutical composition comprising a therapeutically effective amount of oxymetazoline and a pharmaceutically acceptable excipient. In some embodiments, a method of treating inflammatory lesions may comprise administering any formulation of embodiments herein. In some embodiments, the formulation for treating inflammatory lesions may comprise Trial 38 as the base formulation with oxymetazoline in a concentration of from about 0.0075% to about 5% by weight of the cream, including, for example, 0.01%, 0.06%, 0.10%, 0.15%, 0.5% or 5%, and pharmaceutically acceptable excipients. In some embodiments, the formulation for treating inflammatory lesions may consist of Trial 38 as the base formulation with oxymetazoline in a concentration of from about 0.0075% to about 5% by weight of the cream, including, for example, 0.01%, 0.06%, 0.10%, 0.15%, 0.5% or 5%, and pharmaceutically acceptable excipients. In some embodiments, the formulation for treating inflammatory lesions may consist essentially of Trial 38 as the base formulation with oxymetazoline in a concentration of from about 0.0075% to about 5% by weight of the cream, including, for example, 0.01%, 0.06%, 0.10%, 0.15%, 0.5% or 5%, and pharmaceutically acceptable excipients.

In some embodiments, a method of treating two or more symptoms of *rosacea* selected from erythema, telangiectasia, or inflammatory lesions may comprise topical administration of a pharmaceutical composition comprising oxymetazoline and a pharmaceutically acceptable excipient. In some embodiments, a method of treating two or more symptoms of *rosacea* selected from erythema, telangiectasia, or inflammatory lesions may comprise topically administering a pharmaceutical composition comprising a therapeutically effective amount of oxymetazoline and a pharmaceutically acceptable excipient. In some embodiments, a method of treating two or more symptoms of *rosacea* selected from erythema, telangiectasia, or inflammatory lesions may comprise administering any formulation of embodiments herein. In some embodiments, the pharmaceutical composition for treating two or more symptoms of *rosacea* selected from erythema, telangiectasia, or inflammatory lesions may comprise Trial 38 as the base formulation with oxymetazoline in a concentration of from about 0.0075% to about 5% by weight of the cream, including, for example, 0.01%, 0.06%, 0.10%, 0.15%, 0.5% or 5%, and pharmaceutically acceptable excipients. In some embodiments, the pharmaceutical composition for treating two or more symptoms of *rosacea* selected from erythema, telangiectasia, or inflammatory lesions may consist of Trial 38 as the base formulation with oxymetazoline in a concentration of from about 0.0075% to about 5% by weight of the cream, including, for example, 0.01%, 0.06%, 0.10%, 0.15%, 0.5% or 5%, and pharmaceutically acceptable excipients. In some embodiments, the formulation for treating two or more symptoms of *rosacea* selected from erythema, telangiectasia, or inflammatory lesions may consist essentially of Trial 38 as the base formulation with oxymetazoline in a concentration of from about 0.0075% to about 5% by weight of the cream, including, for example, 0.01%, 0.06%, 0.10%, 0.15%, 0.5% or 5%, and pharmaceutically acceptable excipients.

In some embodiments, a method of treating erythema, telangiectasia, and inflammatory lesions associated with *rosacea* may comprise topical administration of a pharmaceutical composition comprising oxymetazoline and a pharmaceutically acceptable excipient. In some embodiments, a method of treating erythema, telangiectasia, and inflammatory lesions associated with *rosacea* may comprise topically administering a pharmaceutical composition comprising a therapeutically effective amount of oxymetazoline and a pharmaceutically acceptable excipient. In some embodiments, a method of treating erythema, telangiectasia, and inflammatory lesions associated with *rosacea* may comprise administering any formulation of embodiments herein. In some embodiments, the pharmaceutical composition treating erythema, telangiectasia, and inflammatory lesions associated with *rosacea* may comprise Trial 38 as the base formulation with oxymetazoline in a concentration of from about 0.0075% to about 5% by weight of the cream, including, for example, 0.01%, 0.06%, 0.10%, 0.15%, 0.5% or 5%, and pharmaceutically acceptable excipients. In some embodiments, the pharmaceutical composition for treating erythema, telangiectasia, and inflammatory lesions associated with *rosacea* may consist of Trial 38 as the base formulation with oxymetazoline in a concentration of from about 0.0075% to about 5% by weight of the cream, including, for example, 0.01%, 0.06%, 0.10%, 0.15%, 0.5% or 5%, and pharmaceutically acceptable excipients. In some embodiments, the formulation for treating erythema, telangiectasia, and inflammatory lesions associated with *rosacea* may consist essentially of Trial 38 as the base formulation with oxymetazoline in a concentration of from about 0.0075% to about 5% by weight of the cream, including, for example, 0.01%, 0.06%, 0.10%, 0.15%, 0.5% or 5%, and pharmaceutically acceptable excipients.

Further embodiments are directed to methods of treating erythema, redness or telangiectasias associated with *rosacea* comprising administering a cream comprising oxymetazoline in a therapeutically effective amount. Embodiments are directed to methods of treating papules, pustules, and other inflammatory lesions associated with *rosacea* comprising administering a cream comprising oxymetazoline in a therapeutically effective amount. Embodiments are directed to methods of treating skin erythema comprising administering a cream comprising oxymetazoline in a therapeutically effective amount. Embodiments are directed to methods of treating purpura comprising administering a cream comprising oxymetazoline in a therapeutically effective amount. Embodiments are directed to methods of treating keratosis pilaris, lupus *miliaris* disseminatus faciei or the like comprising administering a cream comprising oxymetazoline in a therapeutically effective amount. Embodiments are directed to methods of treating redness or erythema associated with *rosacea*, skin erythemas, telangiectasias, purpura or the like, and other manifestations associated therewith; other inflammatory conditions of the skin including, but not limited to, keratosis pilaris, lupus *miliaris* dissemniatus faciei, eczema, dermatitis, such as contact dermatitis, atopic dermatitis, seborrheic dermatitis, nummular dermatitis, generalized exfoliative dermatitis, statis dermatitis, neurodermatitis, *lichen simplex* chronicus, *xerosis* and xerotic dermatitis, dyshidrosis and dyshidrotic dermatitis, asteotic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis *barbae*; disorders of sweat glands, such as *miliaria*, including, but not limited to, *miliaria crystallina, miliaria* rubra, *miliaria* profunda, *miliaria pustulosa*; sunburn, chronic actinic damage, *poikiloderma*, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma *annulare*; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses, or inflammation due to any cause. In further embodiments, the formulation is cosmetically acceptable.

Embodiments of the invention are directed to methods of treating erythema or redness associated with *rosacea* comprising administering a cream comprising oxymetazoline in an amount from about 0.0075% to about 5% by weight of the cream and pharmaceutically acceptable excipients. Embodiments are directed to methods of treating inflammatory lesions including papules and pustules associated with *rosacea* comprising administering a cream comprising oxymetazoline in an amount from about 0.0075% to about 5% by weight of the cream and pharmaceutically acceptable excipients. Embodiments are directed to methods of treating skin thickening (phymas) associated with *rosacea* comprising administering a cream comprising oxymetazoline in an amount from about 0.0075% to about 5% by weight of the cream and pharmaceutically acceptable excipients. Some embodiments of the invention are directed to methods of treating erythema or redness associated with telangiectasia comprising administering a cream comprising oxymetazoline in an amount from about 0.0075% to about 5% by weight of the cream and pharmaceutically acceptable excipients. Some embodiments of the invention are directed to methods of treating telangiectasia comprising administering a cream comprising oxymetazoline in an amount from about 0.0075% to about 5% by weight of the cream and pharmaceutically acceptable excipients. Some embodiments of the invention are directed to methods of treating erythema or redness associated with erythemato-telangiectatic *rosacea* comprising administering a cream comprising oxymetazoline in an amount from about 0.0075% to about 5% by weight of the cream. Some embodiments of the invention are directed to methods of treating erythemato-telangiectatic *rosacea* comprising administering a cream comprising oxymetazoline in an amount from about 0.0075% to about 5% by weight of the cream and pharmaceutically acceptable excipients. Some embodiments of the invention are directed to methods of treating erythema or redness associated with papulopustular *rosacea* comprising administering a cream comprising oxymetazoline in an amount from about 0.0075% to about 5% by weight of the cream. Some embodiments of the invention are directed to methods of treating papules associated with papulopustular *rosacea* comprising administering a cream comprising oxymetazoline in an amount from about 0.0075% to about 5% by weight of the cream. Some embodiments of the invention are directed to methods of treating papulopustular *rosacea* comprising administering a cream comprising oxymetazoline in an amount from about 0.0075% to about 5% by weight of the cream and pharmaceutically acceptable excipients. Embodiments of the invention are directed to methods of treating symptoms associated with *rosacea* comprising administering a cream comprising oxymetazoline in an amount from about 0.0075% to about 5% by weight of the cream and pharmaceutically acceptable excipients, wherein the symptoms are selected from the group consisting of papules, pustules, erythema (redness), skin thickening and telangiectasias. Some embodiments of the invention are directed to methods of treating purpura comprising administering a cream comprising oxymetazoline in an amount from about 0.0075% to about 5% by weight of the cream and pharmaceutically acceptable excipients. Embodiments are directed to methods of treating keratosis pilaris, lupus *miliaris* disseminatus faciei or the like comprising administering a cream comprising oxymetazoline in an amount from about 0.0075% to about 5% by weight of the cream and pharmaceutically acceptable excipients. Embodiments are directed to methods of treating *rosacea* and symptoms associated with *rosacea*, including, for example, papules, pustules, phymas (skin thickening), telangiectasias or erythema associated with *rosacea*, other skin erythemas, telangiectasias, purpura or the like, and other manifestations associated therewith; other inflammatory conditions of the skin including, but not limited to, keratosis pilaris, lupus *miliaris* dissemniatus faciei, eczema, dermatitis, such as contact dermatitis, atopic dermatitis, seborrheic dermatitis, nummular dermatitis, generalized exfoliative dermatitis, statis dermatitis, neurodermatitis, *lichen simplex* chronicus, *xerosis* and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis *barbae*; disorders of sweat glands, such as *miliaria*, including, but not limited to, *miliaria crystallina, miliaria* rubra, *miliaria* profunda, *miliaria pustulosa*; sunburn, chronic actinic damage, *poikiloderma*, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma *annulare*; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses, inflammation due to any cause comprising administering a cream comprising oxymetazoline in an amount from about 0.0075% to about 5% by weight of the cream and pharmaceutically acceptable excipients. In further embodiments, the formulation is cosmetically acceptable.

Embodiments of the invention are directed to methods of treating erythema or redness associated with *rosacea* comprising administering a cream consisting of oxymetazoline in an amount from about 0.0075% to about 5% by weight of the cream and pharmaceutically acceptable excipients. Embodiments are directed to methods of treating papules associated with *rosacea* comprising administering a cream consisting of oxymetazoline in an amount from about 0.0075% to about 5% by weight of the cream and pharmaceutically acceptable excipients. Embodiments of the invention are directed to methods of treating symptoms associated with *rosacea* comprising administering a cream consisting of oxymetazoline in an amount from about 0.0075% to about 5% by weight of the cream and pharmaceutically acceptable excipients, wherein the symptoms are selected from the group consisting of papules, pustules, erythema (redness), skin thickening, and telangiectasias. Some embodiments of the invention are directed to methods of treating erythema or redness associated with telangiectasia comprising administering a cream consisting of oxymetazoline in an amount from about 0.0075% to about 5% by weight of the cream and pharmaceutically acceptable excipients. Some embodiments of the invention are directed to methods of treating telangiectasia comprising administering a cream consisting of oxymetazoline in an amount from about 0.0075% to about 5% by weight of the cream and pharmaceutically acceptable excipients. Some embodiments of the invention are directed to methods of treating erythema or redness associated with erythemato-telangiectatic *rosacea* comprising administering a cream consisting of oxymetazoline in an amount from about 0.0075% to about 5% by weight of the cream and pharmaceutically acceptable excipients. Some embodiments of the invention are directed to methods of treating erythemato-telangiectatic *rosacea* comprising administering a cream consisting of oxymetazoline in an amount from about 0.0075% to about 5% by weight of the cream and pharmaceutically acceptable excipients. Some embodiments of the invention are directed to methods of treating erythema or redness associated with papulopustular *rosacea* comprising administering a cream consisting of oxymetazoline in an amount from about 0.0075% to about 5% by weight of the cream. Some embodiments of the invention are directed to methods of treating papules or pustules associated with papulopustular *rosacea* comprising administering a cream consisting of oxymetazoline in an amount from about 0.0075% to about 5% by weight of the cream. Some embodiments of the invention are directed to methods of treating papulopustular *rosacea* comprising administering a cream consisting of oxymetazoline in an amount from about 0.0075% to about 5% by weight of the cream and pharmaceutically acceptable excipients. Some embodiments of the invention are directed to methods of treating purpura comprising administering a cream consisting of oxymetazoline in an amount from about 0.0075% to about 5% by weight of the cream and pharmaceutically acceptable excipients. Embodiments are directed to methods of treating *rosacea* and symptoms associated with *rosacea*, including, for example, papules, pustules, phymas (skin thickening), telangiectasias or erythema associated with *rosacea*, other skin erythemas, telangiectasias, purpura or the like, and other manifestations associated therewith; other inflammatory conditions of the skin including, but not limited to, keratosis pilaris, lupus *miliaris* dissemniatus faciei, eczema, dermatitis, such as contact dermatitis, atopic dermatitis, seborrheic dermatitis, nummular dermatitis, generalized exfoliative dermatitis, statis dermatitis, neurodermatitis, *lichen simplex* chronicus, *xerosis* and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis *barbae*; disorders of sweat glands, such as *miliaria*, including, but not limited to, *miliaria crystallina, miliaria* rubra, *miliaria* profunda, *miliaria pustulosa*; sunburn, chronic actinic damage, *poikiloderma*, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma *annulare*; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses, inflammation due to any cause comprising administering a cream consisting of oxymetazoline in an amount from about 0.0075% to about 5% by weight of the cream and pharmaceutically acceptable excipients. In further embodiments, the formulation is cosmetically acceptable.

Embodiments of the invention are directed to methods of treating erythema or redness associated with *rosacea* comprising administering a cream consisting essentially of oxymetazoline in an amount from about 0.0075% to about 5% by weight of the cream and pharmaceutically acceptable excipients. Embodiments are directed to methods of treating papules associated with *rosacea* comprising administering a cream consisting essentially of oxymetazoline in an amount from about 0.0075% to about 5% by weight of the cream and pharmaceutically acceptable excipients. Embodiments of the invention are directed to methods of treating symptoms associated with *rosacea* comprising administering a cream consisting essentially of oxymetazoline in an amount from about 0.0075% to about 5% by weight of the cream and pharmaceutically acceptable excipients, wherein the symptoms are selected from the group consisting of papules, pustules, erythema (redness), skin thickening, and telangiectasias. Some embodiments of the invention are directed to methods of treating erythema or redness associated with telangiectasia comprising administering a cream consisting essentially of oxymetazoline in an amount from about 0.0075% to about 5% by weight of the cream and pharmaceutically acceptable excipients. Some embodiments of the invention are directed to methods of treating telangiectasia comprising administering a cream consisting essentially of oxymetazoline in an amount from about 0.0075% to about 5% by weight of the cream and pharmaceutically acceptable excipients. Some embodiments of the invention are directed to methods of treating erythema or redness associated with erythemato-telangiectatic *rosacea* comprising administering a cream consisting essentially of oxymetazoline in an amount from about 0.0075% to about 5% by weight of the cream and pharmaceutically acceptable excipients. Some embodiments of the invention are directed to methods of treating erythemato-telangiectatic *rosacea* comprising administering a cream consisting essentially of oxymetazoline in an amount from about 0.0075% to about 5% by weight of the cream and pharmaceutically acceptable excipients. Some embodiments of the invention are directed to methods of treating erythema or redness associated with papulopustular *rosacea* comprising administering a cream consisting essentially of oxymetazoline in an amount from about 0.0075% to about 5% by weight of the cream. Some embodiments of the invention are directed to methods of treating papules or pustules associated with papulopustular *rosacea* comprising administering a cream consisting essentially of oxymetazoline in an amount from about 0.0075% to about 5% by weight of the cream. Some embodiments of the invention are directed to methods of treating papulopustular *rosacea* comprising administering a cream consisting essentially of oxymetazoline in an amount from about 0.0075% to about 5% by weight of the cream and pharmaceutically acceptable excipients. Some embodiments of the invention are directed to methods of treating purpura comprising administering a cream consisting of oxymetazoline in an amount from about 0.0075% to about 5% by weight of the cream and pharmaceutically acceptable excipients. Embodiments are directed to methods of treating keratosis pilaris, lupus *miliaris* disseminatus faciei or the like comprising administering a cream consisting essentially of oxymetazoline in an amount from about 0.0075% to about 5% by weight of the cream and pharmaceutically acceptable excipients. Embodiments are directed to methods of treating *rosacea* and symptoms associated with *rosacea*, including, for example, papules, pustules, phymas (skin thickening), telangiectasias or erythema associated with *rosacea*, other skin erythemas, telangiectasias, purpura or the like, and other manifestations associated therewith; other inflammatory conditions of the skin including, but not limited to, keratosis pilaris, lupus *miliaris* dissemniatus faciei, eczema, dermatitis, such as contact dermatitis, atopic dermatitis, seborrheic dermatitis, nummular dermatitis, generalized exfoliative dermatitis, statis dermatitis, neurodermatitis, *lichen simplex* chronicus, *xerosis* and xerotic dermatitis, dyshidrosis and dyshidrotic dermatitis, asteotic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis *barbae*; disorders of sweat glands, such as *miliaria*, including, but not limited to, *miliaria crystallina*, *miliaria* rubra, *miliaria* profunda, *miliaria pustulosa*; sunburn, chronic actinic damage, *poikiloderma*, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma *annulare*; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses, inflammation due to any cause comprising administering a cream consisting essentially of oxymetazoline in an amount from about 0.0075% to about 5% by weight of the cream and pharmaceutically acceptable excipients. In further embodiments, the formulation is cosmetically acceptable.

Oxymetazoline is the common name for 3-(4,5-dihydro-1H-imidazol-2-ylmethyl)-2,4-dimethyl-6-tert-butyl-phenol, which has the chemical structure:

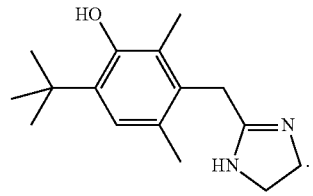 [SMILES: Cc1cc(C(C)(C)C)c(O)c(C)c1CC1=NCCN1]

As used herein, oxymetazoline includes both oxymetazoline free base and an acid addition salt of oxymetazoline. For example, in some embodiments, the oxymetazoline used in the preparation of the pharmaceutical composition may include a pharmaceutical salt, such as hydrochloric acid, hydrobromic acid, sulfuric acid, nitric acid, carbonic acid, phosphoric acid, and the like, or an organic acid such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid, and the like. In certain embodiments, the pharmaceutical salt may be hydrochloric acid A "cream," as used herein, refers to a semi-solid emulsion, i.e. a dispersed system having at least two immiscible phases where one phase is dispersed in another, with droplets ranging in diameter from about 0.1 µm to about 100 µm that is capable of penetrating the stratum corneum layer of skin. The creams of various embodiments can have a viscosity of from about 2,500 centipoises (cP) to about 150,000 cP at about 25° C. In some embodiments, the creams described herein can exhibit a melting point of greater than about 25° C., greater than about 30° C., greater than about 35° C., greater than about 40° C., from about 25° C. to about 80° C., from about 25° C. to about 60° C., from about 30° C. to about 80° C., from about 30° C. to about 60° C., from about 35° C. to about 80° C., from about 35° C. to about 60° C., from about 35° C. to about 50° C., from about 35° C. to about 40° C., from about 40° C. to about 80° C., or from about 40° C. to about 60° C.

In embodiments, a cream comprising oxymetazoline, as the active pharmaceutical ingredient (API), and pharmaceutically acceptable excipients is provided. In some embodiments, the cream may comprise from about 0.0075% to about 5%, from about 0.0075% to about 2.5%, from about 0.0075% to about 2%, from about 0.0075% to about 1%, from about 0.0075% to about 0.5%, from about 0.0075% to about 0.25%, from about 0.0075% to about 0.15%, from about 0.0075% to about 0.1%, from about 0.0075% to about 0.025%, from about 0.0075% to about 0.075%, from about 0.0075% to about 0.06%, from about 0.0075% to about 0.05%, from about 0.01% to about 5%, from about 0.01% to about 2.5%, from about 0.01% to about 2%, from about 0.01% to about 1%, from about 0.01% to about 0.5%, from about 0.01% to about 0.25%, from about 0.01% to about 0.15%, from about 0.01% to about 0.1%, from about 0.01% to about 0.025%, from about 0.05% to about 5%, from about 0.05% to about 2.5%, from about 0.05% to about 2%, from about 0.05% to about 1%, from about 0.05% to about 0.5%, from about 0.05% to about 0.25%, from about 0.05% to about 0.15%, from about 0.05% to about 0.1%, from about 0.05% to about 0.075% from about 0.1% to about 5%, from about 0.1% to about 2.5%, from about 0.1% to about 2%, from about 0.1% to about 1%, from about 0.1% to about 0.5%, from about 0.1% to about 0.25%, from about 0.1% to about 0.15%, from about 0.15% to about 5%, from about 0.15% to about 2.5%, from about 0.15% to about 2%, from about 0.15% to about 1%, from about 0.15% to about 0.5%, from about 0.15% to about 0.25% by weight of oxymetazoline and pharmaceutically acceptable excipients. In some embodiments, the cream may comprise about 0.0075%, about 0.01%, about 0.025%, about 0.05%, about 0.06%, about 0.075%, about 0.1%, about 0.15%, about 0.2%, about 0.25%, about 0.3%, about 0.35%, about 0.4%, about 0.45%, about 0.5%, about 0.75%, about 1%, about 2%, about 2.5% or about 5% by weight of oxymetazoline and pharmaceutically acceptable excipients. In some embodiments, the cream may comprise less than about 5% by weight of oxymetazoline and pharmaceutically acceptable excipients. In some embodiments, the cream may comprise less than about 2.5% by weight of oxymetazoline and pharmaceutically acceptable excipients. In some embodiments, the cream may comprise less than about 2% by weight of oxymetazoline and pharmaceutically acceptable excipients. In some embodiments, the cream may comprise less than about 1% by weight of oxymetazoline and pharmaceutically acceptable excipients. In certain embodiments, a cream comprising oxymetazoline, a vasoconstrictor and pharmaceutically acceptable excipients is provided. In certain embodiments, a cream comprising oxymetazoline, an alpha-adrenergic agonist and pharmaceutically acceptable excipients is provided. In certain embodiments, a cream comprising oxymetazoline, an imidazoline alpha-adrenergic agonist and pharmaceutically acceptable excipients is provided. In certain embodiments, a cream comprising oxymetazoline, a non-imidazoline alpha-adrenergic agonist and pharmaceutically acceptable excipients is provided. In certain embodiments, a cream comprising oxymetazoline, an alpha-1 adrenergic agonist and pharmaceutically acceptable excipients is provided. In certain embodiments, a cream comprising oxymetazoline, an alpha-2 adrenergic agonist and pharmaceutically acceptable excipients is provided. In certain embodiments, a cream comprising oxymetazoline, a selective alpha-adrenergic agonist and pharmaceutically acceptable excipients is provided. In certain embodiments, a cream comprising oxymetazoline, a non-selective alpha-adrenergic agonist and pharmaceutically acceptable excipients is provided. In certain embodiments, a cream comprising oxymetazoline, a selective alpha-1 adrenergic agonist and pharmaceutically acceptable excipients is provided. In certain embodiments, a cream comprising oxymetazoline, a selective alpha-2 adrenergic agonist and pharmaceutically acceptable excipients is provided. In certain embodiments, a cream comprising oxymetazoline, a non-selective alpha-1 adrenergic agonist and pharmaceutically acceptable excipients is provided. In certain embodiments, a cream comprising oxymetazoline, a non-selective alpha-2 adrenergic agonist and pharmaceutically acceptable excipients is provided.

In embodiments of the present invention a cream consisting essentially of oxymetazoline and pharmaceutically acceptable excipients is provided. In some embodiments, the cream may consist essentially of from about 0.0075% to about 5%, from about 0.0075% to about 2.5%, from about 0.0075% to about 2%, from about 0.0075% to about 1%, from about 0.0075% to about 0.5%, from about 0.0075% to about 0.25%, from about 0.0075% to about 0.15%, from about 0.0075% to about 0.1%, from about 0.0075% to about 0.025%, from about 0.0075% to about 0.075%, from about 0.0075% to about 0.06%, from about 0.0075% to about 0.05%, from about 0.01% to about 5%, from about 0.01% to about 2.5%, from about 0.01% to about 2%, from about 0.01% to about 1%, from about 0.01% to about 0.5%, from about 0.01% to about 0.25%, from about 0.01% to about 0.15%, from about 0.01% to about 0.1%, from about 0.01% to about 0.025%, from about 0.05% to about 5%, from about 0.05% to about 2.5%, from about 0.05% to about 2%, from about 0.05% to about 1%, from about 0.05% to about 0.5%, from about 0.05% to about 0.25%, from about 0.05% to about 0.15%, from about 0.05% to about 0.1%, from about 0.05% to about 0.075% from about 0.1% to about 5%, from about 0.1% to about 2.5%, from about 0.1% to about 2%, from about 0.1% to about 1%, from about 0.1% to about 0.5%, from about 0.1% to about 0.25%, from about 0.1% to about 0.15%, from about 0.15% to about 5%, from about 0.15% to about 2.5%, from about 0.15% to about 2%, from about 0.15% to about 1%, from about 0.15% to about 0.5%, from about 0.15% to about 0.25% by weight of oxymetazoline and pharmaceutically acceptable excipients. In some embodiments, the cream may consist essentially of about 0.0075%, about 0.01%, about 0.025%, about 0.05%, about 0.06%, about 0.075%, about 0.1%, about 0.15%, about 0.2%, about 0.25%, about 0.3%, about 0.35%, about 0.4%, about 0.45%, about 0.5%, about 0.75%, about 1%, about 2%, about 2.5% or about 5% by weight of oxymetazoline and pharmaceutically acceptable excipients. In some embodiments, the cream may consist essentially of less than about 5% by weight of oxymetazoline and pharmaceutically acceptable excipients. In some embodiments, the cream may consist essentially of less than about 2.5% by weight of oxymetazoline and pharmaceutically acceptable excipients. In some embodiments, the cream may consist essentially of less than about 2% by weight of oxymetazoline and pharmaceutically acceptable excipients. In some embodiments, the cream may consist essentially of less than about 1% by weight of oxymetazoline and pharmaceutically acceptable excipients. In certain embodiments, a cream consisting essentially of oxymetazoline, a vasoconstrictor and pharmaceutically acceptable excipients is provided. In certain embodiments, a cream consisting essentially of oxymetazoline, an alpha-adrenergic agonist and pharmaceutically acceptable excipients is provided. In certain embodiments, a cream consisting essentially of oxymetazoline, an imidazoline alpha-adrenergic agonist and pharmaceutically acceptable excipients is provided. In certain embodiments, a cream consisting essentially of oxymetazoline, a non-imidazoline alpha-adrenergic agonist and pharmaceutically acceptable excipients is provided. In certain embodiments, a cream consisting essentially of oxymetazoline, an alpha-1 adrenergic agonist and pharmaceutically acceptable excipients is provided. In certain embodiments, a cream consisting essentially of oxymetazoline, an alpha-2 adrenergic agonist and pharmaceutically acceptable excipients is provided. In certain embodiments, a cream consisting essentially of oxymetazoline, a selective alpha-adrenergic agonist and pharmaceutically acceptable excipients is provided. In certain embodiments, a cream consisting essentially of oxymetazoline, a non-selective alpha-adrenergic agonist and pharmaceutically acceptable excipients is provided. In certain embodiments, a cream consisting essentially of oxymetazoline, a selective alpha-1 adrenergic agonist and pharmaceutically acceptable excipients is provided. In certain embodiments, a cream consisting essentially of oxymetazoline, a selective alpha-2 adrenergic agonist and pharmaceutically acceptable excipients is provided. In certain embodiments, a cream consisting essentially of oxymetazoline, a non-selective alpha-1 adrenergic agonist and pharmaceutically acceptable excipients is provided. In certain embodiments, a cream consisting essentially of oxymetazoline, a non-selective alpha-2 adrenergic agonist and pharmaceutically acceptable excipients is provided.

In embodiments of the present invention a cream consisting of oxymetazoline and pharmaceutically acceptable excipients is provided. In some embodiments, the cream may consist of from about 0.0075% to about 5%, from about 0.0075% to about 2.5%, from about 0.0075% to about 2%, from about 0.0075% to about 1%, from about 0.0075% to about 0.5%, from about 0.0075% to about 0.25%, from about 0.0075% to about 0.15%, from about 0.0075% to about 0.1%, from about 0.0075% to about 0.025%, from about 0.0075% to about 0.075%, from about 0.0075% to about 0.06%, from about 0.0075% to about 0.05%, from about 0.01% to about 5%, from about 0.01% to about 2.5%, from about 0.01% to about 2%, from about 0.01% to about 1%, from about 0.01% to about 0.5%, from about 0.01% to about 0.25%, from about 0.01% to about 0.15%, from about 0.01% to about 0.1%, from about 0.01% to about 0.025%, from about 0.05% to about 5%, from about 0.05% to about 2.5%, from about 0.05% to about 2%, from about 0.05% to about 1%, from about 0.05% to about 0.5%, from about 0.05% to about 0.25%, from about 0.05% to about 0.15%, from about 0.05% to about 0.1%, from about 0.05% to about 0.075% from about 0.1% to about 5%, from about 0.1% to about 2.5%, from about 0.1% to about 2%, from about 0.1% to about 1%, from about 0.1% to about 0.5%, from about 0.1% to about 0.25%, from about 0.1% to about 0.15%, from about 0.15% to about 5%, from about 0.15% to about 2.5%, from about 0.15% to about 2%, from about 0.15% to about 1%, from about 0.15% to about 0.5%, from about 0.15% to about 0.25% by weight of oxymetazoline and pharmaceutically acceptable excipients. In some embodiments, the cream may consist of about 0.0075%, about 0.01%, about 0.025%, about 0.05%, about 0.06%, about 0.075%, about 0.1%, about 0.15%, about 0.2%, about 0.25%, about 0.3%, about 0.35%, about 0.4%, about 0.45%, about 0.5%, about 0.75%, about 1%, about 2%, about 2.5% or about 5% by weight of oxymetazoline and pharmaceutically acceptable excipients. In some embodiments, the cream may consist of less than about 5% by weight of oxymetazoline and pharmaceutically acceptable excipients. In some embodiments, the cream may consist of less than about 2.5% by weight of oxymetazoline and pharmaceutically acceptable excipients. In some embodiments, the cream may consist of less than about 2% by weight of oxymetazoline and pharmaceutically acceptable excipients. In some embodiments, the cream may consist of less than about 1% by weight of oxymetazoline and pharmaceutically acceptable excipients. In certain embodiments, a cream consisting of oxymetazoline, a vasoconstrictor and pharmaceutically acceptable excipients is provided. In certain embodiments, a cream consisting of oxymetazoline, an adrenomimetic and pharmaceutically acceptable excipients is provided. In certain embodiments, a cream consisting of oxymetazoline, an alpha-adrenergic agonist and pharmaceutically acceptable excipients is provided. In certain embodiments, a cream consisting of oxymetazoline, an imidazoline alpha-adrenergic agonist and pharmaceutically acceptable excipients is provided. In certain embodiments, a cream consisting of oxymetazoline, a non-imidazoline alpha-adrenergic agonist and pharmaceutically acceptable excipients is provided. In certain embodiments, a cream consisting of oxymetazoline, an alpha-1 adrenergic agonist and pharmaceutically acceptable excipients is provided. In certain embodiments, a cream consisting of oxymetazoline, an alpha-2 adrenergic agonist and pharmaceutically acceptable excipients is provided. In certain embodiments, a cream consisting of oxymetazoline, a selective alpha-adrenergic agonist and pharmaceutically acceptable excipients is provided. In certain embodiments, a cream consisting of oxymetazoline, a non-selective alpha-adrenergic agonist and pharmaceutically acceptable excipients is provided. In certain embodiments, a cream consisting of oxymetazoline, a selective alpha-1 adrenergic agonist and pharmaceutically acceptable excipients is provided. In certain embodiments, a cream consisting of oxymetazoline, a selective alpha-2 adrenergic agonist and pharmaceutically acceptable excipients is provided. In certain embodiments, a cream consisting of oxymetazoline, a non-selective alpha-1 adrenergic agonist and pharmaceutically acceptable excipients is provided. In certain embodiments, a cream consisting of oxymetazoline, a non-selective alpha-2 adrenergic agonist and pharmaceutically acceptable excipients is provided.

In an embodiment, the cream may comprise a formulation having a buffer system. In an embodiment, the cream may comprise a buffering agent. In some embodiments, the buffering agent may be selected from a group consisting of citric acid, sodium citrate, sodium lactate, ammonium hydroxide, trizma acetate, sodium borate, acetic acid, sodium acetate, phosphoric acid, sodium phosphate, sodium citrate dehydrate and the like.

In an embodiment of the present invention, the cream may comprise the formulation of any of Trials 22, 24, 25, or 35-51 as described herein. In one embodiment of the present invention, the cream consists essentially of the formulation of any of Trials 22, 24, 25, or 35-51 as described herein. In one embodiment of the present invention, the cream consists of the formulation of any of Trials 22, 24, 25, or 35-51 as described herein. In an embodiment of the present invention, the cream may comprise the formulation of Trial 38 as the base formulation with oxymetazoline and a pharmaceutically acceptable excipient as described herein. In one embodiment of the present invention, the cream consists essentially of the formulation of Trial 38 as the base formulation with oxymetazoline and a pharmaceutically acceptable excipient as described herein. In one embodiment of the present invention, the cream consists of the formulation of Trial 38 as the base formulation with oxymetazoline and a pharmaceutically acceptable excipient as described herein. In such embodiments, oxymetazoline may be present at a concentration of from about 0.0075% to about 5% by weight of the cream.

In some embodiments, the oxymetazoline cream may include an emulsifying agent, or emulsifier. The emulsifier can be provided to adjust the properties of the cream, such as density, viscosity, the melting point, and/or droplet size; and in some embodiments, the emulsifier may increase the stability of the cream. Various emulsions suitable for embodiments described herein and methods for preparing such emulsions are well known in the art and are described in, for example, Remington's Pharmaceutical Sciences, Mack Publishing Co., Easton, Pa., USA, which is hereby incorporated by reference in its entirety. In some embodiments, the cream may include an emulsifier in an amount from about 1% to about 30%, from about 1% to about 25%, from about 1% to about 20%, or from about 4% to about 12% emulsifier. In some embodiments, the cream may include emulsifier in an amount greater than 8%. In some embodiments, the cream may include from about 8% to about 30% emulsifier. In some embodiments, the cream may include from about 8% to about 25% emulsifier. In other embodiments, the cream may include from about 8% to about 20% emulsifier. In still other embodiments, the cream may include from about 8% to about 10% emulsifier. If more than one emulsifier is used, the cream may include from about 1% to about 30% of each emulsifier, from about 2% to about 30% of each emulsifier or from about 2% to about 25% of each emulsifier.

The creams of various embodiments may include any emulsifiers or combination of emulsifiers. For example, in some embodiments, the cream may be a common oil-in-water or water-in-oil emulsion including oxymetazoline and water or one or more common oils such as, for example, cottonseed, groundnut, corn, germ, olive, castor, soybean, mineral, and sesame oils. In other embodiments, the cream may include one or more emulsifiers, such as, for example, sesquioleates such as sorbitan sesquioleate or polyglyceryl-2-sesquioleate, ethoxylated esters of derivatives of natural oils such as the polyethoxylated ester of hydrogenated castor oil, silicone emulsifiers such as silicone polyols, anionic emulsifiers, fatty acid soaps such as potassium stearate and fatty acid sulphates like sodium cetostearyl sulphate, ethoxylated fatty alcohols, sorbitan esters, ethoxylated sorbitan esters, ethoxylated fatty acid esters such as ethoxylated stearates, ethoxylated mono, di-, and triglycerides, non-ionic self-emulsifying waxes, ethoxylated fatty acids, methylglucose esters such as polyglycerol-3 methyl glucose distearate, and mixtures thereof. In particular embodiments, the emulsifier may be an ethoxylated fatty acid such as, for example, the mixture of PEG-6/PEG-32/glycol stearate marketed under the trademark TEFOSE™ 63 by Gattefosse. As used herein, TEFOSE™ 63 is considered an emulsifier and, in certain embodiments described herein, shall be considered a mixture of one or more polyethylene glycol (PEG) stearates and one or more glycol stearates. In some embodiments, the emulsifier may comprise a polyethylene glycol (PEG) stearate, a glycol stearate or a mixture thereof. In some embodiments, the cream may include from about 1% to about 30% TEFOSE™ 63. In some embodiments, the cream may include from about 1% to about 20% TEFOSE™ 63. In other embodiments, the cream may include from about 1% to less than about 20% TEFOSE™ 63. In embodiments, the cream may include from about 4% to about 12% TEFOSE™ 63. In some embodiments, the cream may include greater than about 8% TEFOSE™ 63. In other embodiments, the cream may include from about 8% to about 10% TEFOSE™. In still other embodiments, the cream may include from about 8% to less than about 10% TEFOSE™ 63. In some embodiments, the cream may comprise TEFOSE™ 63 in an amount from about 1% to about 20%. In various embodiments, the cream may comprise TEFOSE™ 63 in an amount from about 3% to about 15%, from about 5% to about 10%, from about 7% to about 10%, about 9% or about 8%. In certain embodiments, TEFOSE™ 63 is comprised of PEG-6 stearate, glycol stearate, and PEG-32 stearate. In embodiments, the cream comprises PEG-6 stearate, glycol stearate, and PEG-32 stearate added as TEFOSE™ 63 in an about from about 1% to about 20%, from about 3% to about 15%, from about 5% to about 10%, from about 7% to about 10%, about 9% or about 8%. In some embodiments, the cream comprises PEG-6 stearate, glycol stearate and PEG-32 stearate. In embodiments, the cream may comprise PEG-6 stearate, glycol stearate and PEG-32 stearate in a ratio of about 63:18.5:18.5, about 75:12.5:12.5, about 50:25:25, about 75:15:10 or ranges of such ratios. In embodiments, the cream may comprise PEG-6 stearate, glycol stearate and PEG-32 stearate in a combined amount of from about 1% to about 30%, from about 1% to about 20%, from about 3% to about 15%, from about 5% to about 10%, from about 7% to about 10%, about 9% or about 8%. In embodiments, the cream may comprise PEG-6 stearate in an about from about 1% to about 20% by weight, from about 1% to about 10% by weight, from about 4% to about 10% by weight or from about 4% to about 6% by weight. In some embodiments, the cream may comprise glycol stearate in an amount from about 0.1% to about 10%, from about 0.1% to about 8%, from about 0.5% to about 5%, from about 0.5% to about 3%, from about 0.5% to about 2%, or from about 0.8% to about 2%. In some embodiments, the cream may comprise PEG-32 stearate in an amount from about 0.1% to about 10%, from about 0.1% to about 8%, from about 0.5% to about 5%, from about 0.5% to about 3%, from about 0.5% to about 2%, or from about 0.8% to about 2%. In some embodiments, the cream may comprise PEG-6 may be present in an amount of about 5% w/w; glycol stearate may be present in an amount of about 1.5% w/w, PEG-32 stearate may be present in an amount of about 1.5% w/w.

In some embodiments, the hydrophilic-lipophilic balance ("HLB") of the oil phase (or internal phase) of the cream may be very closely matched with the HLB values of the blend of emulsifiers in the cream. For example, the ingredients in the oil phase may include HLB values of:

| Ingredient | HLB value* |
|---|---|
| Medium chain triglycerides | 10.0 |
| diisopropyl adipate | 9.0 |
| oleyl alcohol | 14.0 |
| lanolin | 12.0 |

*HLB values are approximate and may vary by about ±1 unit.

Also, as example, the blend of emulsifiers may include HLB values of:

| Ingredient | HLB value* |
|---|---|
| TEFOSE ™ 63 | 9.0-10.0 |
| cetostearyl alcohol | 15.5 |
| Macrogol (6) cetostearyl ether | 10.0-12.0 |
| Macrogol (25) cetostearyl ether | 15.0-17.0 |

*HLB values are approximate and may vary by about ±1 unit.

In some embodiments, the cream may comprise an emulsifier having a hydrophilic-lipophilic balance of from about 9.0 to about 17.0. In some embodiments, the hydrophilic-lipophilic balance is determined by Griffin's method. For example, in Trial 38, the HLB values for the oil phase and the emulsifier blend is as follows:

| Oil Phase | | | |
|---|---|---|---|
| Component | Desired HLB | Percent in Formula | Contribution |
| Medium chain triglycerides | 10.0 | 7.0 | 0.70 |
| Diisopropyl adipate | 9.0 | 7.0 | 0.63 |
| Oleyl alcohol | 14.0 | 7.0 | 0.98 |
| Lanolin | 12.0 | 2.0 | 0.24 |
| | | Oil Phase SUM | 2.55 |
| Emulsifier Blend | | | |
| Component | HLB Value* | Percent in Formula | Contribution |
| Tefose 63 | 9 to 10 | 8.0 | 0.76 |
| Cetostearyl alcohol | 15.5 | 8.0 | 1.24 |
| Macrogol (6) cetostearyl ether | 10 to 12 | 2.0 | 0.22 |
| Macrogol (25) cetostearyl ether | 15 to 17 | 2.0 | 0.32 |
| | | Emulsifier Blend SUM | 2.54 |

*For HLB value ranges, the mid value was used to execute the calculation.

It may be understood from the above calculations that where percentages of the oil phase ingredients are varied, physically stable emulsions may be obtained by varying the percentages of blend emulsifiers so that the required HLB of the oil phase remains closely matched. In embodiments, the HLB may be matched within +/−1 HLB value, within +/−0.5 HLB value or within +/−0.1 HLB value.

Without wishing to be bound by theory, it is surprising that, for example, in Trial 38, using four neutral to hydrophilic emulsifiers, such as TEFOSE 63™ (having an HLB value from about 9.0 to about 10.0) or Macrogol (25) cetostearyl ether (having an HLB value from about 15.0 to about 17.0), in the concentrations or proportions described, results in a cosmetically acceptable emulsion that is non-irritating. Non-ionic surfactants such as those used in embodiments herein may contain irritants such as polyethylene glycol (PEG). Such PEGylated or PEG containing surfactants may be irritating and may cause contact dermatitis at high levels. In some embodiments, the cream formulation may comprise an emulsifier having an HLB value of from about 9.0 to about 17.0 in cream embodiments described herein wherein the cream formulation is cosmetically acceptable and non-irritating. In embodiments, the cream formulation may be non-irritating to even patients with extremely reactive and/or sensitive skin, such as, but not limited to, that typically seen in patients with *rosacea*, eczema, dermatitis, and other conditions of the skin characterized by a disturbance of the epidermal barrier.

Furthermore, it is surprising that in some embodiments, the cream may further produce a long lasting soothing effect on the skin. The term "soothing", as used herein, means that the formulation is moisturizing, softening, cosmetically appealing, non-irritating or generally calming and comforting to the skin or may decrease any erythema (or redness), if present.

Thus, in some embodiments, the cream formulation is soothing to the skin. In some embodiments, the soothing effect of the cream formulations of embodiments herein may be long-lasting. In some embodiments, the soothing effect may last up to at least about four hours, at least about five hours, at least about six hours, at least about seven hours, at least about eight hours, at least about ten hours, at least about 12 hours, at least about 15 hours, at least about 18 hours, at least about 21 hours, at least about 24 hours or at least about 48 hours with a single application. In some embodiments, the soothing effect may last for from about 1 to about 48 hours; from about 1 to about 24 hours; from about 1 to about 21 hours; from about 1 to about 18 hours; from about 1 to about 16 hours; from about 1 to about 12 hours; from about 1 to about 10 hours; from about 1 to about 8 hours; from about 2 to about 24 hours; from about 2 to about 16 hours; from about 2 to about 12 hours; from about 2 to about 8 hours; from about 4 to about 24 hours; from about 4 to about 16 hours; from about 4 to about 12 hours; from about 4 to about 8 hours; from about 6 to about 24 hours; from about 6 to about 16 hours; from about 6 to about 12 hours; from about 6 to about 8 hours; from about 2 to about 6 hours; from about 4 to about 6 hours, or combinations thereof. In some embodiments, this soothing effect may be maintained with daily application of the cream formulation to the skin. In some embodiments, this soothing effect may be maintained for as long as the cream formulation is applied to the skin daily. In some embodiments, this soothing effect may be maintained with daily application of the cream formulation for at least about 1 month, at least about 2 months, at least about 3 months, at least about 4 months, at least about 5 months, at least about 6 months, at least about 9 months, or at least about 12 months.

In some embodiments, it was surprisingly found that the cream formulation may produce long lasting effects on the skin and may modify the long-term course of *rosacea*, i.e. it may be "disease modifying." Specifically, in certain embodiments, the clinical effect of the composition may be maintained long after the final administration of oxymetazoline composition of embodiments herein, including, without limitation, improvement in erythema, telangiectasias, acute and chronic inflammatory lesions such as papules and pustules, phymas or a combination thereof. In some embodiments, the administration of oxymetazoline composition of embodiments herein may slow progression of the disease or disorder, including, without limitation, *rosacea*, erythema, telangiectasias, acute and chronic inflammatory lesions such as papules and pustules, phymas or a combination thereof.

Furthermore, in some embodiments, the therapeutic effect of cream formulations described herein may be maintained for at least about 30 days, for at least 25 days, for at least 20 days, for at least 15 days, for at least 10 days after stopping the administration of the cream formulation. In some embodiments, the therapeutic effect may be maintained for at least about 7 days, for at least about 5 days, or for at least about 4 days after stopping the administration of the cream formulation.

In some embodiments described herein, the cream formulation is cosmetically elegant and highly stable. Without wishing to be bound by theory, it is believed that such cosmetically elegant and stable emulsions may restore and reinforce the epidermal barrier function ordinarily provided by healthy stratum corneum, ceramides, cholesterol and epidermal lipids, providing protection and restoring hydration to the skin.

In some embodiments, the cream formulation comprises an emulsifier in an amount of greater than about 5% and is non-irritating. In some embodiments, the cream formulation comprises an emulsifier in an amount of greater than about 10% and is non-irritating. In some embodiments, the cream formulation comprises an emulsifier in an amount of greater than about 15% and is non-irritating. In some embodiments, the cream formulation comprises an emulsifier in an amount of greater than about 20% and is non-irritating. In some embodiments, the cream formulation comprises an emulsifier in an amount of greater than about 25% and is non-irritating. In some embodiments, the cream formulation comprises an emulsifier in an amount of greater than about 30% and is non-irritating. In some embodiments, the cream formulation comprises propylene glycol and is non-irritating. In some embodiments, the cream formulation comprises propylene glycol in an amount of greater than about 4% and is non-irritating.

The creams of various embodiments may include any number of additional components such as, for example, preservatives, emulsion stabilizers, pH adjusters, chelating agents, viscosity modifiers, antioxidants, surfactants, emollients, opacifying agents, skin conditioners, buffers, fragrances and combinations thereof. In some embodiments, such additional components may provide a dual purpose. For example, certain surfactants may also act as emulsifiers, certain emollients may also act as opacifying agents, and certain buffering agents may also act as chelating agents.

In another embodiment of the invention, the formulation may further comprise a topically active pharmaceutical or cosmetic agent destined, in part, to have a synergistic effect or a therapeutic effect associated with another skin complaint, condition or affliction. Examples of these agents include: anti-*rosacea* agents such as metronidazole, precipitated sulfur, sodium sulfacetamide, or azelaic acid; antibacterial agents (antibiotics) such as clindamycin phosphate, erythromycin, or antibiotics from the tetracycline family; antimycobacterial agents such as dapsone; other antiacne agents such as retinoids, or benzoyl peroxide; antiparasitic agents such as metronidazole, permethrin, crotamiton, thiabendazole, ivermectin or pyrethroids; antifungal agents such as compounds of the imidazole family such as miconazole, clotrimazole, econazole, ketoconazole, or salts thereof, polyene compounds such as amphotericin B, compounds of the allylamine family such as terbinafine; steroidal anti-inflammatory agents such as hydrocortisone triamcinolone, fluocinonide, betamethasone valerate or clobetasol propionate, or non-steroidal anti-inflammatory agents such as ibuprofen and salts thereof, naproxen and salts thereof, or acetaminophen; anesthetic agents such as the "amide" and "ester" anesthetics, including, but not limited to, lidocaine, prilocaine, tetracaine, hydrochloride and derivatives thereof; antipruriginous agents such as thenaldine, trimeprazine, or pramoxine; antiviral agents such as acyclovir; keratolytic agents such as alpha- and beta-hydroxy acids such as glycolic acid or salicylic acid, or urea; anti-free radical agents (antioxidants) such as Vitamin E (alpha tocopherol) and its derivatives, Vitamin C (ascorbic acid), Vitamin A (retinol) and its derivatives, and superoxide dismutases; antiseborrheic agents such as zinc pyrithione and selenium sulfide; antihistamines such as cyproheptadine or hydroxyzine; tricyclic antidepressants such as doxepin hydrochloride; antipsoriatic agents such as calcipotriene, anthralines, coal tar; immune modulating agents such as imiquimod, or the calcineurin inhibitors pimecrolimus and tacrolimus, and chemotherapeutic agents such as 5-fluorouracil, nitrogen mustard, carmustine, bexarotene, mitomycin-c. The topically active pharmaceutical or cosmetic agent may include, without limitation, one or more of hydroxy-acids, polyhydroxy acids, polyhydroxy lactones, ketoacids and related compounds; phenyl alpha acyloxyalkanoic acids and derivatives; N-acyl-aldosamines, N-acylamino acids and related N-acyl compounds; N-(phosphonoalkyl)-aminocarbohydrates, N-(phosphonoalkyl)-amino acids and their related N-(phosphonoalkyl)-compounds; local analgesics and anesthetics; anti-acne agents; anti-bacterial agents; anti-yeast agents; anti-fungal agents; anti-viral agents; anti-infective agents; anti-dandruff agents; anti-dermatitis agents; anti-eczema agents; anti-histamine agents; anti-pruritic agents; anti-emetics; anti-motion sickness agents; anti-inflammatory agents; anti-hyperkeratotic agents; antiperspirants; anti-psoriatic agents; anti-*rosacea* agents; anti-seborrheic agents; hair conditioners and hair treatment agents; anti-aging and anti-wrinkle agents; anti-anxiety agents; anti-convulsant agents; anti-depressant agents; sunblock and sunscreen agents; skin lightening agents; depigmenting agents; astringents; cleansing agents; corn, callus and wart removing agents; skin plumping agents; skin volumizing agents; skin firming agents; matrix metalloproteinase (MMP) inhibitors; topical cardiovascular agents; wound-healing agents; gum disease or oral care agents; amino acids; peptides; dipeptides; tripeptides; glutathione and its derivatives; oligopeptides; polypeptides; carbohydrates; aminocarbohydrates; vitamins; corticosteroids; tanning agents; hormones, retinoids or combinations thereof.

In some embodiments, the topically active pharmaceutical or cosmetic agent may include, without limitation, abacavir, acebutolol, acetaminophen, acetaminosalol, acetazolamide, acetohydroxamic acid, acetylsalicylic acid, N-acylglutathione ethyl ester and other esters, N-acyl proline ethyl ester and other esters, acitretin, aclovate, acrivastine, actiq, acyclovir, adalimumab, adapalene, adefovir dipivoxil, adenosine, albuterol, alefacept, alfuzosin, allopurinol, alloxanthine, almotriptan, alprazolam, alprenolol, aluminum acetate, aluminum chloride, aluminum chlorohydroxide, aluminum hydroxide, amantadine, amiloride, aminacrine, p-aminobenzoic acid, aminocaproic acid, aminolevulinic acid, aminosalicylic acid, amiodarone, amitriptyline, amlodipine, amocarzine, amodiaquin, amorolfine, amoxapine, amphetamine, ampicillin, anagrelide, anastrozole, anthralin, apomorphine, aprepitant, arbutin, aripiprazole, ascorbic acid, ascorbyl palmitate, atazanavir, atenolol, atomoxetine, atropine, azathioprine, azelaic acid, azelastine, azithromycin, bacitracin, beclomethasone dipropionate, bemegride, benazepril, benzilic acid, bendroflumethiazide, benzocaine, benzonatate, benzophenone, benzoyl peroxide, benztropine, bepridil, betamethasone dipropionate, betamethasone valerate, botulinum toxin, brimonidine, brompheniramine, bupivacaine, buprenorphine, bupropion, burimamide, butenafine, butoconazole, cabergoline, caffeic acid, caffeine, calcipotriene, camphor, candesartan cilexetil, capsaicin, carbamazepine, carbamide peroxide, cefditoren pivoxil, cefepime, cefpodoxime proxetil, celecoxib, cetirizine, cevimeline, chitosan, chlordiazepoxide, chlorhexidine, chloroquine, chlorothiazide, chloroxylenol, chlorpheniramine, chlorpromazine, chlorpropamide, ciclopirox, cilostazol, cimetidine, cinacalcet, ciprofloxacin, citalopram, citric acid, cladribine, clarithromycin, clemastine, clindamycin, clioquinol, clobetasol propionate, clocortolone pivalate, clomiphene, clonidine, clopidogrel, clotrimazole, clozapine, cocaine, codeine, cromolyn, crotamiton, cyclizine, cyclobenzaprine, cycloserine, cytarabine, dacarbazine, dalfopristin, dapsone, daptomycin, daunorubicin, deferoxamine, dehydroepiandrosterone, delavirdine, desipramine, desloratadine, desmopressin, desoximetasone, dexamethasone, dexmedetomidine, dexmethylphenidate, dexrazoxane, dextroamphetamine, diazepam, diclofenac, dicyclomine, didanosine, dihydrocodeine, dihydromorphine, diltiazem, 6,8-dimercaptooctanoic acid (dihydrolipoic acid), diphenhydramine, diphenoxylate, dipyridamole, disopyramide, dobutamine, dofetilide, dolasetron, donepezil, dopa esters, dopamide, dopamine, dorzolamide, doxepin, doxorubicin, doxycycline, doxylamine, doxypin, duloxetine, dyclonine, econazole, efalizumab, eflornithine, eletriptan, emtricitabine, enalapril, ephedrine, epinephrine, epinine, epirubicin, eptifibatide, ergotamine, erythromycin, escitalopram, esmolol, esomeprazole, estazolam, estradiol, etanercept, ethacrynic acid, ethinyl estradiol, ethyl pyruvate, etidocaine, etomidate, famciclovir, famotidine, felodipine, fentanyl, ferulic acid, fexofenadine, finasteride, flecamide, fluconazole, flucytosine, fluocinolone acetonide, fluocinonide, 5-fluorouracil, fluoxetine, fluphenazine, flurazepam, fluticasone propionate, fluvoxamine, formoterol, furosemide, galactarolactone, galactonic acid, galactonolactone, galantamine, gatifloxacin, gefitinib, gemcitabine, gemifloxacin, glucarolactone, gluconic acid, gluconolactone, glucuronic acid, glucuronolactone, glycolic acid, griseofulvin, guaifenesin, guanethidine, N-guanylhistamine, haloperidol, haloprogin, hexylresorcinol, homatropine, homosalate, hydralazine, hydrochlorothiazide, hydrocortisone, hydrocortisone 21-acetate, hydrocortisone 17-butyrate, hydrocortisone 17-valerate, hydrogen peroxide, hydromorphone, hydroquinone, hydroquinone monoether, hydroxyzine, hyoscyamine, hypoxanthine, ibuprofen, ichthammol, idarubicin, imatinib, imipramine, imiquimod, indinavir, indomethacin, infliximab, irbesartan, irinotecan, isoetharine, isoproterenol, itraconazole, kanamycin, ketamine, ketanserin, ketoconazole, ketoprofen, ketotifen, kojic acid, labetalol, lactic acid, lactobionic acid, lamivudine, lamotrigine, lansoprazole, letrozole, leuprolide, levalbuterol, levofloxacin, lidocaine, linezolid, lobeline, loratadine, loperamide, losartan, loxapine, lysergic diethylamide, mafenide, malic acid, maltobionic acid, mandelic acid, maprotiline, mebendazole, mecamylamine, meclizine, meclocycline, memantine, menthol, meperidine, mepivacaine, mequinol, mercaptopurine, mescaline, metanephrine, metaproterenol, metaraminol, metformin, methadone, methamphetamine, methotrexate, methoxamine, methyldopa esters, methyldopamide, 3,4-methylenedioxymethamphetamine, methyllactic acid, methyl nicotinate, methylphenidate, methyl salicylate, metiamide, metolazone, metoprolol, metronidazole, mexiletine, miconazole, midazolam, midodrine, miglustat, minocycline, minoxidil, mirtazapine, mitoxantrone, moexiprilat, molindone, monobenzone, morphine, moxifloxacin, moxonidine, mupirocin, nadolol, naftifine, nalbuphine, nalmefene, naloxone, naproxen, nefazodone, nelfinavir, neomycin, nevirapine, nicardipine, nicotine, nifedipine, nimodipine, nisoldipine, nitrofurantoin, nizatidine, norepinephrine, nystatin, octopamine, octreotide, octyl methoxycinnamate, octyl salicylate, ofloxacin, olanzapine, olmesartan medoxomil, olopatadine, omeprazole, ondansetron, oxiconazole, oxotremorine, oxybenzone, oxybutynin, oxycodone, oxymetazoline, padimate 0, palonosetron, pantothenic acid, pantoyl lactone, paroxetine, pemoline, penciclovir, penicillamine, penicillins, pentazocine, pentobarbital, pentostatin, pentoxifylline, pergolide, perindopril, permethrin, phencyclidine, phenelzine, pheniramine, phenmetrazine, phenobarbital, phenol, phenoxybenzamine, phentolamine, phenylephrine, phenylpropanolamine, phenyloin, N-(phosphonomethyl)-glycine, N-(phosphonomethyl)-creatine, N-(phosphonomethyl)-tyramine, physostigmine, pilocarpine, pimecrolimus, pimozide, pindolol, pioglitazone, pipamazine, piperonyl butoxide, pirenzepine, podofilox, podophyllin, povidone iodine, pramipexole, pramoxine, prazosin, prednisone, prenalterol, prilocalne, procainamide, procaine, procarbazine, praline, promazine, promethazine, promethazine propionate, propafenone, propoxyphene, propranolol, propylthiouracil, protriptyline, pseudoephedrine, pyrethrin, pyrilamine, pyrimethamine, quetiapine, quinapril, quinethazone, quinidine, quinupristin, rabeprazole, reserpine, resorcinol, retinal, 13-cis retinoic acid, retinoic acid, retinol, retinyl acetate, retinyl palmitate, ribavirin, ribonic acid, ribonolactone, rifampin, rifapentine, rifaximin, riluzole, rimantadine, risedronic acid, risperidone, ritodrine, rivastigmine, rizatriptan, ropinirole, ropivacaine, salicylamide, salicylic acid, salmeterol, scopolamine, selegiline, selenium sulfide, serotonin, sertaconazole, sertindole, sertraline, shale tar, sibutramine, sildenafil, sotalol, streptomycin, strychnine, sulconazole, sulfacetamide, sulfabenz, sulfabenzamide, sulfabromomethazine, sulfacetamide (sodium sulfacetamide), sulfachlorpyridazine, sulfacytine, sulfadiazine, sulfadimethoxine, sulfadoxine, sulfaguanole, sulfalene, sulfamethizole, sulfamethoxazole, sulfanilamide, sulfapyrazine, sulfapyridine, sulfasalazine, sulfasomizole, sulfathiazole, sulfisoxazole, sulfur, tacrolimus, tadalafil, tamsulosin, tartaric acid, tazarotene, tegaserol, telithromycin, telmisartan, temozolomide, tenofovir disoproxil, terazosin, terbinafine, terbutaline, terconazole, terfenadine, tetracaine, tetracycline, tetrahydrozoline, thalidomide, theobromine, theophylline, thiabendazole, thioctic acid (lipoic acid), thioridazine, thiothixene, thymol, tiagabine, timolol, tinidazole, tioconazole, tirofiban, tizanidine, tobramycin, tocamide, tolazoline, tolbutamide, tolnaftate, tolterodine, tramadol, tranylcypromine, trazodone, triamcinolone acetonide, triamcinolone diacetate, triamcinolone hexacetonide, triamterene, triazolam, triclosan, triflupromazine, trimethoprim, trimipramine, tripelennamine, triprolidine, tromethamine, tropic acid, tyramine, undecylenic acid, urea, urocanic acid, ursodiol, vardenafil, venlafaxine, verapamil, vitamin E acetate, voriconazole, warfarin, wood tar, xanthine, zafirlukast, zaleplon, zinc pyrithione, ziprasidone, zolmitriptan, zolpidem or combinations thereof.

Embodiments are not limited by the number or type of preservatives used in the creams described herein. For example, preservatives useful in embodiments may include, but are not limited to, pentylene glycol, ethylene diamine tetra acetate (EDTA) and its salts, chlorhexidine and its diacetate, dihydrochloride, digluconate derivatives, 1,1,1-trichloro-2-methyl-2-propanol, parachlorometaxylenol, polyhexamethylenebiguanide hydrochloride, dehydroacetic acid, diazolidinyl urea, 2,4-dichlorobenzyl alcohol, 4,4-dimethyl-1,3-oxazolidine, formaldehyde, glutaraldehyde, dimethylidantoin, imidazolidinyl urea, 5-chloro-2-methyl-4-isothiazolin-3-one, ortho-phenylphenol, benzyl alcohol, benzoic acid and its salts, 4-hydroxybenzoic acid and its methyl-, ethyl-, propyl-, isopropyl-, butyl-, isobutyl-esters (parabens), methylparaben, propylparaben, isopropylparabens, isobutylparabens, butylparabens, ethylparaben, trichlosan, 2-phenoxyethanol, phenyl mercuric acetate, quaternium-15, methylsalicylate, salicylic acid and its salts, sorbic acid and its salts, iodopropanyl butylcarbamate, calcium sorbate, zinc pyrithione, 5-bromo-5nitro-1,3-dioxane, 2-bromo-2-nitropropane-1,3-diol, sulfites, bisulfites, and benzalkonium chloride, phenoxyethanol, 2-phenoxyethanol, chloroxylenol, diazolidinyl urea, and combinations thereof. In embodiments, the cream may include any preservative, including, but not limited to. those listed above or a combination thereof. In certain embodiments, the cream may include a combination of methylparaben, propylparaben, and 2-phenoxyethanol.

Preservatives may be provided in any concentration known in the art. For example in some embodiments, the cream may include from about 0.01% to about 3% by weight of any one preservative, and in other embodiments, the cream may include from about 0.05% to about 1.2% by weight of any one preservative. Thus, in creams that include more than one preservative each preservative may be provided at about 0.01% to about 3% by weight or from about 0.05% to about 1.2% by weight.

The creams of various embodiments may include any chelating agent or combination of chelating agents. Examples of the chelating agents useful in various embodiments include, but are not limited to, alanine, sodium polyphosphate, sodium methaphosphate, citric acid, phosphoric acid, tartaric acid, ethylenediamine tetra acetic acid (Edetate, EDTA) and derivatives and salts thereof, dihydroxyethyl glycine, and mixtures thereof. In particular embodiments, the chelating agent may be EDTA or edetate disodium, dihydrate.

The chelating agents may be provided in any effective amount. For example, in some embodiments, the cream may include from about 0.001% to about 2% by weight chelating agent, and in other embodiments, the cream may include from about 0.05% to about 1% by weight chelating agent.

In some embodiments, the cream may include one or more viscosity modifiers. The viscosity modifier of such embodiments may generally include a high molecular weight compound such as, for example, carboxyvinyl polymer, carboxymethyl cellulose, polyvinyl pyrrolidone, hydroxyethyl cellulose, methyl cellulose, natural gum such as gelatin and tragacanth gum, and various alcohols such as polyvinyl alcohol. In other embodiments, the viscosity modifier may include ethanol or isopropyl alcohol. In some embodiments, the viscosity modifier may be a high molecular weight saturated and unsaturated fatty alcohol such as, but are not limited to, carbitol, lauryl alcohol, myristyl alcohol, cetyl alcohol, isocetyl alcohol, stearyl alcohol, isostearyl alcohol, hydroxystearyl alcohol, oleyl alcohol, ricinoleyl alcohol, behenyl alcohol, erucyl alcohol, 2-octyldodecanyl alcohol, cetearyl alcohol, lanolin alcohol, and the like, and in certain embodiments, the viscosity modifier may be oleyl alcohol.

The viscosity modifier may be provided in any amount necessary to create a cream that fits within the viscosity described above, and in certain embodiments, the cream may include from about 0.1% to about 30% by weight viscosity modifier. In some embodiments, the cream may include from about 0.5% to about 20% by weight viscosity modifier. In some embodiments, the cream may include from about 0.5% to about 10% by weight viscosity modifier. In some embodiments, the cream may include a viscosity modifier in an amount from about 2% to about 10% by weight.

The cream of certain embodiments may include one or more antioxidants. Numerous antioxidants are known in the art, and any such antioxidant may be used to prepare the oxymetazoline creams described herein. Examples of suitable antioxidants include, but are not limited to, amino acids such as glycine, histidine, tyrosine, trytophan and derivatives thereof, imidazoles such as urocanic acid and derivatives thereof, peptides, such as D,L-carnosine, D-carnosine, L-carnosine and derivatives thereof such as anserine, carotinoids, carotenes such as α-carotone, β-carotene, lycopene, and derivatives thereof, chlorogenic acid and derivatives thereof, lipoic acid and derivatives thereof such as dihydrlipoic acid, aurothioglycose, propylthiouracil and other thiols such as thioredoxin, glutathione, cysteine, cystine, cystamine and glycosyl, N-acetyl, methyl, ethyl, propyl, amyl, butyl, lauryl, palmitoyl, oleyl, α-linoleyl, cholesteryl and glyceryl esters and salts thereof, dilauryl thiodipropionate, distearyl thiodipropionate, thiodipropionic acid and derivatives thereof such as esters, ethers, peptides, lipids, nucleotides, nucleosides, and salts, sulfoximine compounds such as buthionine sulfoximines, homocysteine sulfoximine, buthionine sulfones, penta-, hexa-, hepta-thionine sulfoximine, unsaturated fatty acids and derivatives thereof such as α-linolenic acid, linoleic acid, oleic acid, folic acid and derivatives thereof, ubiquinone and ubiquinol and derivatives thereof, vitamin C and derivatives there of such as ascorbyl palmitate, magnesium ascorbyl phosphate, ascorbyl acetate, tocopherals and derivatives such as vitamin E acetate, vitamin A and derivatives such as vitamin A palmitate, vitamin B and derivatives thereof, coniferyl benzoate of benzoin resin, rutinic acid and derivatives thereof, α-glycosylrutin, ferulic acid, furfurylidene glucitol, carnosine, butyl hydroxytoluene, trihydroxy-butyrophenone, uric acid and derivatives thereof, mannose and derivatives thereof, superoxide dismutase, zinc and derivatives thereof such as $ZnO$, $ZnSO_4$, selenium and derivatives thereof such as selenium methionine, stilbene and derivatives thereof such as stilbene oxide, trans-stilbene oxide and the like. In particular exemplary embodiments, the one or more antioxidants may include vitamin B, nordihydroguaiaretic acid, butylated hydroxyanisole (BHA), butylated hydroxytoluene (BHT), propyl gallate, erythorbate acid, sodium erythorbate, ascorbir palmitate, and ascorbir stearate. butyl hydroxyanisole, and gallic esters, and in some embodiments, the one or more antioxidants may include BHT.

The one or more antioxidants may be provided in any suitable amount. For example in some embodiments, one or more antioxidants may be from about 0.001% to about 3% by weight of the cream, and in other embodiments, the one or more antioxidants may be from about 0.01% to about 1% by weight of the cream or from about 0.01% to about 0.50% by weight of the cream.

In some embodiments, oxymetazoline creams described herein may include one or more surfactants. Such embodiments are not limited by type of surfactant used; for example, in some embodiments, the one or more surfactants may be anionic surfactants such as alkyl sulfates, alkylether sulfates, alkylsulfonates, alkylaryl sulfonates, alkyl succinates, alkyl sulfosuccinates, N-alkoylsarcosinates, acyl taurates, acyl isethionates, alkyl phosphates, alkyl ether phosphates, alkyl ether carboxylates, α-olefinsulfonates, and the alkali metal and alkaline earth metal salts and ammonium and triethanolamine salts thereof. Such alkyl ether sulfates, alkyl ether phosphates and alkyl ether carboxylates can have between 1 and 10 ethylene oxide or propylene oxide units, and in some embodiments, 1 to 3 ethylene oxide units, per molecule. More specific examples include, but are not limited to, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzene sulfonate, triethanolamine dodecylbenzenesulfonate. In other embodiments, the one or more surfactants may be amphoteric surfactants such as, for example, alkylbetaines, alkylamidopropylbetaines, alkylsulfobetaines, alkylglycinates, alkylcarboxyglycinates, alkylamphoacetates or α-propionates, alkylamphodiacetates or α-dipropionates, and more specifically, cocodimethylsulfopropylbetaine, lauryl betaine, cocamidopropylbetaine or sodium cocamphopropionate.

In certain embodiments, the one or more surfactants may be non-ionic surfactants such as, for example, the reaction products of aliphatic alcohols or alkylphenols having 6 to 20 carbon atoms in a linear or branched alkyl chain with ethylene oxide and/or propylene oxide where the alkylene oxide may be from about 6 moles to about 60 moles per mole of alcohol. In particular embodiments, non-ionic surfactants may include alkylamine oxides, mono- and dialkylalkanolamides, fatty acid esters of polyethylenenglycols, ethoxylated fatty acids amides, saturated fatty acid alcohols reacted with ethylene oxide, alkyl polyglycosides, and sorbitan ether esters, and in some embodiments, the non-ionic surfactant may be ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceteareth-33, ceteareth-34, ceteareth-40, ceteareth-50, ceteareth-55, ceteareth-60, ceteareth-80, ceteareth-100, and the like or combinations thereof, or one or more ceteareth in combination with a fatty acid alcohol such as stearyl alcohol, oleyl alcohol, linoleyl alcohol, arachidyl alcohol, cetyl alcohol, and the like. In certain embodiments, the one or more surfactants may be a commercially available ceteareth containing surfactants such as CREMOPHOR EL®, CREMOPHOR A-6®, CREMPHOR A-25® or combinations thereof.

The one or more surfactants of various embodiments may make up from about 0.1% to about 50% by weight of the cream and in some embodiments, from about 0.5% to about 20% by weight of the cream. In embodiments in which more than one surfactant is provided in the oxymetazoline cream, each surfactant may be from about 0.5% to about 12% by weight of the cream, and in some embodiments, each surfactant of the oxymetazoline cream containing two or more surfactants may be from about 0.5% to about 5% by weight of the cream.

In some embodiments, the oxymetazoline cream may include one or more emollients. Generally, emollients function enable the cream and by extension the active agent to remain on the skin surface or in the stratum corneum. Emollients are well known in the art and are listed, for example, the International Cosmetic Ingredient Dictionary, Eighth Edition, 2000, which is hereby incorporated by reference in its entirety. In certain embodiments, the one or more emollient may be fatty esters, fatty alcohols, or combinations thereof including, but not limited to, diisopropyl adipate, oleyl alcohol, lanolin, isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, polyoxypropylene (5) poloxyethylene (20) cetyl ether (PPG-5-Ceteth-20), 2-ethylhexyl isononoate, 2-ethylhexyl stearate, $C_{12}$ to $C_{16}$ fatty alcohol, $C_{12}$ to $C_{16}$ fatty alcohol lactate, isopropyl lanolate, 2-ethyl-hexyl salicylate, and mixtures thereof. In some embodiments, the one or more emollients may be a combination of fatty alcohols. In certain embodiments, the one or more emollients may be 1-hexadecanol, acetylated lanolin, behenocyl dimethicone, C12-15 alkyl benzoate, cetearyl octanoate, cocoglycerides, dicaprylate/dicaprate dimethicone copolyol, dimethiconol, dioctyl adipate, glyceryl stearate, isocetyl alcohol, isohexadecane, isopentylcyclohexanone, isopropyl palmitate, lauryl lactate, mineral oil, methoxy peg-22/dodecyl glycol copolymer, myristyl lactate, ocryldodecyl neopentanoate, octyl cocoate, octyl palmitate, octyl stearate, octyldodecyl neopentanoate, polyglyceryl-4 isosterate, polyoxyl 40 stearate, polyoxymethylene urea, potassium sorbate, propylene glycol, propylene glycol isoceth-3 acetate, and propylene glycol myristyl ether acetate.

The emollient may be provided in any suitable amount. For example, in some embodiments, the one or more emollient may be from about 1% to about 50% by weight of the cream, and in other embodiments, the emollient may be from about 2% to about 7% by weight of the oxymetazoline cream. As indicated above, the emollient may also be provided in an amount sufficient to provide a ratio of emulsifier to emollient of from about 0.002:1 to about 50:1. In some embodiments, the ratio of emulsifier to emollient is from about 0.1:1 to about 1.8:1, from about 0.2:1 to about 1.8:1, from about 0.3:1 to about 1.8:1, from about 0.4:1 to about 1.8:1, from about 0.5:1 to about 1.8:1, from about 0.7:1 to about 1.8:1, about 0.3:1 to about 1.5:1, about 0.3:1 to about 1.285:1, about 0.3 to about 1:1, about 0.4:1 to about 1.5:1, about 0.4:1 to about 1.285:1, about 0.4:1 to about 1:1, about 0.7:1 to about 1.8:1, about 0.7:1 to about 1.5:1, about 0.7:1 to about 1.285:1, about 0.7:1 to about 1:1, about 0.73:1 to about 1.8:1, about 0.73:1 to about 1.5:1, about 0.73:1 to about 1.285:1, about 0.73:1 to about 1:1, about 0.87:1 to about 1.5:1, about 0.87:1 to about 1.285:1, about 0.87:1 to about 1:1, about 1:1 to about 1.285:1, about 1:1 to about 1.25:1, about 1:1 to about 1.2:1, about 1:1, about 0.87:1, about 0.73:1, or about 0.7:1, or combinations thereof. In such embodiments, the percentage by weight of emollient in the cream will fall within these ranges. In some embodiments, the emulsifier may comprise TEFOSE™ 63, cetostearyl alcohol macrogol (6) cetostearyl ether, macrogol (25) cetostearyl ether or combinations thereof. In some embodiments, the cream may comprise an emulsifier of low molecular weight polyethylene glycol(s) or its esters (e.g. PEG-32 stearate, PEG-6 stearate). In some embodiments, the ratio of TEFOSE™ 63 to cetostearyl alcohol is from about 0.7:1 to about 1.8:1, about 0.7:1 to about 1.5:1, about 0.7:1 to about 1.285:1, about 0.7 to about 1:1, about 0.73:1 to about 1.8:1, about 0.73:1 to about 1.5:1, about 0.73:1 to about 1.285:1, about 0.73:1 to about 1:1, about 0.87:1 to about 1.5:1, about 0.87:1 to about 1.285:1, about 0.87:1 to about 1:1, about 1:1 to about 1.285:1, about 1:1 to about 1.25:1, about 1:1 to about 1.2:1, about 1:1, about 0.87:1, about 0.73:1, or about 0.7:1 or combinations thereof. In some embodiments, the emollient may comprise triglycerides medium chain, diisopropyl adipate, oleyl alcohol, lanolin or combinations thereof.

Without wishing to be bound by theory, from the standpoint of emulsion stability, if an ester is not properly emulsified, the emulsion will exhibit "creaming": separation of the non-polar phase to the top of the cream and aqueous layer underneath. It is believed that the embodiments described herein contain no "true" oil phase and the medium chain triglycerides, diisopropyl adipate and oleyl alcohol are not "true" oils, thus forming an oil-phase-less emulsion. This may make the cream formulation of embodiments herein extremely difficult to emulsify and it may explain why there are so many varied emulsifiers.

In certain embodiments, the oxymetazoline cream may include one or more opacifying agents. Opacifying agents provide color or whiteness to a composition that may otherwise be clear of would have an undesirable color. In some embodiments, components such as, for example, emollients, surfactants, and/or emulsifiers may provide sufficient opaqueness. In other embodiments, one or more additional opacifying agents may be provided to the cream. Opacifying agents are well known in the art and include, but are not limited to, higher fatty alcohols such as cetyl, stearyl, cetostearyl alcohol, arachidyl and behenyl alcohols, solid esters such as cetyl palmitate, glyceryl laurate, stearamide MEA-stearate, high molecular weight fatty amides and alkanolamides and various fatty acid derivatives such as propylene glycol and polyethylene glycol esters. In other embodiments, opacifying agents may include inorganic materials such as, for example, magnesium aluminum silicate, zinc oxide, titanium dioxide or other sunblocking agents.

In embodiments in which an opacifying agent is used, the opacifying agent may be provided in any amount necessary to provide the desired opaqueness. In such embodiments, the opacifying agent may generally be from about 0.01% to about 20% by weight of the cream, and in some embodiments, the opacifying agent may be from about 0.01% to about 5% or about 0.02% to about 2% by weight of the cream.

In some embodiments, the oxymetazoline cream may include one or more skin conditioners. Skin conditioners are components that may generally improve moisture retention in the skin, retard evaporation of water from the skin, and cause plasticization/softening of the skin. Common skin conditioners include, for example, mineral oil, petrolatum, aliphatic alcohols, lanolin and its derivatives, fatty acids, glycol fatty acids, sugars, glycerin, propylene glycol, sorbitols, and polyethylene glycols, vitamins and herbal derivatives. Additional skin conditioners can be found in CTFA Cosmetic Ingredient Handbook, 1st Ed., 1988, which is hereby incorporated herein by reference in its entirety. In some embodiments, the one or more skin conditioners may include, but are not limited to, humectants, such as fructose, glucose, glycerin, propylene glycol, glycereth-26, mannitol and urea, pyrrolidone carboxylic acid, hydrolyzed lecithin, coco-betaine, cysteine hydrochloride, glutamine, polyoxypropylene (15) polyoxyethylene (PPG-15), sodium gluconate, potassium aspartate, oleyl betaine, thiamine hydrochloride, sodium laureth sulfate, sodium hyaluronate, hydrolyzed proteins, hydrolyzed keratin, amino acids, amine oxides, water-soluble derivatives of vitamins A, E and D, amino-functional silicones, ethoxylated glycerin, α-hydroxy acids and salts thereof, water-soluble fatty oil derivatives, such as PEG-24 hydrogenated lanolin, almond oil, grape seed oil and castor oil; numerous other water-soluble skin conditioners listed, and mixtures thereof. In certain embodiments, the skin conditioners may include lanolin or lanolin derivatives, caprylic capric/triglyceride, diisopropyl adipate, and combinations thereof.

Skin conditioners may be provided to the creams of various embodiments in any amount known in the art, and the amount of skin conditioner provided may vary depending upon the type of skin condition or combination of skin conditioners used. In general, the creams of embodiments may include a conditioner in an amount from about 1% to about 50% by weight of the cream or from about 1% to about 25% by weight of the cream.

The oxymetazoline creams of various embodiments may be of neutral to mildly acidic pH to allow for comfortable application to the subject's skin, particularly in light of the disease state or condition suffered by the subject. For example, in various embodiments, the pH of the creams may be from about 2.5 to about 7.0, from about 4.0 to about 7.0, or from about 4.0 to about 5.5 at room temperature. In other embodiments, the pH of such creams may be about 4.5 to about 5.5 at room temperature, and in particular embodiments, the pH of the creams may be about 4.5 at room temperature. Any components or combination of components known and useful in the art may be used to achieve an appropriate pH such as, for example, pH regulators including, but not limited to, lactic acid, citric acid, sodium citrate, glycolic acid, succinic acid, phosphoric acid, monosodium phosphate, disodium phosphate, oxalic acid, dl-malic acid, calcium carbonate, sodium hydroxide and sodium carbonate, sodium hydrogen carbonate, and ammonium hydrogen carbonate. In various embodiments, the total buffer capacity may be from about from about 0 mM to about 600 mM; from about 0 mM to about 600 mM; from about 5 mM to about 600 mM; from about 5 mM to about 400 mM; from about 5 mM to about 300 mM; from about 5 mM to about 200 mM; from about 200 mM to about 400 mM; about 0 mM, about 100 mM, about 200 mM, about 300 mM, about 400 mM, about 500 mM, or about 600 mM.

Embodiments of the invention also include methods for preparing pharmaceutical compositions as described above by, for example, conventional mixing and the like. For example, in some embodiments, oxymetazoline may be combined with any combination of components described above in purified water using conventional mixing, and after a stable emulsion has formed, the pH and viscosity may be adjusted using known methods to achieve a cream having an appropriate pH. In other embodiments, various combinations of components may be combined in purified water by conventional mixing and oxymetazoline may then be added to the mixture. The pH, viscosity, opaqueness, and/or density may be adjusted to achieve a cream which is cosmetically acceptable.

Embodiments are directed to methods of making the cream formulation comprising making a first solution comprising the steps of dissolving preservatives, such as methylparaben and propylparaben, into a solvent, such as polyethylene glycol 300, mixing with a magnetic stirrer until the mixture becomes homogeneous, adding other preservatives, such as 2-phenoxyethanol, to the mixture; making a second solution comprising the steps of heating purified water, and a chelating agent, such as disodium edetate (EDTA); making an oil phase comprising adding emulsifiers, such as Tefose 63, cetostearyl alcohol, Cremophor A-6 and Cremaphor A-25; antioxidants, such as butylated hydroxytoluene; emollients, such as lanolin, diisopropyl adipate, triglycerides medium chain; and viscosity modifiers, such as cetostearyl alcohol; heating and mixing the oil phase; dissolving oxymetazoline into the second solution to create an aqueous phase; adding the first solution to the aqueous phase to make an aqueous phase solution; and adding the aqueous phase solution to the oil phase to make a cream.

Embodiments are directed to methods of making the cream formulation comprising a "one-pot" process. In the one-pot process, the batch may be manufactured in one vessel, kettle or container that can be heated by means of a steam or a heated fluid. First, an oil phase may be made comprising adding emulsifiers, such as Tefose 63, cetostearyl alcohol, Cremophor A-6 and Cremaphor A-25; antioxidants, such as butylated hydroxytoluene; emollients, such as lanolin, diisopropyl adipate, triglycerides medium chain; and viscosity modifiers such as cetostearyl alcohol, heating and mixing the oil phase, then separately in a small container preparing a side-mix by dissolving preservatives, such as methylparaben and propylparaben, into a solvent, such as polyethylene glycol 300, mixing with a magnetic stirrer until the mixture becomes homogeneous, adding other preservatives, such as 2-phenoxyethanol, to the mixture; and a chelating agent, such as disodium edetate (EDTA) and adding this solution to the oil phase, mixing and heating this solution to high temperature and then adding slowly the purified water, the water is added at a rate that the temperature in the pot is maintained at above about 70 degrees C.; once all the water has been added and the cream has been made, dissolving oxymetazoline into the cream.

Yet other embodiments are directed to methods for using the pharmaceutical compositions. In general, the oxymetazoline creams described herein may be administered topically to the skin, and in some embodiments, the oxymetazoline creams may be applied to portions of the skin that exhibit or may be prone to papules, pustules, other inflammatory lesions, phymas (skin thickening) or erythema associated with *rosacea*, purpura, telangiectasias, keratosis pilaris, lupus *miliaris* disseminatus faciei or the like. In other embodiments, oxymetazoline cream may be applied over an entire skin area including those areas not currently exhibiting or prone to papules, pustules, other inflammatory lesions, phymas (skin thickening) or erythema associated with *rosacea*, purpura, telangiectasias, keratosis pilaris, lupus *miliaris* disseminatus faciei or the like.

In various embodiments, the pharmaceutical compositions may be applied to provide an effective amount of oxymetazoline to the subject, and in certain embodiments, the pharmaceutical compositions may be provided in an effective amount to a skin area exhibiting or prone to the symptoms of *rosacea*, telangiectasias, skin thickening, pustules, papules, other skin erythemas, purpura, keratosis pilaris, lupus *miliaris* disseminatus faciei or the like. In some embodiments, an effective amount may be applied to the skin of the subject in need of treatment as the result from a single application of the oxymetazoline cream. In other embodiments, the oxymetazoline cream may be reapplied over the course of, for example, a day, a week, a month, several months, or several years or until the condition is resolved. For example, in one exemplary embodiment, a therapeutic method may include applying the oxymetazoline creams described herein to a skin area exhibiting or prone to symptoms of *rosacea*, skin thickening, telangiectasias, pustules, papules, other skin erythemas, purpura, keratosis pilaris, lupus *miliaris* disseminatus faciei or the like once per day as long as the symptoms persist. In other embodiments, the oxymetazoline cream may be applied as a maintenance therapy, wherein the cream is continuously applied as needed or applied on a scheduled basis over time while the subject is in need of such treatment. In embodiments, a therapeutic method may include applying the cream once per day, 2 times per day, 3 times per day, 4 times per day or as needed or prescribed. In some embodiments, a therapeutic method may include applying the cream pro re nata (PRN or as needed). In other embodiments, a therapeutic method may include applying the oxymetazoline cream 2 times per day, for example, every 4 hours, as long as the symptoms persist. In other exemplary embodiments, a therapeutic method may include applying the oxymetazoline creams 2 or more times, for example, every 6 hours or every 12 hours, per day as long as the symptoms persist. In such embodiments, application of the oxymetazoline creams may be carried out until the symptoms of *rosacea*, skin thickening, telangiectasias, pustules, papules, other skin erythemas, purpura, keratosis pilaris, lupus *miliaris* disseminatus faciei or the like have been substantially reduced or eliminated, and in some embodiments, the amount of oxymetazoline cream applied or the frequency of application may be modified throughout the course of treatment based on the subject's reaction to the pharmaceutical composition and the clinician's recommendations. For example, after symptom reduction or elimination is observed, the amount of oxymetazoline cream applied or the frequency of applications may be modified to maintain a therapeutic effect.

The creams of various embodiments may be applied by any method. For example, in some embodiments, the oxymetazoline cream may be applied by hand by the subject or another person, such as a clinician. In other embodiments, the oxymetazoline cream may be packaged with an applicator such as a wand, swath of cloth, or applicator pad, and in still other embodiments, measured doses of the oxymetazoline cream may be packaged for application by hand. Without wishing to be bound by theory, providing the oxymetazoline cream with a prepackaged applicator or in measured doses may provide a more controlled dose. In general, the subject and/or clinician will ensure that the oxymetazoline cream is applied evenly over the skin area to be treated.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

Example 1

The amount per batch (kg) for each component of the oxymetazoline cream prepared as described below are provided with their concentration by weight of the total cream in Table 1. Table 2 illustrates a function and amount per batch (kg) for each component of the cream prepared as described below with each component's concentration by weight of the total cream wherein Tefose™ 63 is replaced by a mixture of PEG-6 Stearate, Glycol Stearate and PEG-32 Stearate.

Solution 1: In a 2 L glass beaker, 44.0 g of methylparaben, NF and 11.0 g of propylparaben, NF was dissolved into 880 g of polyethylene glycol by mixing with a magnetic stirrer until the mixture became homogeneous. Once the parabens were dissolved, 176.0 g of phenoxyethanol Ph Eur was added to the mixture.

Solution 2: In a separate 36 L capacity stainless steel beaker, heat purified 11305 g of purified water was heated to 75° C. to 78° C. using a hot plate, and 2.2 g of disodium edetate (EDTA), USP, 44.0 g of anhydrous citric acid, USP, and 66.0 g of sodium citrate dehydrate, USP was added to the heated water using a low mixing speed (450 rpm) while maintaining the temperature of the solution at 75° C. to 78° C.

Oil Phase: Into a reactor vessel, preferably an anchor-type, propeller-equipped reactor vessel, 11.0 g of butylated hydroxytoluene, NF, 1760 g of Tefose™ 63 (PEG-& glycol & PEG-32 Stearate), 1760 g of cetostearyl alcohol, NF, 1540 g of triglycerides medium chain, NF (caprylic capric triglycerides), 1540 g of diisopropyl adipate, 1540 g of oleyl alcohol, NF, 440 g of lanolin, USP, 440 g of macrogol (6) cetostearyl ether (Cremophor A-6), Ph Eur, and 440 g of macrogol (25) cetostearyl ether (Cremophor A-25), Ph Eur was added, and the mixture was heated to 73° C. to 75° C. while mixing at a low mixing speed (50 rpm).

While the oil phase was melting, oxymetazoline hydrochloride, USP was dissolved into Solution 2 to create the aqueous phase, and evaporated water was replaced by adding 10.9 g of purified water to the stainless steel beaker. Solution 1 was then added to the aqueous phase while the temperature was maintained at 75° C. to 78° C. with low speed mixing (250 rpm). The resulting aqueous phase solution was than added at a moderate speed to the oil phase in the reactor vessel, preferably an anchor-type, propeller-equipped reactor vessel, with low speed mixing (50 rpm), and stirring was continued until the temperature in the reactor was 40° C. The mixing speed was then lowered to 30 rpm, and the temperature was reduced to 35° C. When 35° C. was reached, the mixing speed was again lowered to 20 rpm. The resulting white cream was manually discharged from the reactor and stored in a two 12 L stainless steel beakers.

TABLE 1

COMPOSITION OF OXYMETAZOLINE CREAM TRIAL 36

| Ingredient | % W/W | Amount per Batch (g) |
|---|---|---|
| Oxymetazoline hydrochloride, USP | 0.01 | 2.2 |
| 2-Phenoxyethanol, Ph Eur | 0.80 | 176 |
| Methylparaben, NF | 0.20 | 44 |
| Propylparaben, NF | 0.05 | 11 |
| Edetate Disodium, Dihydrate, USP | 0.01 | 2.2 |
| Butylated Hydroxytoluene, NF | 0.05 | 11 |
| Polyethylene Glycol 300, NF | 4.0 | 880 |
| Tefose 63 | 8.0 | 1760 |
| Cetostearyl alcohol, NF | 8.0 | 1760 |
| Triglycerides medium chain, NF (caprylic capric/triglycerides) | 7.0 | 1540 |
| Diisopropyl adipate | 7.0 | 1540 |
| Oleyl alcohol, NF | 7.0 | 1540 |
| Lanolin, USP | 2.0 | 440 |
| Cremophor A-6 | 2.0 | 440 |
| Cremophor A-25 | 2.0 | 440 |
| Purified Water, USP (1) | 51.38 | 11305.8 |
| Purified Water, USP (2) | QS | QS |
| Anhydrous Citric Acid, USP | 0.20 | 44 |
| Sodium Citrate Dihydrate, USP | 0.30 | 66 |

TABLE 2

COMPOSITION OF OXYMETAZOLINE CREAM TRIAL 36

| % W/W | Ingredients | Function |
|---|---|---|
| QS | Oxymetazoline Hydrochloride, USP | Active |
| 0.80 | Phenoxyethanol, Ph Eur | Antimicrobial preservative |
| 0.20 | Methylparaben, NF | Antimicrobial preservative |
| 0.05 | Propylparaben, NF | Antimicrobial preservative |
| 0.01 | Disodium Edetate, USP | Chelating agent |
| 0.05 | Butylated Hydroxytoluene, NF | Anti-oxidant |
| 4.00 | Polyethylene Glycol 300, NF | Humectant |
| 5.00 | PEG-6 Stearate | Emulsifier |
| 1.50 | Glycol Stearate | Emulsifier |
| 1.50 | PEG-32 Stearate | Emulsifier |
| 8.00 | Cetostearyl alcohol, NF | Emollient, stiffening agent and emulsion stabilizer |
| 7.00 | Triglycerides medium chain, NF (Caprylic capric triglycerides) | Emollient, oil component |
| 7.00 | Diisopropyl adipate | Emollient, oil component |
| 7.00 | Oleyl Alcohol, NF | Emollient, oil component |
| 2.00 | Lanolin, USP | Emollient, oil component |
| 2.00 | Macrogol (6) Cetostearyl Ether (Cremophor A-6), Ph Eur | Non-ionic o/w emulsifier, consistency enhancer |
| 2.00 | Macrogol (25) Cetostearyl Ether (Cremophor A-25), Ph Eur | Non-ionic o/w emulsifier, consistency enhancer |
| 51.38 | Purified Water, USP | Vehicle |
| 0.20 | Anhydrous Citric Acid, USP | Buffering agent |
| 0.30 | Sodium Citrate Dihydrate, USP | Buffering agent |
| 100.00 | | |

Example 2

Oxymetazoline creams having a variety of formulations were prepared as described in Example 1 in order to obtain a cream which was cosmetically acceptable and had enough consistency to support prolonged exposure at 40° C. without losing its physical integrity. Trial 1 was a base formulation without any API. Trial 2 included 0.1% API to determine the impact that the API would have on the base formulation. The consistency (Viscosity value) revealed that there was no immediate physical impact of the active at 0.1% concentration on the physical integrity of the cream base as compared to the plain base in Trial 1. Trials 3, 5 and 6 were formulations prepared during development work. Trials 7-11 were formulations prepared for the first stability study. Trials 12-13 were formulations containing higher concentrations of oxymetazoline (2% and 1%, respectively). Trials 15-18 were formulations made for toxicology studies. Batches A and B were the same and were combined to make a larger batch for the toxicology studies. Trial 19 was a formulation without preservatives for analytical method development. Trials 20-34 were the first round of optimization formulations. Trials 35-37 were buffered at pH 4.5 and included a high content of cetostearyl alcohol and Tefose™ 63. Trials 38-41 further optimized the Trial 36 formulation with 0.5%, 1%, 2% API and a placebo. Trials 42-43 further optimized the Trial 36 formulation with 0.01%, and 0.15% API and were used in the permeation flux studies. Trial 45 was a large engineering batch of the Trial 36 formulation. Trial 46-48 and 51 were made for analytical method development. Trials 49-50 were made for toxicology studies and contain 0.05% and 0% API, respectively.

TABLE 3

PREPARATION OF OXYMETAZOLINE CREAM: TRIALS 1-7A (% W/W)

|  | Trial 1 | Trial 2 | Trial 3 | Trial 4 | Trial 5 | Trial 6 | Trial 7 | Trial 7A |
|---|---|---|---|---|---|---|---|---|
| Oxymetazoline HCl | 0.000 | 0.100 | 0.025 | NA | 0.100 | 0.050 | 0.150 | 0.025 |
| Phenoxyethanol | 0.800 | 0.800 | 0.800 | NA | 0.800 | 0.800 | 0.800 | 0.800 |
| Methylparaben | 0.200 | 0.200 | 0.200 | NA | 0.200 | 0.200 | 0.200 | 0.200 |
| Propylparaben | 0.050 | 0.050 | 0.050 | NA | 0.050 | 0.050 | 0.050 | 0.050 |
| Disodium Edetate | 0.010 | 0.010 | 0.010 | NA | 0.010 | 0.010 | 0.010 | 0.010 |
| Butylated Hydroxytoluene | 0.050 | 0.050 | 0.050 | NA | 0.050 | 0.050 | 0.050 | 0.050 |
| Polyethylene Glycol 300 | 4.000 | 4.000 | 4.000 | NA | 4.000 | 4.000 | 4.000 | 4.000 |
| Tefose 63 | 7.500 | 7.500 | 8.000 | NA | 8.000 | 8.000 | 8.000 | 8.000 |
| Cetostearyl alcohol | 4.000 | 4.000 | 5.000 | NA | 5.000 | 5.000 | 5.000 | 5.000 |
| Triglycerides medium chain | 7.000 | 7.000 | 7.000 | NA | 7.000 | 7.000 | 7.000 | 7.000 |
| Diisopropyl adipate | 7.000 | 7.000 | 7.000 | NA | 7.000 | 7.000 | 7.000 | 7.000 |
| Oleyl Alcohol | 7.000 | 7.000 | 7.000 | NA | 7.000 | 7.000 | 7.000 | 7.000 |
| Lanolin | 2.000 | 2.000 | 2.000 | NA | 2.000 | 2.000 | 2.000 | 2.000 |
| Macrogol (6) Cetostearyl Ether | 2.000 | 2.000 | 2.000 | NA | 2.000 | 2.000 | 2.000 | 2.000 |
| Macrogol (25) Cetostearyl Ether | 2.000 | 2.000 | 2.000 | NA | 2.000 | 2.000 | 2.000 | 2.000 |
| Anhydrous Citric Acid | 0.000 | 0.000 | 0.000 | NA | 0.000 | 0.000 | 0.000 | 0.000 |
| Sodium Citrate Dihydrate | 0.000 | 0.000 | 0.000 | NA | 0.000 | 0.000 | 0.000 | 0.000 |
| Hydroxyethyl Cellulose | 0.000 | 0.000 | 0.000 | NA | 0.000 | 0.000 | 0.000 | 0.000 |
| Lipoid S-75 | 0.000 | 0.000 | 0.000 | NA | 0.000 | 0.000 | 0.000 | 0.000 |
| Trizma | 0.000 | 0.000 | 0.000 | NA | 0.000 | 0.000 | 0.000 | 0.000 |
| Purified Water | 56.390 | 56.290 | 54.865 | NA | 54.790 | 54.840 | 54.740 | 54.865 |

TABLE 4

PREPARATION OF OXYMETAZOLINE CREAM: TRIALS 8-15A (% W/W)

|  | Trial 8 | Trial 9 | Trial 10 | Trial 11 | Trial 12 | Trial 13 | Trial 14 | Trial 15A |
|---|---|---|---|---|---|---|---|---|
| Oxymetazoline HCl | 0.100 | 0.050 | 0.150 | 0.010 | 2.000 | 1.000 | NA | 2.000 |
| Phenoxyethanol | 0.800 | 0.800 | 0.800 | 0.800 | 0.800 | 0.800 | NA | 0.800 |
| Methylparaben | 0.200 | 0.200 | 0.200 | 0.200 | 0.200 | 0.200 | NA | 0.200 |
| Propylparaben | 0.050 | 0.050 | 0.050 | 0.050 | 0.050 | 0.050 | NA | 0.050 |
| Disodium Edetate | 0.010 | 0.010 | 0.010 | 0.010 | 0.010 | 0.010 | NA | 0.010 |
| Butylated Hydroxytoluene | 0.050 | 0.050 | 0.050 | 0.050 | 0.050 | 0.050 | NA | 0.050 |
| Polyethylene Glycol 300 | 4.000 | 4.000 | 4.000 | 4.000 | 4.000 | 4.000 | NA | 4.000 |
| Tefose 63 | 8.000 | 8.000 | 8.000 | 8.000 | 8.000 | 8.000 | NA | 8.000 |
| Cetostearyl alcohol | 5.000 | 5.000 | 5.000 | 5.000 | 5.000 | 5.000 | NA | 5.000 |
| Triglycerides medium chain | 7.000 | 7.000 | 7.000 | 7.000 | 7.000 | 7.000 | NA | 7.000 |
| Diisopropyl adipate | 7.000 | 7.000 | 7.000 | 7.000 | 7.000 | 7.000 | NA | 7.000 |
| Oleyl Alcohol | 7.000 | 7.000 | 7.000 | 7.000 | 7.000 | 7.000 | NA | 7.000 |
| Lanolin | 2.000 | 2.000 | 2.000 | 2.000 | 2.000 | 2.000 | NA | 2.000 |
| Macrogol (6) Cetostearyl Ether | 2.000 | 2.000 | 2.000 | 2.000 | 2.000 | 2.000 | NA | 2.000 |
| Macrogol (25) Cetostearyl Ether | 2.000 | 2.000 | 2.000 | 2.000 | 2.000 | 2.000 | NA | 2.000 |
| Anhydrous Citric Acid | 0.000 | 0.000 | 0.000 | 0.000 | 0.000 | 0.000 | NA | 0.000 |
| Sodium Citrate Dihydrate | 0.000 | 0.000 | 0.000 | 0.000 | 0.000 | 0.000 | NA | 0.000 |
| Hydroxyethyl Cellulose | 0.000 | 0.000 | 0.000 | 0.000 | 0.000 | 0.000 | NA | 0.000 |
| Lipoid S-75 | 0.000 | 0.000 | 0.000 | 0.000 | 0.000 | 0.000 | NA | 0.000 |
| Trizma | 0.000 | 0.000 | 0.000 | 0.000 | 0.000 | 0.000 | NA | 0.000 |
| Purified Water | 54.790 | 54.840 | 54.740 | 54.880 | 52.890 | 53.890 | NA | 52.890 |

TABLE 5

PREPARATION OF OXYMETAZOLINE CREAM: TRIALS 15B-19 (% W/W)

|  | Trial 15B | Trial 16A | Trial 16B | Trial 17A | Trial 17B | Trial 18A | Trial 18B | Trial 19 |
|---|---|---|---|---|---|---|---|---|
| Oxymetazoline HCl | 2.000 | 1.000 | 1.000 | 0.500 | 0.500 | 0.000 | 0.000 | 0.150 |
| Phenoxyethanol | 0.800 | 0.800 | 0.800 | 0.800 | 0.800 | 0.800 | 0.800 | 0.000 |
| Methylparaben | 0.200 | 0.200 | 0.200 | 0.200 | 0.200 | 0.200 | 0.200 | 0.000 |
| Propylparaben | 0.050 | 0.050 | 0.050 | 0.050 | 0.050 | 0.050 | 0.050 | 0.000 |
| Disodium Edetate | 0.010 | 0.010 | 0.010 | 0.010 | 0.010 | 0.010 | 0.010 | 0.010 |

TABLE 5-continued

PREPARATION OF OXYMETAZOLINE CREAM: TRIALS 15B-19 (% W/W)

|  | Trial 15B | Trial 16A | Trial 16B | Trial 17A | Trial 17B | Trial 18A | Trial 18B | Trial 19 |
|---|---|---|---|---|---|---|---|---|
| Butylated Hydroxytoluene | 0.050 | 0.050 | 0.050 | 0.050 | 0.050 | 0.050 | 0.050 | 0.050 |
| Polyethylene Glycol 300 | 4.000 | 4.000 | 4.000 | 4.000 | 4.000 | 4.000 | 4.000 | 4.000 |
| Tefose 63 | 8.000 | 8.000 | 8.000 | 8.000 | 8.000 | 8.000 | 8.000 | 8.000 |
| Cetostearyl alcohol | 5.000 | 5.000 | 5.000 | 5.000 | 5.000 | 5.000 | 5.000 | 5.000 |
| Triglycerides medium chain | 7.000 | 7.000 | 7.000 | 7.000 | 7.000 | 7.000 | 7.000 | 7.000 |
| Diisopropyl adipate | 7.000 | 7.000 | 7.000 | 7.000 | 7.000 | 7.000 | 7.000 | 7.000 |
| Oleyl Alcohol | 7.000 | 7.000 | 7.000 | 7.000 | 7.000 | 7.000 | 7.000 | 7.000 |
| Lanolin | 2.000 | 2.000 | 2.000 | 2.000 | 2.000 | 2.000 | 2.000 | 2.000 |
| Macrogol (6) Cetostearyl Ether | 2.000 | 2.000 | 2.000 | 2.000 | 2.000 | 2.000 | 2.000 | 2.000 |
| Macrogol (25) Cetostearyl Ether | 2.000 | 2.000 | 2.000 | 2.000 | 2.000 | 2.000 | 2.000 | 2.000 |
| Anhydrous Citric Acid | 0.000 | 0.000 | 0.000 | 0.000 | 0.000 | 0.000 | 0.000 | 0.000 |
| Sodium Citrate Dihydrate | 0.000 | 0.000 | 0.000 | 0.000 | 0.000 | 0.000 | 0.000 | 0.000 |
| Hydroxyethyl Cellulose | 0.000 | 0.000 | 0.000 | 0.000 | 0.000 | 0.000 | 0.000 | 0.000 |
| Lipoid S-75 | 0.000 | 0.000 | 0.000 | 0.000 | 0.000 | 0.000 | 0.000 | 0.000 |
| Trizma | 0.000 | 0.000 | 0.000 | 0.000 | 0.000 | 0.000 | 0.000 | 0.000 |
| Purified Water | 52.890 | 53.890 | 53.890 | 54.390 | 54.390 | 54.890 | 54.890 | 55.790 |

TABLE 6

PREPARATION OF OXYMETAZOLINE CREAM: TRIALS 20-27 (% W/W)

|  | Trial 20 | Trial 21 | Trial 22 | Trial 23 | Trial 24 | Trial 25 | Trial 26 | Trial 27 |
|---|---|---|---|---|---|---|---|---|
| Oxymetazoline HCl | 0.010 | 0.150 | 0.010 | 0.010 | 0.010 | 0.010 | 0.010 | 0.010 |
| Phenoxyethanol | 0.800 | 0.800 | 0.800 | 0.800 | 0.800 | 0.800 | 0.800 | 0.800 |
| Methylparaben | 0.200 | 0.200 | 0.200 | 0.200 | 0.200 | 0.200 | 0.200 | 0.200 |
| Propylparaben | 0.050 | 0.050 | 0.050 | 0.050 | 0.050 | 0.050 | 0.050 | 0.050 |
| Disodium Edetate | 0.010 | 0.010 | 0.010 | 0.010 | 0.010 | 0.010 | 0.010 | 0.010 |
| Butylated Hydroxytoluene | 0.050 | 0.050 | 0.050 | 0.050 | 0.050 | 0.050 | 0.050 | 0.050 |
| Polyethylene Glycol 300 | 4.000 | 4.000 | 4.000 | 4.000 | 4.000 | 4.000 | 4.000 | 4.000 |
| Tefose 63 | 8.000 | 8.000 | 8.000 | 8.000 | 8.000 | 8.000 | 10.000 | 10.000 |
| Cetostearyl alcohol | 5.000 | 5.000 | 5.000 | 5.000 | 5.000 | 5.000 | 8.000 | 10.000 |
| Triglycerides medium chain | 7.000 | 7.000 | 7.000 | 7.000 | 7.000 | 7.000 | 7.000 | 7.000 |
| Diisopropyl adipate | 7.000 | 7.000 | 7.000 | 7.000 | 7.000 | 7.000 | 7.000 | 7.000 |
| Oleyl Alcohol | 7.000 | 7.000 | 7.000 | 7.000 | 7.000 | 7.000 | 7.000 | 7.000 |
| Lanolin | 2.000 | 2.000 | 2.000 | 2.000 | 2.000 | 2.000 | 2.000 | 2.000 |
| Macrogol (6) Cetostearyl Ether | 2.000 | 2.000 | 2.000 | 2.000 | 2.000 | 2.000 | 2.000 | 2.000 |
| Macrogol (25) Cetostearyl Ether | 2.000 | 2.000 | 2.000 | 2.000 | 2.000 | 2.000 | 2.000 | 2.000 |
| Anhydrous Citric Acid | 0.000 | 0.000 | 0.200 | 0.000 | 0.100 | 0.200 | 0.000 | 0.000 |
| Sodium Citrate Dihydrate | 0.000 | 0.000 | 0.300 | 0.000 | 0.450 | 0.300 | 0.000 | 0.000 |
| Hydroxyethyl Cellulose | 0.000 | 0.000 | 0.000 | 0.500 | 0.000 | 0.500 | 0.000 | 0.000 |
| Lipoid S-75 | 0.000 | 0.000 | 0.000 | 0.000 | 0.000 | 0.000 | 0.000 | 0.000 |
| Trizma | 0.000 | 0.000 | 0.000 | 0.000 | 0.000 | 0.000 | 0.000 | 0.000 |
| Purified Water | 54.880 | 54.740 | 54.380 | 54.380 | 54.330 | 53.880 | 49.880 | 47.880 |

TABLE 7

PREPARATION OF OXYMETAZOLINE CREAM: TRIALS 28-35 (% W/W)

|  | Trial 28 | Trial 29 | Trial 30 | Trial 31 | Trial 32 | Trial 33 | Trial 34 | Trial 35 |
|---|---|---|---|---|---|---|---|---|
| Oxymetazoline HCl | 0.010 | 0.010 | 0.010 | 0.010 | 0.010 | 0.150 | 0.150 | 0.010 |
| Phenoxyethanol | 0.800 | 0.800 | 0.800 | 0.800 | 0.800 | 0.800 | 0.800 | 0.800 |
| Methylparaben | 0.200 | 0.200 | 0.200 | 0.200 | 0.200 | 0.200 | 0.200 | 0.200 |
| Propylparaben | 0.050 | 0.050 | 0.050 | 0.050 | 0.050 | 0.050 | 0.050 | 0.050 |
| Disodium Edetate | 0.010 | 0.010 | 0.010 | 0.010 | 0.010 | 0.010 | 0.010 | 0.010 |
| Butylated Hydroxytoluene | 0.050 | 0.050 | 0.050 | 0.050 | 0.050 | 0.050 | 0.050 | 0.050 |
| Polyethylene Glycol 300 | 4.000 | 4.000 | 4.000 | 4.000 | 4.000 | 4.000 | 4.000 | 4.000 |
| Tefose 63 | 8.000 | 8.000 | 8.000 | 8.000 | 8.000 | 8.000 | 8.000 | 10.000 |
| Cetostearyl alcohol | 5.000 | 5.000 | 5.000 | 5.000 | 5.000 | 5.000 | 5.000 | 10.000 |

TABLE 7-continued

PREPARATION OF OXYMETAZOLINE CREAM: TRIALS 28-35 (% W/W)

|  | Trial 28 | Trial 29 | Trial 30 | Trial 31 | Trial 32 | Trial 33 | Trial 34 | Trial 35 |
|---|---|---|---|---|---|---|---|---|
| Triglycerides medium chain | 3.500 | 10.500 | 7.000 | 7.000 | 7.000 | 3.500 | 10.500 | 7.000 |
| Diisopropyl adipate | 3.500 | 10.500 | 7.000 | 7.000 | 7.000 | 3.500 | 10.500 | 7.000 |
| Oleyl Alcohol | 14.000 | 0.000 | 0.000 | 0.000 | 7.000 | 14.000 | 0.000 | 7.000 |
| Lanolin | 2.000 | 2.000 | 2.000 | 2.000 | 2.000 | 2.000 | 2.000 | 2.000 |
| Macrogol (6) Cetostearyl Ether | 2.000 | 2.000 | 2.000 | 2.000 | 1.000 | 2.000 | 2.000 | 2.000 |
| Macrogol (25) Cetostearyl Ether | 2.000 | 2.000 | 2.000 | 2.000 | 1.000 | 2.000 | 2.000 | 2.000 |
| Anhydrous Citric Acid | 0.000 | 0.000 | 0.000 | 0.000 | 0.000 | 0.000 | 0.000 | 0.200 |
| Sodium Citrate Dihydrate | 0.000 | 0.000 | 0.000 | 0.000 | 0.000 | 0.000 | 0.000 | 0.300 |
| Hydroxyethyl Cellulose | 0.000 | 0.000 | 0.000 | 0.000 | 0.000 | 0.000 | 0.000 | 0.000 |
| Lipoid S-75 | 0.000 | 0.000 | 2.000 | 0.000 | 0.000 | 0.000 | 0.000 | 0.000 |
| Trizma | 0.000 | 0.000 | 0.000 | 0.000 | 0.000 | 0.000 | 0.000 | 0.000 |
| Purified Water | 54.880 | 54.880 | 59.880 | 61.880 | 56.880 | 54.740 | 54.740 | 47.380 |

TABLE 8

PREPARATION OF OXYMETAZOLINE CREAM: TRIALS 36-40A (% W/W)

|  | Trial 36 | Trial 37 | Trial 38 | Trial 38A | Trial 39 | Trial 39A | Trial 40 | Trial 40A |
|---|---|---|---|---|---|---|---|---|
| Oxymetazoline HCl | 0.010 | 0.010 | 0.000 | 0.000 | 0.500 | 0.500 | 1.000 | 1.000 |
| Phenoxyethanol | 0.800 | 0.800 | 0.800 | 0.800 | 0.800 | 0.800 | 0.800 | 0.800 |
| Methylparaben | 0.200 | 0.200 | 0.200 | 0.200 | 0.200 | 0.200 | 0.200 | 0.200 |
| Propylparaben | 0.050 | 0.050 | 0.050 | 0.050 | 0.050 | 0.050 | 0.050 | 0.050 |
| Disodium Edetate | 0.010 | 0.010 | 0.010 | 0.010 | 0.010 | 0.010 | 0.010 | 0.010 |
| Butylated Hydroxytoluene | 0.050 | 0.050 | 0.050 | 0.050 | 0.050 | 0.050 | 0.050 | 0.050 |
| Polyethylene Glycol 300 | 4.000 | 4.000 | 4.000 | 4.000 | 4.000 | 4.000 | 4.000 | 4.000 |
| Tefose 63 | 8.000 | 9.000 | 8.000 | 8.000 | 8.000 | 8.000 | 8.000 | 8.000 |
| Cetostearyl alcohol | 8.000 | 7.000 | 8.000 | 8.000 | 8.000 | 8.000 | 8.000 | 8.000 |
| Triglycerides medium chain | 7.000 | 7.000 | 7.000 | 7.000 | 7.000 | 7.000 | 7.000 | 7.000 |
| Diisopropyl adipate | 7.000 | 7.000 | 7.000 | 7.000 | 7.000 | 7.000 | 7.000 | 7.000 |
| Oleyl Alcohol | 7.000 | 7.000 | 7.000 | 7.000 | 7.000 | 7.000 | 7.000 | 7.000 |
| Lanolin | 2.000 | 2.000 | 2.000 | 2.000 | 2.000 | 2.000 | 2.000 | 2.000 |
| Macrogol (6) Cetostearyl Ether | 2.000 | 2.000 | 2.000 | 2.000 | 2.000 | 2.000 | 2.000 | 2.000 |
| Macrogol (25) Cetostearyl Ether | 2.000 | 2.000 | 2.000 | 2.000 | 2.000 | 2.000 | 2.000 | 2.000 |
| Anhydrous Citric Acid | 0.200 | 0.200 | 0.200 | 0.200 | 0.200 | 0.200 | 0.200 | 0.200 |
| Sodium Citrate Dihydrate | 0.300 | 0.300 | 0.300 | 0.300 | 0.300 | 0.300 | 0.300 | 0.300 |
| Hydroxyethyl Cellulose | 0.000 | 0.000 | 0.000 | 0.000 | 0.000 | 0.000 | 0.000 | 0.000 |
| Lipoid S-75 | 0.000 | 0.000 | 0.000 | 0.000 | 0.000 | 0.000 | 0.000 | 0.000 |
| Trizma | 0.000 | 0.000 | 0.000 | 0.000 | 0.000 | 0.000 | 0.000 | 0.000 |
| Purified Water | 51.380 | 51.380 | 51.390 | 51.390 | 50.890 | 50.890 | 50.390 | 50.390 |

TABLE 9

PREPARATION OF OXYMETAZOLINE CREAM: TRIALS 41-47 (% W/W)

|  | Trial 41 | Trial 41A | Trial 42 | Trial 43 | Trial 44 | Trial 45 | Trial 46 | Trial 47 |
|---|---|---|---|---|---|---|---|---|
| Oxymetazoline HCl | 2.000 | 2.000 | 0.010 | 0.150 | NA | 0.000 | 0.500 | 0.250 |
| Phenoxyethanol | 0.800 | 0.800 | 0.800 | 0.800 | NA | 0.800 | 0.800 | 0.800 |
| Methylparaben | 0.200 | 0.200 | 0.200 | 0.200 | NA | 0.200 | 0.200 | 0.200 |
| Propylparaben | 0.050 | 0.050 | 0.050 | 0.050 | NA | 0.050 | 0.050 | 0.050 |
| Disodium Edetate | 0.010 | 0.010 | 0.010 | 0.010 | NA | 0.010 | 0.010 | 0.010 |
| Butylated Hydroxytoluene | 0.050 | 0.050 | 0.050 | 0.050 | NA | 0.050 | 0.050 | 0.050 |
| Polyethylene Glycol 300 | 4.000 | 4.000 | 4.000 | 4.000 | NA | 4.000 | 4.000 | 4.000 |
| Tefose 63 | 8.000 | 8.000 | 8.000 | 8.000 | NA | 8.000 | 8.000 | 8.000 |
| Cetostearyl alcohol | 8.000 | 8.000 | 8.000 | 8.000 | NA | 8.000 | 8.000 | 8.000 |
| Triglycerides medium chain | 7.000 | 7.000 | 7.000 | 7.000 | NA | 7.000 | 7.000 | 7.000 |
| Diisopropyl adipate | 7.000 | 7.000 | 7.000 | 7.000 | NA | 7.000 | 7.000 | 7.000 |
| Oleyl Alcohol | 7.000 | 7.000 | 7.000 | 7.000 | NA | 7.000 | 7.000 | 7.000 |
| Lanolin | 2.000 | 2.000 | 2.000 | 2.000 | NA | 2.000 | 2.000 | 2.000 |

TABLE 9-continued

PREPARATION OF OXYMETAZOLINE CREAM: TRIALS 41-47 (% W/W)

|  | Trial 41 | Trial 41A | Trial 42 | Trial 43 | Trial 44 | Trial 45 | Trial 46 | Trial 47 |
|---|---|---|---|---|---|---|---|---|
| Macrogol (6) Cetostearyl Ether | 2.000 | 2.000 | 2.000 | 2.000 | NA | 2.000 | 2.000 | 2.000 |
| Macrogol (25) Cetostearyl Ether | 2.000 | 2.000 | 2.000 | 2.000 | NA | 2.000 | 2.000 | 2.000 |
| Anhydrous Citric Acid | 0.200 | 0.200 | 0.200 | 0.200 | NA | 0.200 | 0.200 | 0.200 |
| Sodium Citrate Dihydrate | 0.300 | 0.300 | 0.300 | 0.300 | NA | 0.300 | 0.300 | 0.300 |
| Hydroxyethyl Cellulose | 0.000 | 0.000 | 0.000 | 0.000 | NA | 0.000 | 0.000 | 0.000 |
| Lipoid S-75 | 0.000 | 0.000 | 0.000 | 0.000 | NA | 0.000 | 0.000 | 0.000 |
| Trizma | 0.000 | 0.000 | 0.000 | 0.000 | NA | 0.000 | 0.000 | 0.000 |
| Purified Water | 49.390 | 49.390 | 51.380 | 51.240 | NA | 51.390 | 50.890 | 51.140 |

TABLE 10

PREPARATION OF OXYMETAZOLINE CREAM: TRIALS 48-51 (% W/W)

|  | Trial 48 | Trial 49 | Trial 50 | Trial 51 |
|---|---|---|---|---|
| Oxymetazoline HCl | 0.100 | 0.050 | 0.000 | 0.150 |
| Phenoxyethanol | 0.800 | 0.800 | 0.800 | 0.800 |
| Methylparaben | 0.200 | 0.200 | 0.200 | 0.200 |
| Propylparaben | 0.050 | 0.050 | 0.050 | 0.050 |
| Disodium Edetate | 0.010 | 0.010 | 0.010 | 0.010 |
| Butylated Hydroxytoluene | 0.050 | 0.050 | 0.050 | 0.050 |
| Polyethylene Glycol 300 | 4.000 | 4.000 | 4.000 | 4.000 |
| Tefose 63 | 8.000 | 8.000 | 8.000 | 8.000 |
| Cetostearyl alcohol | 8.000 | 8.000 | 8.000 | 8.000 |
| Triglycerides medium chain | 7.000 | 7.000 | 7.000 | 7.000 |
| Diisopropyl adipate | 7.000 | 7.000 | 7.000 | 7.000 |
| Oleyl Alcohol | 7.000 | 7.000 | 7.000 | 7.000 |
| Lanolin | 2.000 | 2.000 | 2.000 | 2.000 |
| Macrogol (6) Cetostearyl Ether | 2.000 | 2.000 | 2.000 | 2.000 |
| Macrogol (25) Cetostearyl Ether | 2.000 | 2.000 | 2.000 | 2.000 |
| Anhydrous Citric Acid | 0.200 | 0.200 | 0.200 | 0.000 |
| Sodium Citrate Dihydrate | 0.300 | 0.300 | 0.300 | 0.000 |
| Hydroxyethyl Cellulose | 0.000 | 0.000 | 0.000 | 0.000 |
| Lipoid S-75 | 0.000 | 0.000 | 0.000 | 0.000 |
| Trizma | 0.000 | 0.000 | 0.000 | 0.000 |
| Purified Water | 51.290 | 51.340 | 51.390 | 51.740 |

The purpose of this protocol was to perform a stability study on Oxymetazoline Topical Creams, 0.05%, 0.10% and 0.15%. The creams were packaged into two packaging configurations; 30-g polyethylene tubes and 30-g glaminate tubes. Approximately 120 tubes of each cream concentration were prepared. The creams were placed on stability for up to 36 months at the nominal storage condition of 25° C./60% RH and for 6 months at accelerated conditions of 40° C./75% RH. Some samples were also stored at the intermediate condition, 30° C./75% RH. The results of this stability study can be found in Tables 11-13. The pH of the product exhibited a tendency to decrease over time. This tendency appeared to be more pronounced in the samples stored at 40° C./75% RH. The observed appearance of the product at 40° C./75% RH indicated that there was a portion of the cream that melted to the point of becoming a liquid. Both of these issues represented a concern for the long term stability of the cream formulation. It is noted from the stand point of chemical stability of the drug, there was no appreciable drop in potency and there was a very low presence of impurities on the samples tested.

TABLE 11

STABILITY STUDY RESULTS - PRODUCT STORED IN POLYETHYLENE TUBES

| Parameters | Initial@Room Temperature | 40°' C./75% RH,. 2 Weeks | 40°' C./75% RH,. 1 Month | 25°' C./60% RH,. 1 Month | 30°' C./65% RH,. 1 Month |
|---|---|---|---|---|---|
| Oxymetazoline HCl Creams 0.01% | | | | | |
| Assay (% LC) | 101.0 | 102.0 | 96.0 | 101.5 | N/R |
| pH | 4.45 | 4.23 | 4.03 | 4.05 | 4.22 |
| Oxymetazoline HCl Creams 0.05% | | | | | |
| Assay (% LC) | 104.3 | 101.3 | 101.3 | 101.8 | 100.6 |
| CP (% Area) | 0.5 | 0.6 | 0.3 | 0.4 | N/R |
| pH | 4.29 | 4.16 | 3.98 | 4.09 | 4.14 |
| Oxymetazoline HCl Creams 0.10%. | | | | | |
| Assay (% LC) | 104.1 | 104.5 | 106.8 | 101.6 | 101.8 |
| CP (%Area) | 0.3 | 0.4 | 0.1 | 0.2 | N/R |
| pH | 4.39 | 4.22 | 3.98 | 4.05 | 4.11 |
| Oxymetazoline HCl Creams 0.15% | | | | | |
| Assay (% LC) | 100.9 | 99.2 | 102.1 | 99.8 | 100.1 |
| CP(% Area) | 0.2 | 0.3 | 0.1 | 0.2 | N/R |
| pH | 4.42 | 4.22 | 3.87 | 4.04 | 4.08 |

N/R = not reported

TABLE 12

STABILITY STUDY RESULTS - PRODUCT STORED IN GLAMINATE TUBES

| Parameters | Initial@Room Temperature | 40°' C./75% RH,. 2 Weeks | Avg | % RSD |
|---|---|---|---|---|
| Oxymetazoline HCl Creams 0.01% | | | | |
| Assay (% LC) | 101.5 | 101.0 | 101.3 | 0.3 |
| pH | 4.38 | 4.11 | 4.2 | 4.5 |
| Oxymetazoline HCl Creams 0.05% | | | | |
| Assay (% LC) | 102.8 | 105.0 | 103.9 | 1.5 |
| CP (% Area) | 0.7 | 0.8 | NA | NA |
| pH | 4.12 | 4.01 | 4.1 | 1.9 |
| Oxymetazoline HCl Creams 0.10%. | | | | |
| Assay (% LC) | 102.1 | 104.0 | 103.1 | 1.3 |
| CP (% Area) | 0.5 | 0.5 | NA | NA |
| pH | 4.13 | 4.01 | 4.1 | 2.1 |
| Oxymetazoline HCl Creams 0.15% | | | | |
| Assay (% LC) | 100.2 | 101.4 | 100.8 | 0.8 |
| CP(% Area) | 0.4 | 0.3 | NA | NA |
| pH | 4.10 | 3.98 | 4.0 | 2.1 |

The appearance of the samples stored for 1 month at 30° C. is within specification (White viscous cream); the homogeneous creams are similar to the samples stored at 25° C.

TABLE 13

STABILITY STUDY RESULTS - APPEARANCE OF PRODUCT IN POLYETHYLENE TUBES AND GLAMINATE TUBES

| Sample Description | Condition | Appearance |
|---|---|---|
| Polyethylene Tubes | | |
| Oxymetazoline HCl Creams 0.01% | 25° C./60% RH, 1 Month | White viscous cream |
| Oxymetazoline HCl Creams 0.05% | 25° C./60% RH, 1 Month | White viscous cream |
| Oxymetazoline HCl Creams 0.10% | 25° C./60% RH, 1 Month | White viscous cream |
| Oxymetazoline HCl Creams 0.15% | 25° C./60% RH, 1 Month | White viscous cream |
| Glaminate tubes | | |
| Oxymetazoline HCl Creams 0.01% | 40° C./75% RH, 1 Month | White viscous cream (not homogeneous) (A portion of the cream was transferred from the tube to a glass culture tube, a different consistency was observed) |
| Oxymetazoline HCl Creams 0.05% | 40° C./75% RH, 1 Month | White viscous cream (not homogeneous) (A portion of the cream was transferred from the tube to a glass culture tube, a different consistency was observed) |
| Oxymetazoline HCl Creams 0.10% | 40° C./75% RH, 1 Month | White viscous cream (not homogeneous) (A portion of the cream was transferred from the tube to a glass culture tube, a different consistency was observed) |
| Oxymetazoline HCl Creams 0.15% | 40° C./75% RH, 1 Month | White viscous cream (not homogeneous) (A portion of the cream was transferred from the tube to a glass culture tube, a different consistency was observed) |

Creams from Trials 20-34 were packaged into 30-g glaminate tubes. The creams were placed on stability for up to 4 weeks at storage condition of 25° C./60% RH at accelerated conditions of 60° C. and 40° C./75% RH and at the intermediate condition 30° C./75% RH. Trials 20-34 were tested initially and after 1 week. Viscosity was measure using a Brookfield RVT, C/P, Spindle CPE-52, 25 rpm, RT. The results are outlined in Table 14.

TABLE 14

STUDY RESULTS

| Sample ID | Viscosity cPs | pH (Initial) | pH (1 week)[2] | Appearance (Initial) | Appearance (1 week)[2] |
|---|---|---|---|---|---|
| Trial # 20 | 1836 | 4.45 | 4.58 | White Viscous Cream (Homogeneous) | White Viscous Cream (Homogeneous) |

TABLE 14-continued

STUDY RESULTS

| Sample ID | Viscosity cPs | pH (Initial) | pH (1 week)[2] | Appearance (Initial) | Appearance (1 week)[2] |
|---|---|---|---|---|---|
| | | | 4.32 | | White Viscous Cream (Homogeneous) |
| | | | 4.16 | | White Viscous Cream (Homogeneous) |
| Trial #21 | 2367 | 3.92 | 3.89 | White Viscous Cream (Homogeneous) | White Viscous Cream (Homogeneous) |
| | | | 3.74 | | White Viscous Cream (Homogeneous) |
| | | | 3.58 | | White Viscous Cream (Homogeneous) |
| Trial #22 | 3450 | 4.57 | 4.55 | White Viscous Cream (Homogeneous) | White Viscous Cream (Homogeneous) |
| | | | 4.57 | | White Viscous Cream (Homogeneous) |
| | | | 4.54 | | White Viscous Cream (Homogeneous) |
| Trial #23 | 6895 | 4.24 | 4.15 | White Viscous Cream (Homogeneous) | White Viscous Cream (Homogeneous) |
| | | | 4.05 | | White Viscous Cream (Homogeneous) |
| | | | 3.93 | | White Viscous Cream with oily spots |
| Trial #24 | 1608 | 5.58 | 5.51 | White Viscous Cream (Homogeneous) | White Viscous Cream (Homogeneous) |
| | | | 5.51 | | White Cream-Lotion |
| | | | 5.48 | | White Viscous Cream (Homogeneous) |
| Trial #25 | 19183[1] | 4.66 | 4.58 | White Viscous Cream (Homogeneous) | White Viscous Cream (Homogeneous) |
| | | | 4.58 | | White Viscous Cream (Homogeneous) |
| | | | 4.58 | | White Viscous Cream (Homogeneous) |
| Trial #26 | 8458[1] | 3.94 | 3.69 | White Viscous Cream (Homogeneous) | White Viscous Cream (Homogeneous) |
| | | | 3.72 | | White Viscous Cream (Homogeneous) |
| | | | 3.64 | | White Viscous Cream (Homogeneous) |
| Trial #27 | 21067 | 4.44 | 4.17 | White Viscous Cream (Homogeneous) | White Viscous Cream (Homogeneous) |
| | | | 4.04 | | White Viscous Cream (Homogeneous) |
| | | | 3.87 | | White Viscous Cream (Homogeneous) |
| Trial #28 | 4695 | 4.61 | 4.54 | White Viscous Cream (Homogeneous) | White Viscous Cream (Homogeneous) |
| | | | 4.38 | | White Viscous Cream (Homogeneous) |
| | | | 4.18 | | White Viscous Cream (Homogeneous) |
| Trial #29 | 4686 | 4.53 | 4.41 | White Viscous Cream (Homogeneous) | White Viscous Cream (Homogeneous) |
| | | | 4.26 | | White Viscous Cream (Homogeneous) |
| | | | 4.23 | | White Cream-Lotion |
| Trial #30 | 6931 | 3.64 | 3.65 | Off-White Viscous Cream (Homogeneous) | Off-White Viscous Cream (Homogeneous) |
| | | | 3.56 | | Off-White Viscous Cream (Homogeneous) |
| | | | 3.55 | | Off-White Viscous Cream (Homogeneous) |
| Trial #31 | 1700 | 5.65 | 5.50 | White Viscous Cream (Homogeneous) | White Viscous Cream (Homogeneous) |
| | | | 5.36 | | White Viscous Cream (Homogeneous) |
| | | | 5.04 | | White Cream-Lotion |
| Trial #32 | 7269 | 3.75 | 3.69 | White Viscous Cream (Homogeneous) | White Viscous Cream (Homogeneous) |
| | | | 3.56 | | White soft Cream |
| | | | 3.62 | | White Lotion |
| Trial #33 | 2580 | 4.25 | 4.23 | White Viscous Cream (Homogeneous) | White Viscous Cream (Homogeneous) |

TABLE 14-continued

STUDY RESULTS

| Sample ID | Viscosity cPs | pH (Initial) | pH (1 week)[2] | Appearance (Initial) | Appearance (1 week)[2] |
|---|---|---|---|---|---|
| | | | 4.07 | | White Cream-Lotion |
| | | | 3.87 | | White Viscous Cream (Homogeneous) |
| Trial #34 | 5639 | 4.09 | 4.03 | White Viscous Cream (Homogeneous) | White Viscous Cream (Homogeneous) |
| | | | 3.95 | | White Cream-Lotion |
| | | | 3.84 | | White Cream-Lotion |

[1]Modified Method used Speed @10 RPM
[2]Order: 25° C./60% RH 40° C./75%/RH 60° C.

Based on the stability studies of Trials 20-34, it appears that buffer systems stabilize the pH of the formulation. Formulations with high content of Cetostearyl Alcohol and Tefose™ 63 show a higher viscosity and a stable physical consistency when exposed to 60° C. temperature for 1 week. While not wishing to be bound by theory, this may be explained due to the two excipients' wax-like consistency and as such they impart a more rigid structure to the cream. Further evaluation of the stability data pointed to formulations which were optimized by buffers and higher wax-like material content. A buffer that could maintain a pH of about 4.5 was selected for Trials 35-37.

Example 3

Oxymetazoline creams formulated as Trials 35-37 were filled into 30 gram tubes and stored at 25° C., 30° C., 40° C., and 60° C. Each cream was initially tested for appearance (Ap), melting point (mDSC), zeta potential (ZP), pH, and viscosity (V), and each sample was reevaluated once per week for 4 weeks to evaluate stability as follows:
Initial: Ap; mDSC; ZP; pH; and V
Week-1 (25; 40; 60): Ap; mDSC; ZP; pH; and V (if Ap passes)
Week-2 (25; 40): Ap; mDSC; ZP; pH; and V (if Ap passes)
Week-4 (25; 40): Ap; mDSC; pH; and V (if Ap passes)
A sensorial evaluation was conducted by a blinded panel. The panel's evaluation of cosmetic acceptability was based on the criteria provided in Table 15:

TABLE 15

CRITERIA FOR COSMETIC ACCEPTABILITY EVALUATION

| Test Category | Scale |
|---|---|
| General Appearance | 7 = Pleasant ↔ 1 = Unpleasant |
| Color | 7 = Pleasant ↔ 1 = Unpleasant |
| Smell | 7 = Pleasant ↔ 1 = Unpleasant |
| Tackiness | 7 = Not Sticky ↔ 1 = Very Sticky |
| Oiliness | 7 = Not Oily ↔ 1 = Very Oily |
| Cosmetic Elegance | 7 = Very elegant ↔ 1 = Not Elegant |
| Ease of Application | 7 = Spreads Easily ↔ 1 = Not Well |
| Speed of Absorption | 7 = Very Quickly ↔ 1 = Very Slowly |
| Overall Application | 7 = Very Pleasant ↔ 1 = Very Unpleasant |
| Irritation/Stinging | 7 = Not Irritating ↔ 1 = Very Irritating |
| Dry Skin | 7 = Not Drying ↔ 1 = Very Drying |
| Moisturizing | 7 = Moisturizing ↔ 1 = Not Moisturizing |
| Can I put Make-up Over Cream | 7 = Strongly Agree ↔ 1 = Strongly Disagree |
| Overall Impression | 7 = Excellent Product ↔ 1 = Terrible Product |

Figure 2:
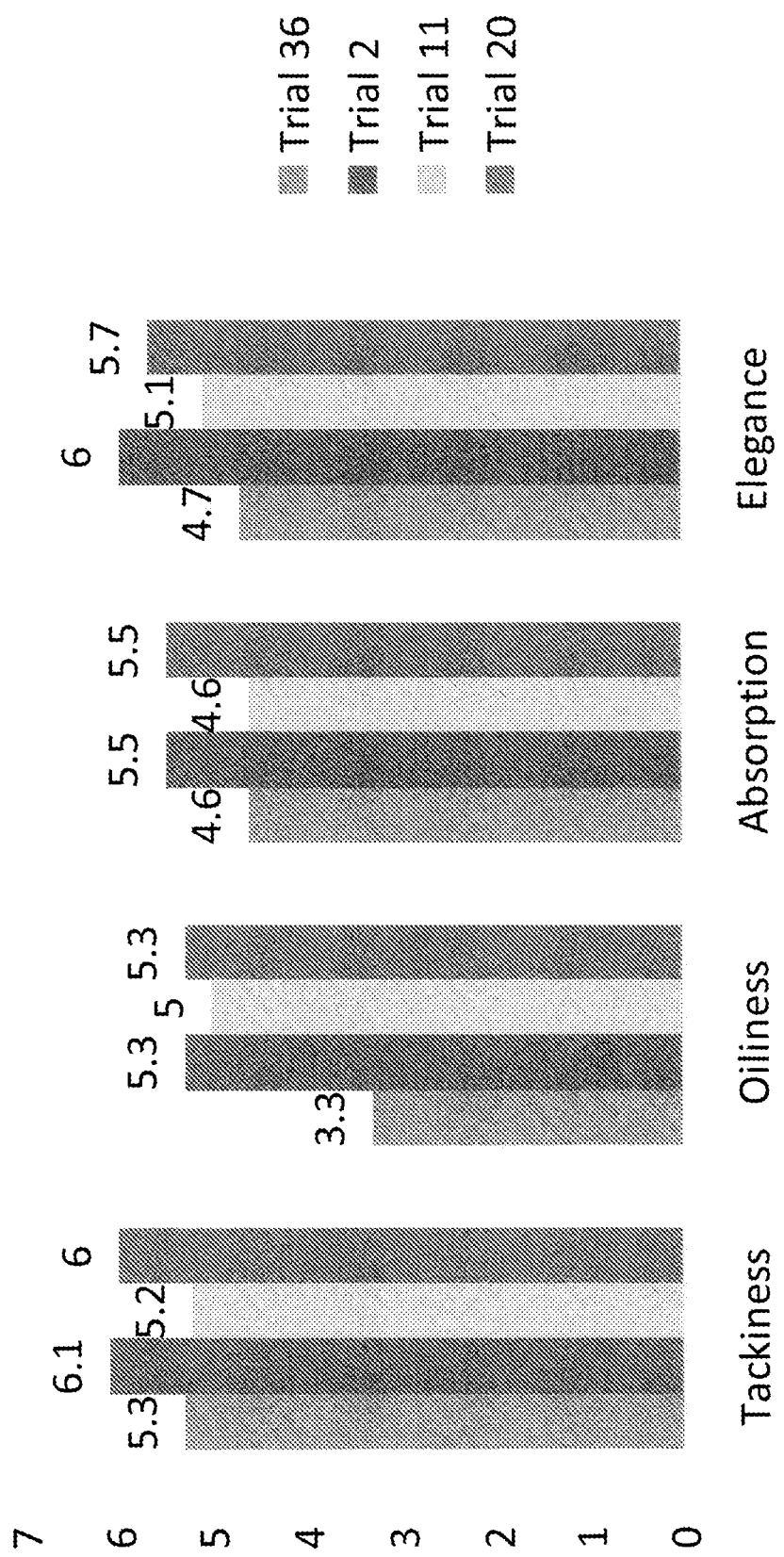
FIG. 2 is a bar graph showing the mean cosmetic acceptability scores including appearance and sensorial evaluation scores for creams of Trial 36, Trial 2, Trial 11 and Trial 20 in key categories.
Figure 3:
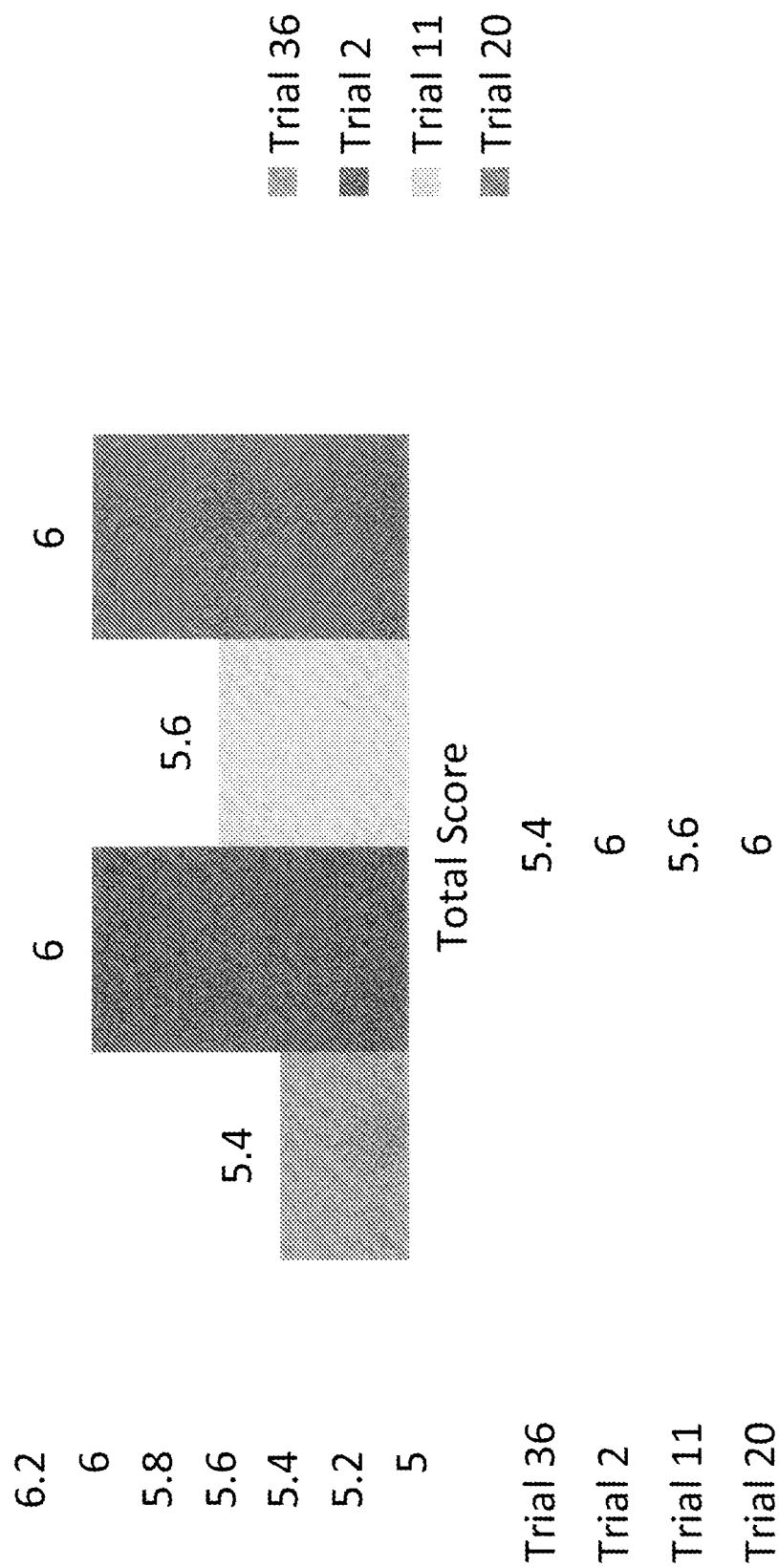
FIG. 3 is a bar graph showing the total mean cosmetic acceptability scores including appearance and sensorial evaluation scores for each of the creams of Trial 36, Trial 2, Trial 11 and Trial 20.

Mean scores by category are provided in FIG. 1, and the mean results for key evaluation categories are provided in FIG. 2. The total mean score is provided in FIG. 3. As indicated in FIG. 1-3, each formulation exhibited acceptable appearance. Overall, the panel selected the formulation of Trial 36 as containing the best sensorial attributes according to the criteria under Table 15.

Tables 16 and 17 contain data on modulated Differential Scanning calorimetry (mDSC) and Zeta Potential (ZP) determinations performed on samples of the Trials 20 through 34 and for the three high wax content formulations Trials 36, 37 and 38. Samples of the creams were subjected to mDSC cycles of heating and cooling from about 7° C. to 60° C. and back. It was found that an optimal formulation combines a buffer system at pH 4.5, such as Trial 22, with a high content of wax-like material (Cetostearyl alcohol and Tefose 63) which demonstrated a physically stable formulation.

Confirmatory studies of mDSC and Zeta Potential were conducted on the formulation of Trial 36. The formulation of Trial 36 was compared with the formulation of Trial 27. Results: Trial 36 formulation showed that no major changes are taking place with respect to the compound structure until 42.5° C. except changes in physical properties of the material after 39° C. in first heat and after 33° C. in second heat. Trial 27 formulation showed that the initial mDSC at 25° C. and after 1 week were less stabile than the formulations of Trial 36. The physical changes are present from about 26° C. and the structural changes show an increased activity after about 40° C. At the same time, the plot of Trial 36 formulation is very similar with the Trial 27 formulation plotted after 1 week at 60° C. stability. The improvement in mDSC of Trial 36 appears to be the combined result of adjusting the ratio of cetostearyl alcohol to Tefose™ 63 to 1:1, optimization of the concentrations of Tefose and cetostearyl alcohol, and optimization of the overall total concentrations and ratio of emulsifier to emollient.

The pH of Trial 36 was adjusted to 4.5 using anhydrous citric acid (0.2% by weight) and sodium citrate dihydrate (0.3% by weight), and the zeta potential of this formula was −5.

Example 4

The formulation of Trial 36 was selected for a formal accelerated stability study. For this study Trials 42 at 0.01% API and Trial 43 at 0.15% API were prepared. The purpose of this protocol was to perform a stability study on Oxymetazoline Topical Creams, 0.01% and 0.15% based on Trial 36. The creams were packaged into 30-g glaminate tubes. Approximately 60 tubes of each cream concentration was prepared. The creams were placed on stability at the nominal storage condition of 25° C./60% RH and at accelerated conditions of 40° C./75% RH. Samples were also stored at the intermediate condition, 30° C./75% RH. Viscosity was measured using a Brookfield RVT, C/P, Spindle CPE-52, 25 rpm, RT.

RESULTS: The appearance, viscosity, pH & assay results of the samples were consistent for the sub-samples from top, middle and bottom of the tube as well as the composite sample. This shows that the manufacturing procedure was carried out efficiently. The results indicate the preparation to be a stable formulation.

Example 5

An in vitro permeation procedure for oxymetazoline cream was developed using the 0.01 and 0.10% w/w oxymetazoline cream. The in vitro experiments were conducted using Hanson Microette Franz Cell apparatus and 0.01N PBS (pH 7.4) as the receiving medium. Other critical parameters were evaluated such as the type of semi-synthetic membrane, sample timing (time dependent release-permeability profile), method sensitivity, specificity and linearity.

Permeation characterization of oxymetazoline cream of different strengths (0.01% w/w, 0.05% w/w, 0.10% w/w and 0.15% w/w) was based on flux study across two different artificial membranes (cellulose acetate and polysulfone). The concentration of oxymetazoline which permeated through the membranes was measured using an HPLC assay.

RESULTS: The oxymetazoline permeation rate over the concentration range studied exhibited a dump and die profile, reaching a peak after 0.5 hours of the cream application. After this period, the drug release gradually declined for the next 24 hours. Oxymetazoline permeability ($AUC_{0-24\ h}$) linearly increased in the concentration range 0.01-0.10% w/w. Further increase of drug concentration (0.10-0.15% w/w), did not lead to a proportional increase in the amount of drug delivered across the membrane. The in vitro membrane transport reached saturation above the 0.1% w/w level irrespective the membrane type used.

Permeability efficiency across the cellulose acetate and polysulfone membranes (expressed as a percent of total drug permeated as a function of time) was similar for all four strengths (30-40%) after the 24 hours application period. Lower oxymetazoline release was observed in the case of polysulfone at the lowest 0.01% w/w level. Without wishing to be bound by theory, this effect may be caused by drug binding to this membrane at this low concentration level.

Example 6

Additional formulations were made using Trial 38 as the base formulation and varying the amount of oxymetazoline. Such formulations included oxymetazoline at 0.01%, 0.05%, 0.06%, 0.1%, 0.15%, 0.25%, 0.5%, 1% and 2.5%, and were found to be stable.

Example 7

A randomized, double-blind, vehicle-controlled, parallel group study of the dose-response profile of Trial 38 formulation was conducted in subjects with erythematous *rosacea*.

OBJECTIVE: the main objective was to evaluate the dose-response relationship of 4 oxymetazoline concentrations of Trial 38 formulation and a matching vehicle cream when applied to the face. A further objective was to evaluate the safety and efficacy of such formulations when applied to the face for 28 consecutive days. A further objective was to evaluate the time course, duration and magnitude of the clinical response on the erythema of *rosacea* when such formulations are applied to the face for 28 consecutive days. A further objective was to evaluate the response of telangiectasias, the "clinician's telangiectasia assessment score," the time course and duration of the clinical response of the telangiectasias of *rosacea* when such formulations are applied to the face for 28 consecutive days.

METHODS: This was a randomized, double-blind, vehicle-controlled, parallel-group study of the Trial 38 base formulation with 0.01%, 0.06%, 0.10%, and 0.15% oxymetazoline and the Trial 38 formulation with no oxymetazoline (vehicle) in subjects with stable moderate to severe erythematous *rosacea*. Approximately 175 subjects (35 per treatment group) were planned; 183 subjects were randomized and applied study medication. Subjects included males and females age 18 years in good general health with a clinical diagnosis of stable erythematous *rosacea*. Inclusion criteria included Subject's Self-Assessment (SSA) and Clinician's Erythema Assessment (CEA) scores of ≥3, ≤3 inflammatory lesions (papules and/or pustules) and no cysts within the treatment area. SSA and CEA scores were graded on a 5-point ordinal scale (0=no signs; 1=minimal; 2=mild; 3=moderate; and 4=severe).

Eligibility of subjects was determined during Visit 1. During Visit 2, eligible subjects were randomized and began a 28-day treatment period, which included Visit 3 on Day 14 and Visit 4 on Day 28. The treatment period was followed by a 7-day no-treatment follow-up period, with Visit 5 on Day 35, at the end of the study. On days between Visit 2 and Visit 4, subjects applied study medication once daily.

Efficacy was evaluated at the study visits by the subject using the 5-point SSA scale and by the investigator using the 5-point CEA scale, the 5-point Clinician's Telangiectasia Assessment (CTA) scale (0=no signs; 1=minimal; 2=mild; 3=moderate; and 4=severe), and lesion counts for total inflammatory lesions. Inferential tests between treatment groups were performed using appropriate analysis of covariance (ANCOVA) models at each post-application assessment time. The primary efficacy analyses were based on the change-from-baseline area under the curve (AUC) for CEA and SSA calculated across all post-baseline visits. Pairwise comparisons between each active treatment group and the vehicle group were performed.

Secondary efficacy analyses characterized the effect of each treatment on the SSA and CEA over the duration of a visit. Mean changes from each visit pre-application to each post-application assessment were evaluated using ANCOVA models including pairwise comparisons between each active treatment group and the vehicle group. For SSA and CEA, subjects were also classified at each post-application assessment as to treatment success on each of the parameters separately, where treatment success was achieved if a subject had a score of <2 or a change from visit-day baseline (Hour 0) of less than −1.

Safety was evaluated by treatment-emergent adverse events (TEAEs), laboratory evaluations, vital signs, and Irritation Signs and Symptoms (ISS).

RESULTS: A total of 183 subjects were randomized, 178 (97%) of whom completed the study. Overall 98.4% of subjects were white, 69.4% were female, and age ranged from 21 to 83 years (mean 51.2).

Efficacy: For CEA, both the 0.10% and 0.15% groups had statistically significantly greater reductions than the vehicle group in AUC over Days 0 to 28 (−14.162 and −13.103 vs −7.456, respectively; p≤0.004). The 0.10% and 0.15% groups had greater reductions in AUC than the 0.01% and 0.06% groups (−8.250 and −10.181, respectively), which both had numerically greater reductions than the vehicle group.

Among the secondary efficacy analyses, change from baseline in CEA by visit showed statistically significantly greater reductions (improvement) with 0.10% than vehicle on Day 0 at 3, 4, 6, and 8 hours; Day 14 at 3, 4, and 8 hours; and Day 28 at 8 hours, and with 0.15% on Day 0 at 3, 6, and 8 hours. There was a statistically significantly higher success rate with 0.10% and 0.15% than vehicle at 2 or 3 time points on Day 0.

As evaluated by the SSA, the AUC showed a greater reduction with 0.10% and 0.15% than with vehicle but the differences were not statistically significant. Consistent improvement was seen with oxymetazoline formulations in secondary efficacy analyses of CEA and SSA, with some statistically significant differences between oxymetazoline formulation groups and the vehicle group (particularly on Day 0 and at 8 hours on Day 28).

Figure 4:
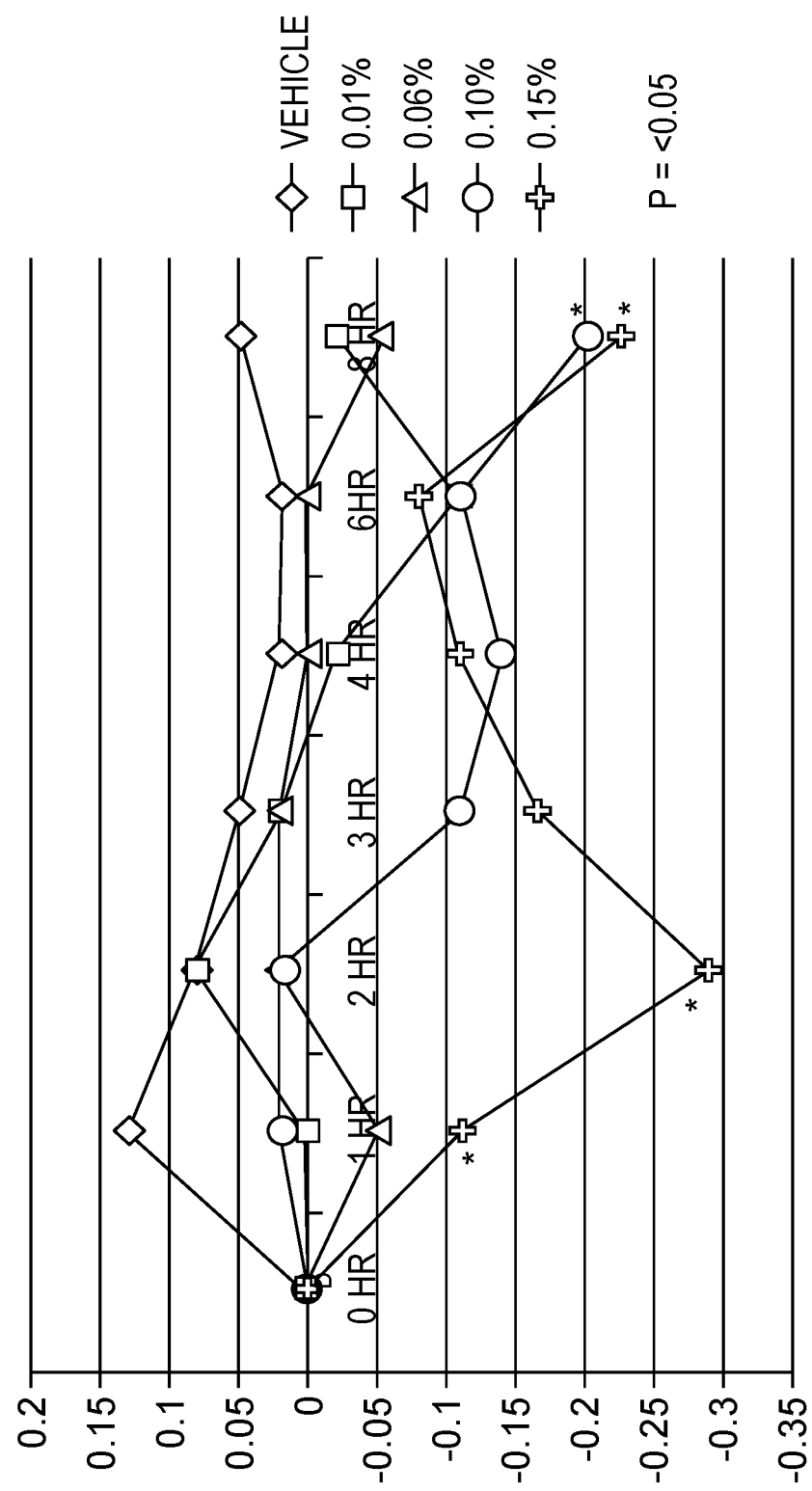
FIG. 4 illustrates the change from baseline of clinician's telangiectasia assessment scores at day 28 of the randomized, double-blind, vehicle-controlled, parallel group study.
Figure 5:
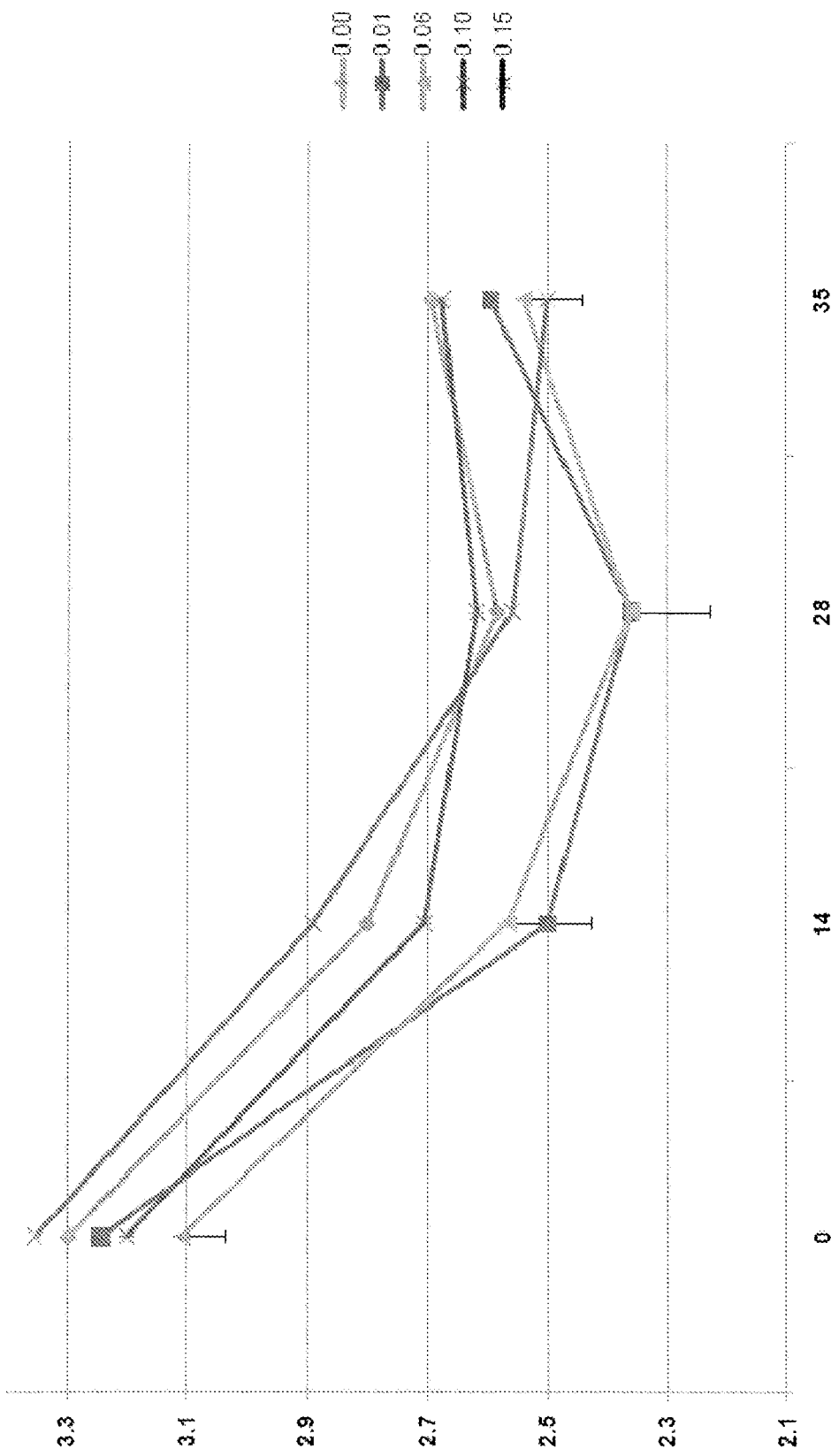
FIG. 5 illustrates the maintenance of clinical effect at day 35 after discontinuing oxymetazoline cream compositions after 28 days of daily application. The improvement in erythema was maintained for at least 7 days after discontinuation of drug application, and there was no rebound/worsening of erythema condition.

Pre-dose CTA results on Days 0, 14, 28, and results on Day 35 are summarized in Table 7. Change from baseline in CTA by visit showed a statistically significantly greater reduction (improvement) with the oxymetazoline formulations than with the vehicle (or improvement compared to worsening with the vehicle) for the 0.10% group on Day 0 at 6 hours and Day 28 at 8 hours, and for the 0.15% group on Day 28 at 1, 2, and 8 hours (Table 7; FIG. 4).

TABLE 16

Clinician's Telangiectasia Assessment: Baseline and Mean Change from Baseline

| | Mean (Standard Deviation) | | |
|---|---|---|---|
| Time | Vehicle (N = 37) | V-101 0.10% (N = 37) | V-101 0.15% (N = 35) |
| Day 0 | | | |
| Baseline | 1.973 (1.093) | 2.459 (1.016) | 1.743 (1.245) |
| 1 hour change | 0.027 (0.440) | −0.108 (0.567) | 0.057 (0.338) |
| 2 hours change | 0.054 (0.575) | −0.189 (0.701) | 0.171 (0.514) |
| 3 hours change | −0.027 (0.552) | −0.351 (0.716) | 0.029 (0.568) |
| 4 hours change | −0.081 (0.493) | −0.243 (0.760) | 0.143 (0.601) |
| 6 hours change | 0.000 (0.333) | −0.378 (0.758)* | 0.057 (0.539) |
| 8 hours change | −0.027 (0.687) | −0.324 (0.709) | 0.057 (0.482) |
| Day 28 | | | |
| Baseline | 1.917 (1.228) | 2.118 (1.274) | 1.882 (1.200) |
| 1 hour change | 0.139 (0.639) | 0.029 (0.388) | −0.118 (0.478)* |
| 2 hours change | 0.083 (0.604) | 0.029 (0.521) | −0.294 (0.579)* |
| 3 hours change | 0.056 (0.715) | −0.118 (0.591) | −0.176 (0.576) |
| 4 hours change | 0.028 (0.845) | −0.147 (0.657) | −0.118 (0.478) |
| 6 hours change | 0.028 (0.696) | −0.118 (0.478) | −0.088 (0.452) |
| 8 hours change | 0.056 (0.532) | −0.206 (0.538)* | −0.235* (0.431) |

CTA scale:
0 = clear skin with no signs of telangiectasia;
1 = almost clear, a few barely visible telangiectasia;
2 = mild, a few visible telangiectasia;
3 = moderate, with the presence of clearly visible telangiectasia;
4 = severe, with the presence of many visible telangiectasia
*$p < 0.0500$ Maintenance of clinical effect and no rebound was observed at day 35 after discontinuing daily application of oxymetazoline cream compositions after 28 days. The improvement in erythema was maintained for at least 7 days after discontinuation of drug application. No tachyphylaxis or rebound were observed.

Safety: There was no apparent relationship between the concentration of oxymetazoline and the incidence of TEAEs overall or for any individual TEAE. Most TEAEs were mild or moderate in severity and considered not related to study medication.

CONCLUSION: Both the 0.10% and 0.15% oxymetazoline cream formulations showed a statistically significant better response than vehicle and a better response than the lower concentrations on the primary efficacy endpoint of CEA as evaluated by the change-from-baseline AUC from Day 0 to Day 28. In addition, there were a number of statistically significant results for the 0.10% and 0.15% concentrations among the secondary efficacy analyses. Specifically, the 0.15% concentration showed statistically significant reductions in Clinician's Telangiectasia Grading scores at hours 3, 4 and 8 on Day 28.

Example 8

Inflammatory lesion study: Subject was a 48 year old male with a 12 year history of *rosacea* characterized by persistent episodes of facial erythema and inflammatory papules and pustules. The subject applied the topical composition of 0.15% oxymetazoline cream once daily to the face and noted both improvement in the erythema and a dramatic decrease in inflammatory lesions (papules and pustules). Daily use of the preparation resulted in complete clearing of all inflammatory lesions within 3 weeks, and the improvement was maintained with continued daily use. Upon discontinuation of daily application, a maintenance of the improvement was reported to continue for 4 weeks, after which time the inflammatory lesions gradually recurred. Upon rechallenge with the 0.15% oxymetazoline cream, the inflammatory lesions gradually returned/regressed.

Example 9

A double-blind, randomized, 2-way crossover study of V-101 cream 0.50% and oxymetazoline nasal spray 0.05% administered in adult subjects with moderate to severe erythematous *rosacea* was conducted. The objectives of this study were to assess the relative bioavailability of a single administration of V-101 cream 0.50% and oxymetazoline nasal spray 0.05% (3 sprays) and to evaluate the safety of V-101 cream 0.50%. A total of 28 subjects ranging in age from 22-63 years of age completed the trial

TABLE 17

Subject Demographics

| Characteristic | Sequence 1 (AB) (N = 14) | Sequence 2 (BA) (N −14) | Total (N = 28) |
|---|---|---|---|
| Age, years | | | |
| Mean (SD) | 43.6 (10.5) | 41.8 (10.7) | 42.7 (10.4) |
| Range | 25-63 | 22-60 | 22-63 |
| Gender, N | | | |
| Male | 4 (28.6%) | 5 (35.7%) | 9 (32.1%) |
| Female | 10 (71.4%) | 9 (64.3%) | 19 (67.9%) |
| Race, N | | | |
| White | 14 (100%) | 14 (100%) | 28 (100%) |

Note:
For sequences AB and BA, A = V-101 cream 0.50% + control (normal saline) nasal spray and B = vehicle cream + oxymetazoline 0.05% nasal spray;
SD = standard deviation At Treatment Visit 1 subjects were treated with one 0.5 g facial application of V 101 cream 0.50% plus 3 sprays of control (normal saline) nasal spray in each nostril (Treatment A) or one 0.5 g facial application of vehicle cream plus 3 sprays of oxymetazoline nasal spray 0.05% in each nostril (Treatment B). The treatment sequence (A then B or B then A) was randomized. Subjects received the opposite treatment at Treatment Visit 2. Evaluations and blood sampling for determination of plasma concentrations of oxymetazoline took place through 12 hours after dosing at each treatment visit.

Greater improvement in erythema, which was clinically and statistically significant, was seen following treatment with V-101 cream 0.50% and control nasal spray compared to that following treatment with vehicle cream and oxymetazoline nasal spray 0.05% as measured by both the subject self assessment and the clinician erythema assessment starting at 2 hours and continuing through the completion of the study at 12 hours postdose.

TABLE 18

Clinician's Erythema Assessment: Mean Predose and Mean Change from Predose for Subjects Completing the Study (Treatment Sequences Combined)

| | Mean (Standard Deviation) | | |
|---|---|---|---|
| Time | V-101 Cream + Control Spray (N = 28) | Vehicle Cream + Oxy 0.05% Spray (N = 28) | P-value[a] |
| Predose | 3.214 (0.418) | 3.214 (0.418) | NA |
| 2 Hours Change | −1.214 (0.833) | −0.143 (0.448) | <0.001 |
| 3 Hours Change | −1.571 (0.920) | −0.036 (0.331) | <0.001 |
| 4 Hours Change | −1.036 (0.793) | −0.036 (0.189) | <0.001 |
| 6 Hours Change | −0.893 (0.832) | 0.000 (0.272) | <0.001 |
| 9 Hours Change | −0.500 (0.694) | −0.036 (0.189) | <0.001 |
| 12 Hours Change | −0.286 (0.460) | 0.000 (0.272) | 0.003 |
| Avg Hours 3 to 6 Change | −1.107 (0.832) | −0.036 (0.189) | <0.001 |

Avg = average,
NA = not applicable,
Oxy = oxymetazoline
[a]P-values were calculated using analysis of covariance based on change from predose and variables were analyzed as continuous variables.

TABLE 19

Subject's Self-Assessment: Mean Predose and Mean Change from Predose for Subjects Completing the Study (Treatment Sequences Combined)

| | Mean (Standard Deviation) | | |
|---|---|---|---|
| Time | V-101 Cream + Control Spray (N = 28) | Vehicle Cream + Oxy 0.05% Spray (N = 28) | P-value[a] |
| Predose | 3.071 (0.262) | 3.107 (0.315) | NA |
| 2 Hours Change | −0.500 (0.638) | 0.000 (0.000) | <0.001 |
| 3 Hours Change | −0.607 (0.629) | 0.036 (0.189) | <0.001 |
| 4 Hours Change | −0.643 (0.731) | 0.036 (0.189) | <0.001 |
| 6 Hours Change | −0.643 (0.731) | 0.036 (0.189) | <0.001 |
| 9 Hours Change | −0.607 (0.737) | 0.036 (0.189) | <0.001 |
| 12 Hours Change | −0.607 (0.786) | 0.036 (0.189) | <0.001 |
| Avg Hours 3 to 6 Change | −0.643 (0.731) | 0.036 (0.189) | <0.001 |

Avg = average,
NA = not applicable,
Oxy = oxymetazoline
[a]P-values were calculated using analysis of covariance based on change from predose and variables were analyzed as continuous variables.

In conclusion, a single topical facial administration of V-101 cream 0.50% under maximum use conditions in subjects with moderate to severe erythematous *rosacea* resulted in minimal systemic exposure when compared with a single administration of Afrin Nasal Spray 0.05%. Topical facial application of V 101 cream 0.50% was well tolerated and significantly reduced erythema from 2 to 12 hours postdose.

The study demonstrated the safety of a single, maximum use facial application of V 101 cream 0.50%. No adverse events considered to be related to study medication were reported during the study.

Example 10

A randomized, double-blind, vehicle-controlled, parallel-group, multicenter study of 2 concentrations of V-101 cream (0.15% and 0.50%) and the matching V-101 vehicle cream in subjects with moderate to severe erythematous *rosacea* was conducted. There were 2 study visits. A total of 85 subjects ranging in age from 27-84 years of age completed the trial.

TABLE 20

| | Subject Demographics | | | |
|---|---|---|---|---|
| Characteristic | Vehicle (N = 27) | V-101 0.15% (N = 29) | V-101 0.50% (N = 29) | Total (N = 85) |
| Age, years | | | | |
| Mean (SD) | 52.3 (12.2) | 46.6 (9.1) | 50.6 (9.3) | 49.8 (10.4) |
| Range | 27-84 | 33-72 | 33-72 | 27-84 |
| Gender, N | | | | |
| Male | 7 (25.9%) | 5 (17.2%) | 4 (13.8%) | 16 (18.8%) |
| Female | 20 (74.1%) | 24 (82.8%) | 24 (82.8%) | 68 (80.0%) |
| Missing | 0 | 0 | 1 (3.4%) | 1 (1.2%) |
| Race, N | | | | |
| White | 27 (100%) | 29 (100%) | 29 (100%) | 85 (100%) |
| Other[a] | 0 | 0 | 0 | 0 |
| Ethnicity, N | | | | |
| Hispanic or Latino | 1 (3.7%) | 2 (6.9%) | 3 (10.3%) | 6 (7.1%) |
| Not Hispanic or Latino | 26 (96.3%) | 27 (93.1%) | 26 (89.7%) | 79 (92.9%) |

Source: Section 14, Table 2

At Visit 1, subjects were screened and eligibility for randomization to study medication was determined during the period of up to 14 days prior to Visit 2. At Visit 2, subjects who were eligible were randomized to study medication (V-101 cream 0.15%, V-101 cream 0.50%, or vehicle cream in a 1:1:1 ratio). A single application of 0.5 g of study medication was administered and the subject was confined at the investigational center until the end of the study evaluations (approximately 12.5 hours).

Pharmacodynamic evaluations were performed using the 5-point SSA scale, the 5-point CEA scale, and the 5-point Clinician's Telangiectasia Assessment (CTA) scale. Safety was evaluated by treatment-emergent adverse events (TE-AEs), laboratory evaluations, vital signs, and electrocardiograms (ECGs).

Pharmacodynamics/Efficacy:

The primary endpoints of change-from-baseline CEA-AUC and SSA-AUC both showed statistically significant reductions in erythema for the 0.50% V-101 group compared with the vehicle group at all time points evaluated, from 3 to 12 hours post-application. The 0.15% V-101 group showed statistically significant reductions in erythema compared with the vehicle group for CEA at all time points except 12 hours and for SSA at 6 and 8 hours. There was a consistent dose response between the V-101 concentrations. The results were similar for treatment success rate. The 0.50% V-101 group had a statistically significant higher overall success rate than the vehicle group from 3 to 8 hours post-application, with overall treatment success defined as a score of <2 or a change from visit-day baseline of <−1 on the CEA and SSA. In the 0.50% V-101 group the overall treatment success rate increased from 17.24% at 3 hours to a maximum of 20.68% at 6 hours. In addition, the 0.50% V-101 group demonstrated statistically significant improvement in CTA compared to vehicle at all time points evaluated.

TABLE 21

Mean Change from Pre-dose as Area Under the Curve (AUC) for Clinician's Erythema Assessment (CEA) and Subject's Self Assessment (SSA)

| Variable | Vehicle (N = 27) | V-101 0.15% (N = 29) | V-101 0.50% (N = 29) |
|---|---|---|---|
| CEA-AUC | | | |
| Mean (SD) | −3.241 (5.120) | −8.155 (5.487) | −14.552 (5.888) |
| P-value[a] | — | 0.000 | 0.000 |
| SSA-AUC | | | |
| Mean (SD) | −2.870 (3.999) | −6.483 (6.973) | −9.379 (5.730) |
| P-value[a] | — | 0.023 | 0.000 |

SD = standard deviation
[a]P-values were calculated by using an analysis of covariance based on baseline value and all variables were analyzed as continuous variables.

Source: Section 14, Tables 9.9.1 and 9.9.2

TABLE 22

Clinician's Erythema Assessment: Baseline and Mean Change from Baseline

| | Mean (Standard Deviation) | | |
|---|---|---|---|
| Time | Vehicle (N = 27) | V-101 0.15% (N = 29) | V-101 0.50% (N = 29) |
| Visit 2 Baseline | 3.296 (0.465) | 3.138 (0.351) | 3.241 (0.435) |
| Post-application change | | | |
| 3 hours | −0.519 (0.700) | −1.069 (0.884)** | −1.759 (0.786)** |
| 4 hours | −0.407 (0.694) | −1.138 (0.875)** | −1.931 (0.704)** |
| 6 hours | −0.333 (0.620) | −0.931 (0.799)** | −1.690 (0.712)** |
| 8 hours | −0.296 (0.542) | −0.655 (0.670)* | −1.310 (0.761)** |

TABLE 22-continued

Clinician's Erythema Assessment: Baseline and Mean Change from Baseline

| | Mean (Standard Deviation) | | |
| --- | --- | --- | --- |
| Time | Vehicle (N = 27) | V-101 0.15% (N = 29) | V-101 0.50% (N = 29) |
| 10 hours | −0.148 (0.456) | −0.448 (0.572)* | −0.828 (0.658)** |
| 12 hours | −0.037 (0.518) | −0.241 (0.511) | −0.483 (0.509)** |
| Average hours 3-6 | −0.420 (0.603) | −1.046 (0.722)** | −1.793 (0.663)** |

CEA scale:
0 = clear skin with no signs of erythema;
1 = almost clear, slight redness;
2 = mild erythema, definite redness;
3 = moderate erythema, marked redness;
4 = severe erythema, fiery redness
P-values were calculated by using an analysis of covariance based on change from visit-day baseline at specified time points. Variables were analyzed as continuous variables.
*p < 0.05,
**p < 0.01

Source: Section 14, Table 9.1

TABLE 22

Subject's Self-Assessment: Baseline and Mean Change from Baseline

| | Mean (Standard Deviation) | | |
| --- | --- | --- | --- |
| Time | Vehicle (N = 27) | V-101 0.15% (N = 29) | V-101 0.50% (N = 29) |
| Visit 2 Baseline Post-application change | 3.222 (0.424) | 3.276 (0.455) | 3.241 (0.435) |
| 3 hours | −0.296 (0.542) | −0.586 (0.733) | −0.828 (0.711)** |
| 4 hours | −0.333 (0.480) | −0.621 (0.677) | −1.034 (0.823)** |
| 6 hours | −0.259 (0.447) | −0.724 (0.797)* | −0.966 (0.680)** |
| 8 hours | −0.259 (0.447) | −0.655 (0.814)* | −1.000 (0.707)** |
| 10 hours | −0.259 (0.526) | −0.552 (0.736) | −0.759 (0.689)** |
| 12 hours | −0.222 (0.577) | −0.517 (0.785) | −0.724 (0.649)** |
| Average hours 3-6 | −0.296 (0.396) | −0.644 (0.701)* | −0.943 (0.661)** |

SSA scale:
0 = clear of unwanted redness,
1 = nearly clear of unwanted redness,
2 = somewhat more redness than I prefer,
4 = completely unacceptable redness
P-values were calculated by using an analysis of covariance based on change from visit-day baseline at specified time points. Variables were analyzed as continuous variables.
*p < 0.05,
**p < 0.01

Source: Section 14, Table 9.2

TABLE 23

Clinician's Telangiectasia Assessment: Baseline and Mean Change from Baseline

| | Mean (Standard Deviation) | | |
| --- | --- | --- | --- |
| Time | Vehicle (N = 27) | V-101 0.15% (N = 29) | V-101 0.50% (N = 29) |
| Visit 2 Baseline Post-application change | 2.074 (0.997) | 1.931 (0.842) | 2.000 (1.102) |
| 3 hours | 0.185 (0.483) | 0.172 (0.658) | −0.138 (0.516)* |
| 4 hours | 0.222 (0.424) | 0.069 (0.371) | −0.172 (0.468)** |
| 6 hours | 0.111 (0.424) | 0.276 (0.455) | −0.172 (0.468)* |
| 8 hours | 0.185 (0.396) | 0.207 (0.491) | −0.172 (0.468)** |
| 10 hours | 0.148 (0.362) | 0.138 (0.441) | −0.172 (0.468)** |
| 12 hours | 0.111 (0.424) | 0.069 (0.258) | −0.103 (0.409)* |
| Average hours 3-6 | 0.173 (0.350) | 0.172 (0.374) | −0.161 (0.442)** |

CTA scale:
0 = clear skin with no signs of telangiectasia;
1 = almost clear, a few barely visible telangiectasia;
2 = mild, a few visible telangiectasia;
3 = moderate, with the presence of clearly visible telangiectasia;
4 = severe, with the presence of many visible telangiectasia
P-values were calculated by using an analysis of covariance based on change from visit-day baseline at specified time points. Variables were analyzed as continuous variables.
*p < 0.05,
**p < 0.01

Source: Section 14, Table 9.3

In conclusion, the main objective of this single-dose study was to evaluate the safety and pharmacodynamic/efficacy profile of 0.15% and 0.50% V-101 cream compared to vehicle cream applied to the face on subjects with moderate to severe erythematous *rosacea*. Both concentrations showed statistically significant reductions in erythema compared with the vehicle, starting at 3 hours post-application, which was the first time point evaluated. Statistically significant greater improvement with 0.50% V-101 cream compared to the vehicle was maintained through 12 hours post-application (the last time point evaluated) for change from baseline in CEA and SSA and through 8 hours post-application for overall treatment success. A clear dose response was demonstrated for all efficacy evaluations, with greater reductions in erythema with 0.50% V-101 as assessed by all clinical indices.

It is of interest to note that a Although there was no entry criterion regarding CTA score and thus a wide variability in baseline scores (Section 14, Table 3), a significant improvement in CTA was seen with 0.50% V-101 throughout the study.

Both concentrations of V-101 cream were well tolerated as assessed by TEAEs, clinical laboratory results, vital signs, and ECGs. There were no notable differences between the concentrations in any of the safety evaluations.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

A number of references have been cited, the entire disclosures of which are incorporated herein in their entirety.

What is claimed is:

1. A cosmetically acceptable and non-irritating pharmaceutical composition in the form of a cream consisting essentially of:
    (a) about 1% oxymetazoline hydrochloride,
    (b) greater than 10% of an emulsifier blend comprising one or more emulsifiers having an HLB value of from about 9.0 to about 17.0, wherein the emulsifier blend comprises (i) one or more ceteareth and (ii) a fatty acid alcohol selected from stearyl alcohol, cetyl alcohol, and a combination thereof,
    (c) an oil phase comprising emollients, the emollients comprising medium chain triglycerides, diisopropyl adipate, oleyl alcohol, and lanolin, and
    (d) a buffering agent,
wherein (i) the composition has a pH of 4.3 to 4.7, and (ii) the HLB contribution of the oil phase is within ±0.5 HLB value of that for the emulsifier blend.

2. The pharmaceutical composition of claim 1, wherein the HLB contribution of the oil phase is within ±0.1 HLB value of that for the emulsifier blend.

* * * * *